United States Patent
Sotomayor et al.

(10) Patent No.: US 9,751,832 B2
(45) Date of Patent: *Sep. 5, 2017

(54) SELECTIVE HISTONE DEACTYLASE 6 INHIBITORS

(71) Applicants: H. LEE MOFFITT CANCER CENTER AND RESEARCH INSTITUTE, INC., Tampa, FL (US); BOARD OF TRUSTEES OF THE UNIVERSITY OF ILLINOIS, Urbana, IL (US)

(72) Inventors: Eduardo M. Sotomayor, Tampa, FL (US); Joel A. Bergman, Chicago, IL (US); Alan P. Kozikowski, Chicago, IL (US); Alejandro V. Villagra, Tampa, FL (US); Karrune V. Woan, Gainesville, FL (US)

(73) Assignees: H. Lee Moffitt Cancer Center and Research Institute, Inc., Tampa, FL (US); Board of Trustees of the University of Illinois, Urbana, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/907,321

(22) PCT Filed: Jul. 30, 2014

(86) PCT No.: PCT/US2014/048906
§ 371 (c)(1),
(2) Date: Jan. 25, 2016

(87) PCT Pub. No.: WO2015/017546
PCT Pub. Date: Feb. 5, 2015

(65) Prior Publication Data
US 2016/0185716 A1    Jun. 30, 2016

Related U.S. Application Data

(60) Provisional application No. 61/860,035, filed on Jul. 30, 2013.

(51) Int. Cl.
| | |
|---|---|
| C07C 275/34 | (2006.01) |
| C07D 213/75 | (2006.01) |
| C07D 231/56 | (2006.01) |
| C07D 233/26 | (2006.01) |
| C07D 233/74 | (2006.01) |
| C07D 233/78 | (2006.01) |
| C07D 239/42 | (2006.01) |
| C07D 261/14 | (2006.01) |
| C07D 209/14 | (2006.01) |
| C07D 295/13 | (2006.01) |
| C07C 275/28 | (2006.01) |
| C07C 275/40 | (2006.01) |
| A61K 31/17 | (2006.01) |
| A61K 31/185 | (2006.01) |

(Continued)

(52) U.S. Cl.
CPC ............ *C07C 275/34* (2013.01); *A61K 31/17* (2013.01); *A61K 31/185* (2013.01); *A61K 31/4045* (2013.01); *A61K 31/416* (2013.01); *A61K 31/42* (2013.01); *A61K 31/437* (2013.01); *A61K 31/44* (2013.01); *A61K 31/505* (2013.01); *A61K 45/06* (2013.01); *C07C 275/28* (2013.01); *C07C 275/40* (2013.01); *C07D 209/14* (2013.01); *C07D 213/75* (2013.01); *C07D 231/56* (2013.01); *C07D 233/26* (2013.01); *C07D 233/74* (2013.01); *C07D 233/78* (2013.01); *C07D 239/42* (2013.01); *C07D 261/14* (2013.01); *C07D 295/13* (2013.01)

(58) Field of Classification Search
CPC ... C07C 275/34; C07C 275/28; C07C 275/40; C07D 261/14; C07D 233/74; C07D 295/13; C07D 209/14; C07D 213/75; C07D 239/42; C07D 231/56; C07D 233/78; C07D 233/26
See application file for complete search history.

(56) References Cited

U.S. PATENT DOCUMENTS 9,409,858 B2 * 8/2016 Sotomayor .......... A61K 31/422
2007/0066646 A1   3/2007 Clauzel et al.
(Continued)

FOREIGN PATENT DOCUMENTS

EP    2456757 A2    5/2012
WO    03070691      3/2003
(Continued)

OTHER PUBLICATIONS

Bergman et al, Journal of Medicinal Chemistry, 2012, 55(12), 9891-9899.*
Aldana-Masangkay, et al., "The Role of HDAC6 in Cancer", J Biomed Biotechnol vol. 2011, article 875824, 2010, 1-10.
Barnden, et al., "Defective TCR expression in transgenic mice constructed using cDNA-based a- and b-chain genes under the control of heterologous regulatory elements", Immunol Cell Biol 76, 1998, 34-40.
Bergman, et al., "Selective histone deacetylase 6 inhibitors bearing substituted urea linkers inhibit melanoma cell growth", J Med Chem 55, 2012, 9891-9899.

(Continued)

*Primary Examiner* — Sudhakar Katakam
(74) *Attorney, Agent, or Firm* — Meunier Carlin & Curfman LLC

(57) ABSTRACT

Disclosed are selective histone deactylase inhibitors (HDACi) that having Formula I. Specifically, the disclosed subject matter relates to compounds having activity as selective HDAC6 inhibitors, methods of making and using the compounds, and compositions comprising the compounds. In still further aspects, the disclosed subject matter relates to methods for treating oncological disorders in a patient. Methods of making and using these inhibitors for the treatment of cancer, in particular melanoma are also disclosed.

7 Claims, 60 Drawing Sheets

(51) Int. Cl.
| | |
|---|---|
| A61K 31/4045 | (2006.01) |
| A61K 31/416 | (2006.01) |
| A61K 31/42 | (2006.01) |
| A61K 31/437 | (2006.01) |
| A61K 31/44 | (2006.01) |
| A61K 31/505 | (2006.01) |
| A61K 45/06 | (2006.01) |

(56) References Cited

U.S. PATENT DOCUMENTS

| | | |
|---|---|---|
| 2008/0033015 A1 | 2/2008 | Belvedere et al. |
| 2011/0212969 A1 | 9/2011 | Blackburn et al. |

FOREIGN PATENT DOCUMENTS

| | | |
|---|---|---|
| WO | 2006013209 | 2/2005 |
| WO | 2005040101 | 6/2005 |
| WO | 2012106343 A2 | 8/2012 |
| WO | 2012178208 A2 | 12/2012 |

OTHER PUBLICATIONS

Boyes, et al., "Regulation of activity of the transcription factor GATA-1 by acetylation", Nature 396, 1998, 594-598.
Brender, et al., "Suppressor of cytokine signaling 3 regulates CD8 T-cell proliferation by inhibition of interleukins 6 and 27", Blood 110, 2007, 2528-2536.
Brush, et al., "Deactylase Inhibitors Disrupt Cellular Complexes Containing Protein Phosphatases and Deacetylases", J Biol Chem. 279, 2004, 7685-7691.
Butler, et al., "Rational Design and Simple Chemistry Yield a Superior, Neuroprotective HDAC6 Inhibitor, Tubastatin A", J Am Chem Soc 132(31), 2010, 10842-10846.
Campas-Moya, "Romidepsin for the Treatment of Cutaneous T-Cell Lymphoma", Drugs of Today 45(11), 2009, 787-795.
Cheng, et al., "A Critical Role for Stat3 Signaling in Immune Tolerance", Immunity 19, 2003, 425-436.
Cheng, et al., "Divergent roles of histone deacetylase 6 (HDAC6) and histone deacetylase 11 (HDAC11) on the transcriptional regulation of IL10 inantigen presenting cells", Mol. Immunol. 60, 2014, 44-53.
De Ruijter, et al., "Histone deacetylases (HDACs): characterization of the classical HDAC family", Biochem. J. 370, 2003, 737-749.
De Zoeten, et al., "Histone Deacetylase 6 and Heat Shock Protein 90 Control the Functions of Foxp3 T-Regulatory Cells", Mol Cell Biol. 31, 2011, 2066-2078.
Facchetti, et al., "Modulation of pro- and anti-apoptotic factors in human melanoma cells exposed to histone deacetylase inhibitors", Apoptosis 9(5), 2004, 573-582.
Ferguson, et al., "Signal-dependent repression of DUSP5 by class I HDACs controls nuclear ERK activity and cardiomyocyte hypertrophy", Proc Natl Acad Sci U S A 110, 2013, 9806-9811.
Foster, et al., "Gene-specific control of inflammation by TLR-induced chromatin modifications", Nature 447, 2007, 972-978.
Fournel, et al., "MGCD0103, a novel isotype-selective histone deacetylase inhibitor, has broad spectrum antitumor activity in vitro and in vivo", Mol Cancer Ther 7(4), 2008, 759-768.
Gabrilovich, et al., "Production of vascular endothelial growth factor by human tumors inhibits the functional nutrition of dendritic cells", Nat Med 2(10), 1996, 1096-1103.
Gao, et al., "Cloning and Functional Characterization of HDAC11, a Novel Member of the Human Histone Deacetylase Family", J Biol Chem 277(28), 2002, 25748-25755.
Georgopoulos, "From immunity to tolerance through HDAC", Nat Immunol 10, 2009, 13-14.
Glozak, et al., "Acetylation and deacetylation of non-histone proteins", Gene 363, 2005, 15-23.
Gozlak, et al., "Histone deacetylases and cancer", Oncogene 26, 2007, 5420-5432.

Grutz, "New insights into the molecular mechanism of interleukin-10-mediated immunosuppression", J Leukoc Biol 77, 2005, 3-15.
Gu, et al., "Activation of p53 Sequence-Specific DNA Binding by Acetylation of the p53 C-Terminal Domain", Cell 90, 1997, 595-606.
Guo, et al., "Efficient Iron-Catalyzed N-Arylation of Aryl Halides with Amines", Org Lett 10(20), 2008, 4513-4516.
Gupta, et al., "Inhibition of histone deacetylase overcomes rapamycin-mediated resistance in diffuse large B-cell lymphoma by inhibiting Akt signaling through mTORC2", Blood 114, 2009, 2926-2935.
Halili, et al., "Differential effects of selective HDAC inhibitors on macrophage inflammatory responses to the Toll-like receptor 4 agonist LPS", J Leukoc Biol 87, 2010, 1103-1114.
Han, et al., "Interleukin-10 overexpression in macrophages suppresses atherosclerosis in hyperlipidemic mice", FASEB J 24, 2010, 2869-2880.
Hubbert, et al., "HDAC6 is a microtubule-associated deacetylase", Nature 417, 2002, 455-458.
International Search Report and Written Opinion for Application No. PCT/US2014/48906 dated Oct. 16, 2014.
Jung, et al., "Histone Deacetylase 6 Functions as a Tumor Suppressor by Activating c-Jun NH2-Terminal Kinase-Mediated Beclin 1-Dependent Autophagic Cell Death in Liver Cancer", Hepatology 56, 2012, 644-657.
Kalin, et al., "Second-Generation Histone Deacetylase 6 Inhibitors Enhance the Immunosuppressive Effects of Foxp3+ T-Regulatory Cells", J Med Chem 55(2), 2012, 639-651.
Kirberg, et al., "Thymic Selection of CD8 § Single Positive Cells with a Class II Major Histocompatibility Complex-restricted Receptor", J Exp Med 180, 1994, 25-34.
Kozikowski, et al., "Use of the Nitrile Oxide Cycloaddition (NOC) Reaction for Molecular Probe Generation: A New Class of Enzyme Selective Histone Deacetylase Inhibitors (HDACIs) Showing Picomolar Activity at HDAC6", Journal of Medicinal Chemistry 51, 2008, 4370-4373.
Kwong, et al., "Copper-Catalyzed Coupling of Alkylamines and Aryl Iodides: An Efficient System Even in an Air Atmosphere", Org Lett 4(4), 2002, 581-584.
Lam, et al., "Histone deacetylase 6—mediated selective autophagy regulates COPD-associated cilia dysfunction", J Clin Invest. 123, 2013, 5212-5230.
Lee, et al., "Characterization of circulating T cells specific for tumor-associated antigens in melanoma patients", Nat Med 5, 1999, 677-685.
Li, et al., "Contextual Regulation of Inflammation: A Duet by Transforming Growth Factor-b and Interleukin-10", Immunity 28, 2008, 468-476.
Liu, et al., "Modulation of Histone Deacetylase 6 (HDAC6) Nuclear Import and Tubulin Deacetylase Activity through Acetylation", J Biol Chem. 287, 2012, 29168-29174.
Mann, et al., "Vorinostat for Treatment of Cutaneous Manifestations of Advanced Primary Cutaneous T-Cell Lymphoma", Clin Cancer Res 13, 2007, 2318-2322.
Marizo, et al., "E2F Family Members Are Differentially Regulated by Reversible Acetylation", J Biol Chem. 275, 2000, 10887-10892.
Marks, et al., "Dimethyl sulfoxide to vorinostat: development of this histone deacetylase inhibitor as an anticancer drug", Nat Biotech 25, 2007, 84-90.
Medzhitov, et al., "Transcriptional control of the inflammatory response", Nat Rev Immunol. 9, 2009, 692-703.
Minucci, et al., "Histone deacetylase inhibitors and the promise of epigenetic (and more) treatments for cancer", Nat Rev Cancer 6, 2006, 38-51.
Murai, et al., "Interleukin 10 acts on regulatory T cells to maintain expression of the transcription factor Foxp3 and suppressive function in mice with colitis", Nat Immunol 10, 2009, 1178-1184.
Murray, P. "The JAK-STAT Signaling Pathway: Input and Output Integration", J Immunol. 178, 2007, 2623-2629.
Niemand, et al., "Activation of STAT3 by IL-6 and IL-10 in Primary Human Macrophages is Differentially Modulated by Suppressor of Cytokine Signaling 3", J Immunol 170, 2003, 3263-3272.

(56) References Cited

OTHER PUBLICATIONS

Noonan, et al., "Activated Marrow-Infiltrating Lymphocytes Effectively Target Plasma Cells and Their Clonogenic Precursors", Cancer Res 65, 2005, 2026-34.
Okano, et al., "Synthesis of Secondary Arylamines through Copper-Mediated Intermolecular Aryl Amination", Org Lett 5(26), 2003, 4987-4990.
Palijan, et al., "Function of Histone Deacetylase 6 as a Cofactor of Nuclear Receptor Coregulator LCoR", J Biol Chem. 284, 2009, 30264-30274.
Parmigiani, et al., "HDAC6 is a specific deacetylase of peroxiredoxins and is involved in redox regulation", Proc Nat Acad Sci USA 105(28), 2008, 9633-9638.
Peltonen, et al., "Melanoma cell lines are susceptible to histone deacetylase inhibitor TSA provoked cell cycle arrest and apoptosis", Pigment Cell Res 18(3), 2005, 196-202.
Pfaffl, et al., "A new mathematical model for relative quantification in real-time RT-PCR", Nucl. Acids Res. 29, 2001, 2002-2007.
Ray, et al., "Requirement of histone deacetylase1 (HDAC1) in signal transducer and activator of transcription 3 (STAT3) nucleocytoplasmic distribution", Nucleic Acids Res 36, 2008, 4510-4520.
Rubtsov, et al., "Regulatory T cell-derived interleukin-10 limits inflammation at environmental interfaces", Immunity 28, 2008, 546-558.
Santo, et al., "Preclinical activity, pharmacodynamic, and pharmacokinetic properties of a selective HDAC6i, ACY-1215, in combination with bortezomib in multiple myeloma", Blood 119(11), 2012, 2579-2589.
Saraiva, et al., "The regulation of IL-10 production by immune cells", Nat Rev Immunol. 10, 2010, 170-181.
Serrador, et al., "HDAC6 deacetylase activity links the tubulin cytoskeleton with immune synapse organization", Immunity 20, 2004, 417-428.
Sotomayor, et al., "Conversion of tumor-specific CD4+ T-cell tolerance to T-cell priming through in vivo ligation of CD40", Nat Med 5, 1999, 780-787.
Sotomayor, et al., "Role of tumor-derived cytokines on the immune system of mice bearing a mammary adenocarcinoma. II. Down-regulation of macrophage-mediated cytotoxicity by tumor-derived g ranulocyte-macrophage colony-stimulating factor", J Immunol 147, 1991, 2816-2823.
Staveley-O'Carroll, et al., "Induction of antigen-specific T cell energy: An early event in the course of tumor progression", Proc Natl Acad Sci USA 95, 1998, 1178-1183.
Togi, et al., "HDAC3 influences phosphorylation of STAT3 at serine 727 by interacting with PP2A", Biochem Biophys Res Commun 379, 2009, 616-620.
Toropainen, et al., "The Down-regulation of the Human MYC Gene by the Nuclear Hormone 1 [alpha],25-dihydroxyvitamin D3 is Associated with Cycling of Corepressors and Histone Deacetylases", J Mol Biol 400, 2010, 284-294.
Uesato, et al., "Novel Histone Deacetylase Inhibitors: N-Hydroxycarboxamides Possesing a Terminal Bicyclic Aryl Group", Bioorg & Med Chem Lett 12, 2002, 1347-1349.
Valenzuela-Fernandez, et al., "HDAC6: a key regulator of cytoskeleton, cell migration and cell-cell interactions", Trends in Cell Biology 18, 2008, 291-297.
Verdel, et al., "Active maintenance of mHDA2/mHDAC6 histone-deacetylase in the cytoplasm", Curr Biol 10, 2000, 747-749.
Vickers, et al., "Discovery of HDAC Inhibitors That Lack an Active Site Zn2+-Binding Functional Group", ACS Med Chem Lett 3(6), 2012, 505-508.
Villagra, et al., "Chromatin Remodeling and Transcriptional Activity of the Bone-specific Osteocalcin Gene Require CCAAT/Enhancer-binding Protein beta-dependent Recruitment of SWI/SNF Activity", J. Biol. Chem. 281, 2006, 22695-22706.
Villagra, et al., "The histone deacetylase HDAC11 regulates the expression of interleukin 10 and immune tolerance", Nat Immunol 10(1), 2009, 92-100.
Vicente-Suarez, et al., "Identification of a novel negative role of flagellin in regulating IL-10 production", Eur J Immunol 37, 2007, 3164-3175.
Wagner, et al., "Histone deacetylase (HDAC) inhibitors in recent clinical trials for cancer therapy", Clinical Epigenetics 1(3-4), 2010, 117-136.
Wakkach, et al., "Characterization of dendritic cells that induce tolerance and T regulatory 1 cell differentiation in vivo", Immunity 18, 2003, 605-617.
Wang, et al., "Activation of Stat3 Sequence-specific DNA Binding and Transcription by p300/CREB-binding Protein-mediated Acetylation.", J Biol Chem 280, 2005, 11528-11534.
Wang, et al., "Histone Deacetylase Inhibitor LAQ824 Augments Inflammatory Responses in Macrophages through Transcriptional Regulation of IL-10", J Immunol 186(7), 2011, 3986-3996.
Woan, et al., "Modulation of antigen-presenting cells by HDAC inhibitors: implications in autoimmunity and cancer", Immunol Cell Biol 90, 2012, 55-65.
Yang, et al., "The Rpd3/Hda1 family of lysine deacetylases: from bacteria and yeast to mice and men", Nat Rev Mol Cell Biol. 9, 2008, 206-218.
Yuan, et al., "Stat3 Dimerization Regulated by Reversible Acetylation of a Single Lysine Residue", Science 307, 2005, 269-273.
Zhang, et al., "HDAC6 Modulates Cell Motility by Altering the Acetylation Level of Cortactin", Molecular Cell 27, 2007, 197-213.
Zhang, et al., "Mice lacking histone deacetylase 6 have hyperacetylated tubulin but are viable and develop normally", Mol Cell Biol 28(5), 2008, 1688-1701.
Zhou, et al., "Discovery of N-(2-aminophenyl)4- 4-pyridin-3-ylpyrimidin-2-ylamino)methyl benzamide (MGCD0103), an orally active histone deacetylase inhibitor", J Med Chem 51(14), 2008, 4072-4075.
Zou, et al., "Characterization of the two catalytic domains in histone deacetylase 6", Biochem Biophys Res Commun 341(1), 2006, 45-50.
Examination Report for AU2013230881 dated Oct. 7, 2016.
CAS RN 875521-20-3 Mar. 1, 2006.
CAS RN 875521-21-4 Mar. 1, 2006.
CAS RN 875521-23-6 Mar. 1, 2006.
Office Action for JP2014-561101 dated Nov. 2, 2016.
Office Action for U.S. Appl. No. 15/231,187, dated Dec. 12, 2016.
Non Final Office Action for U.S. Appl. No. 14/383,418 issued by the United States Patent office on, Sep. 8, 2015.
Notice of Allowance for U.S. Appl. No. 14/383,418 issued by the United States Patent office on, Apr. 25, 2016.

\* cited by examiner

HDACs are targets of
Histone Deacetylase Inhibitors (HDI)

HDIs:
- Structurally diverse compounds
- Target several HDACs
- Induce differentiation, cell cycle and growth arrest in cancer cells
- Successes and failures in clinical trials for cancer patients
- Emerging role as modulators of inflammation and antitumor immune responses.....

| | Class I | | | | Class IIa | | | | Class IIb | | Class IV |
|---|---|---|---|---|---|---|---|---|---|---|---|
| | 1 | 2 | 3 | 8 | 4 | 5 | 7 | 9 | 6 | 10 | 11 |
| TSA | ○ | ○ | ○ | ○ | ○ | ○ | ○ | ○ | ○ | ○ | ○ |
| SAHA (Vorinostat) | ○ | ○ | ○ | ○ | ○ | ○ | ○ | ○ | ○ | ○ | ○ |
| LAQ824 | ○ | ○ | ○ | ○ | ○ | ○ | ○ | ○ | ○ | ○ | ○ |
| LBH689 | ○ | ○ | ○ | ○ | ○ | ○ | ○ | ○ | ○ | ○ | ○ |
| PXD101 | ○ | ○ | ○ | ○ | ○ | ○ | ○ | ○ | ○ | ○ | ○ |
| VPA | ○ | ○ | ○ | ○ | | | | | | | |
| Butyrate | ○ | ○ | ○ | ○ | | | | | | | |
| Trapoxin | ○ | ○ | ○ | ○ | ○ | ○ | ○ | ○ | | | |
| Depsipeptide | ○ | ○ | ○ | | | | | | | | |
| Romidepsin | ○ | ○ | ○ | | | | | | | | |
| MS275 | ○ | ○ | ○ | | | | | | | | |
| MGCD0103 | ○ | ○ | ○ | | | | | | | | |
| SB-379872-A | | | | ○ | | | | | | | |
| Tubacin | | | | | | | | | ○ | | |
| ST-3-06 | | | | | | | | | ○ | ○ | |
| ST-2-92 | | | | | | | | | ○ | ○ | |
| Tubestatin A | | | | | | | | | ○ | ○ | |

FIG. 2

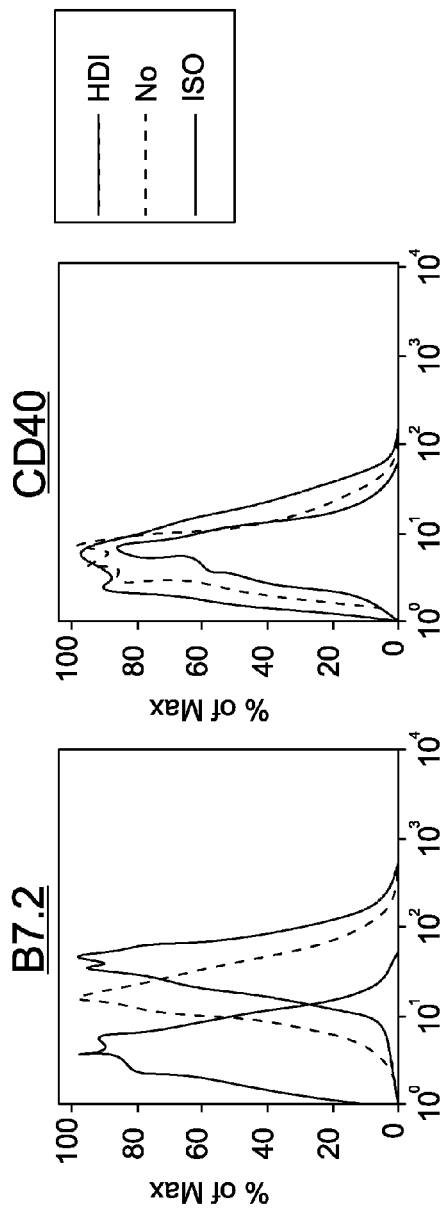
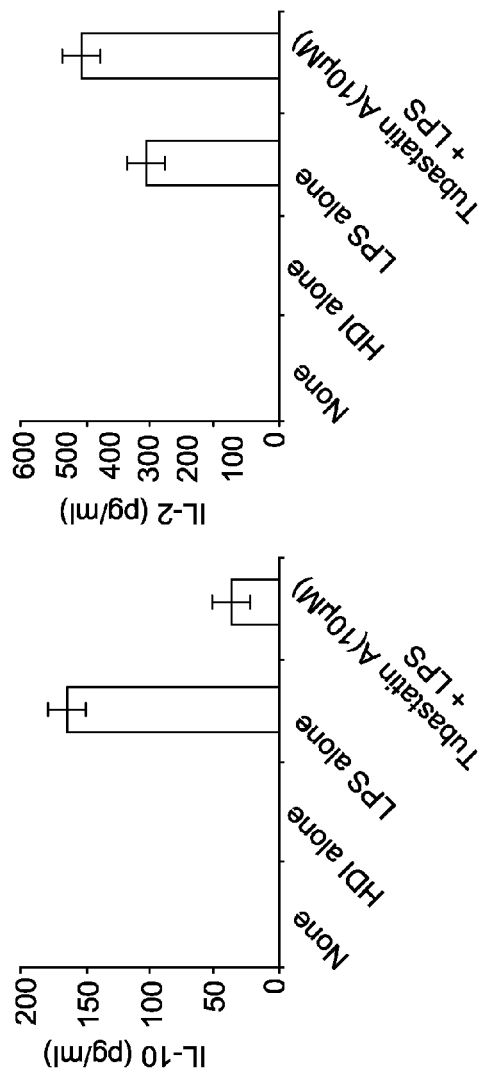
FIG. 23

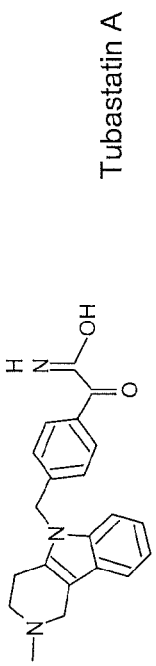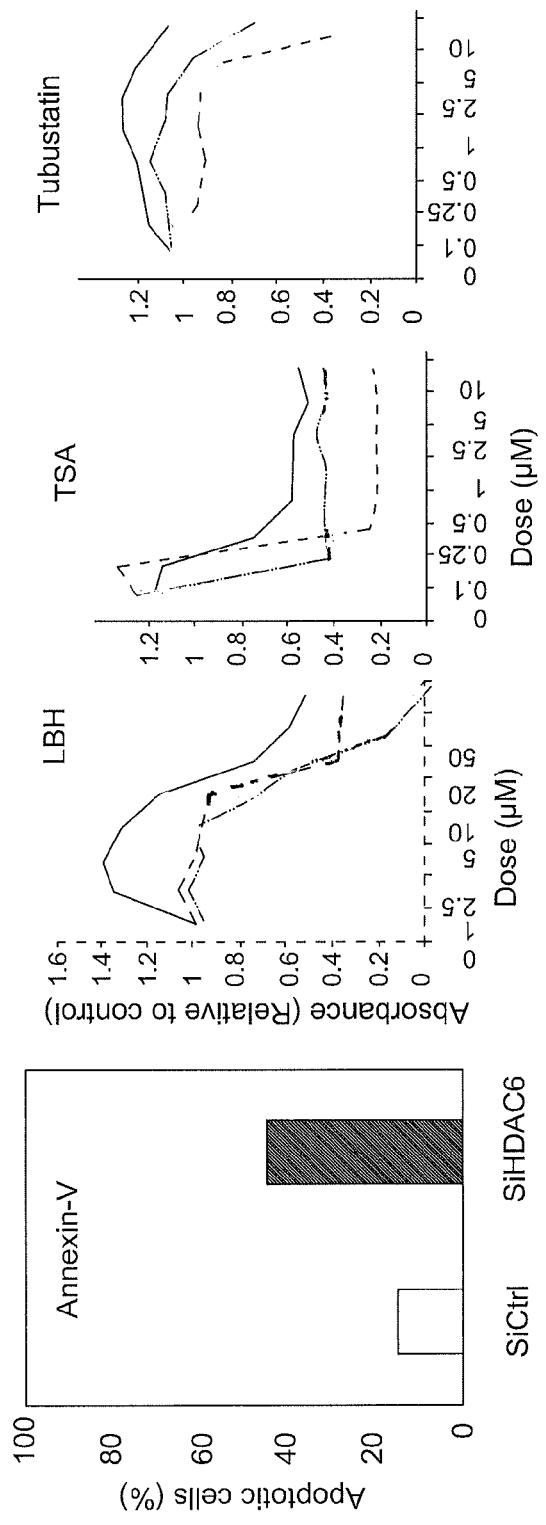
FIG. 30

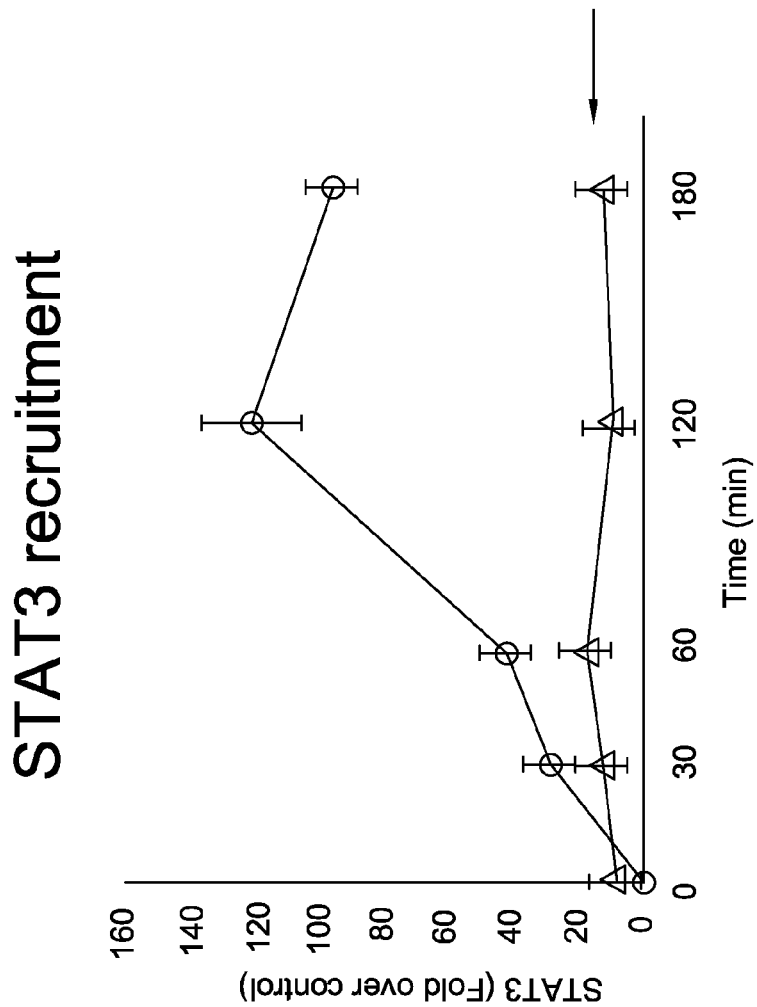
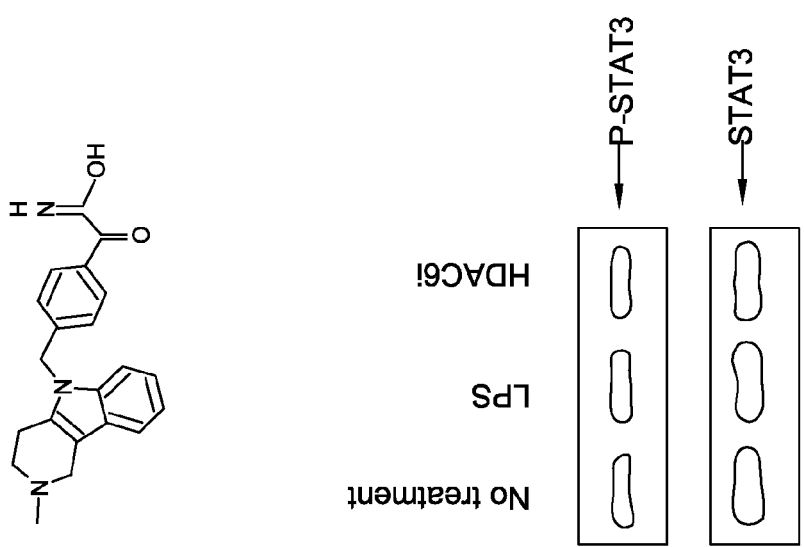
FIG. 37

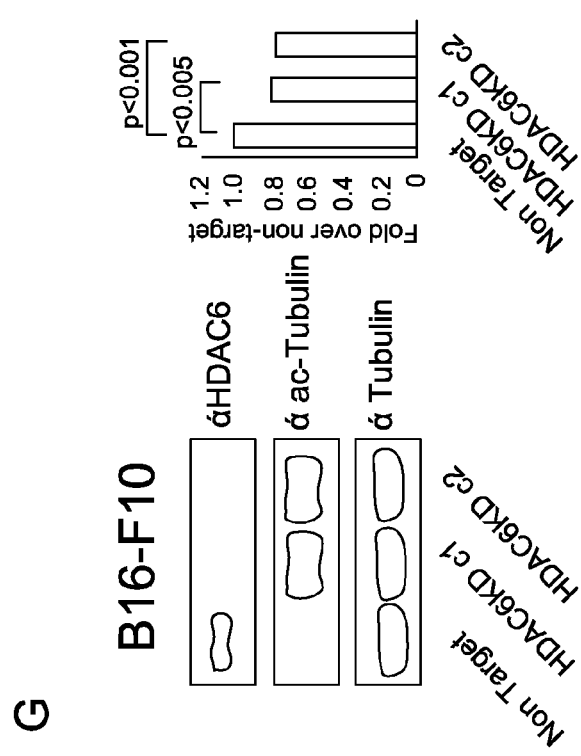
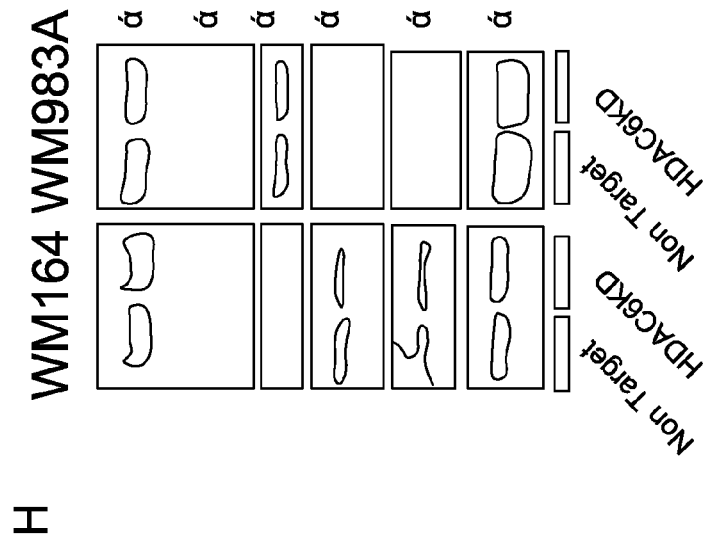
FIG. 42

SELECTIVE HISTONE DEACTYLASE 6 INHIBITORS

CROSS REFERENCE TO RELATED APPLICATIONS

This application claims the benefit of priority to U.S. Provisional Application 61/860,035, filed Jul. 30, 2013, which is incorporated by reference herein in its entirety.

ACKNOWLEDGEMENT OF GOVERNMENT SUPPORT

This invention was made with Government support under Grant No. CA134807 awarded by the National Institutes of Health. The Government has certain rights in the invention.

BACKGROUND

Epigenetic regulation and subsequent gene expression or silencing represents a tightly orchestrated interplay among enzymes responsible for modifying the tails of histones, around which nuclear DNA is wrapped. Among the various modifiers of the histones, the cell is capable of balancing the activity of both histone acetyltransferases (HAT) and histone deacetylases (HDAC) to attach or remove the acetyl group, respectively, from the lysine tails of these histone barrels. This particular epigenetic marker masks the positive lysine residues from interacting closely with the DNA phosphate-backbone, resulting in a more "open" chromatin state, whereas the deacetylases remove these acetyl groups, resulting in a more "closed" or compacted DNA-histone state.

There are currently no selective HDAC6 inhibitors (HDAC6i) approved for oncology purposes. Such molecules would be advantageous as a therapeutic approach for they can result in reduced side effects, which is an apparent problem associated with less selective HDACIs (Zhang et al., "Mice lacking histone deacetylase 6 have hyperacetylated tubulin but are viable and develop normally," *Mol Cell Biol* 2008, 28(5):1688-1701). Recent pre-clinical efforts are being directed toward the use of HDAC6i for certain cancers, specifically in combination with known drugs (Santo et al., "Preclinical activity, pharmacodynamic, and pharmacokinetic properties of a selective HDAC6i, ACY-1215, in combination with bortezomib in multiple myeloma," *Blood* 2012, 119(11):2579-2589). HDACIs can be useful as possible therapeutics for melanoma; however, studies to date have focused on using pan-HDACIs, such as suberoylanilide hydroxamic acid (SAHA) (Peltonen et al., "Melanoma cell lines are susceptible to histone deacetylase inhibitor TSA provoked cell cycle arrest and apoptosis," *Pigment Cell Res* 2005, 18(3):196-202; Facchetti et al., "Modulation of pro- and anti-apoptotic factors in human melanoma cells exposed to histone deacetylase inhibitors," *Apoptosis* 2004, 9(5):573-582). While SAHA exhibits activity against all Zn-dependant HDAC isozymes, it has been approved solely for the treatment of cutaneous T cell lymphoma (Wagner et al., "Histone deacetylase (HDAC) inhibitors in recent clinical trials for cancer therapy," *Clinical Epigenetics* 2010, 1(3-4):117-136). It has previously been reported that HDAC6 forms an association with HDAC11 (Gao et al., "Cloning and functional characterization of HDAC11, a novel member of the human histone deacetylase family," *J Biol Chem* 2002, 277(28):25748-25755). Recent efforts have begun to uncover the biological significance of HDAC11 as a participant in activating the immune response and targeting one or both of these enzymes is of therapeutic value (Villagra et al., "The histone deacetylase HDAC11 regulates the expression of interleukin 10 and immune tolerance," *Nat Immunol* 2009, 10(1):92-100; Wang et al., "Histone Deacetylase Inhibitor LAQ824 Augments Inflammatory Responses in Macrophages through Transcriptional Regulation of IL-10," *J Immunol* 2011, 186(7):3986-3996). Thus, HDAC6 has emerged as a target in the treatment of melanoma and other cancers. Such an approach can be devoid of the cytotoxic properties of the pan-HDACi's and thus of value in the context of safer cancer therapeutics (Parmigiani et al., "HDAC6 is a specific deacetylase of peroxiredoxins and is involved in redox regulation," *Proc Nat Acad Sci USA* 2008, 105(28):9633-9638). What are needed then are new and selective HDAC6 inhibitors and methods of making and using them to treat various cancers as well as to augment various tumor immune responses. The compositions and methods disclosed herein address these and other needs.

BRIEF DESCRIPTION OF FIGURES

The accompanying figures, which are incorporated in and constitute a part of this specification, illustrate several aspects described below.

FIG. 2 is an image depicting HDACs are targets for histone deacetylase inhibitors (HDACi).

FIG. 23 is a series of images depicting the immunological effects of Tubastatin A upon macrophages.

FIG. 30 is a series of images depicting the disruption of HDAC6 in human MCL cell lines.

FIG. 37 is a series of images depicting ST-3-06 decreased STAT3 phosphorylation and recruitment to the IL-10 gene promotor in APCs.

SUMMARY

Figure 1:
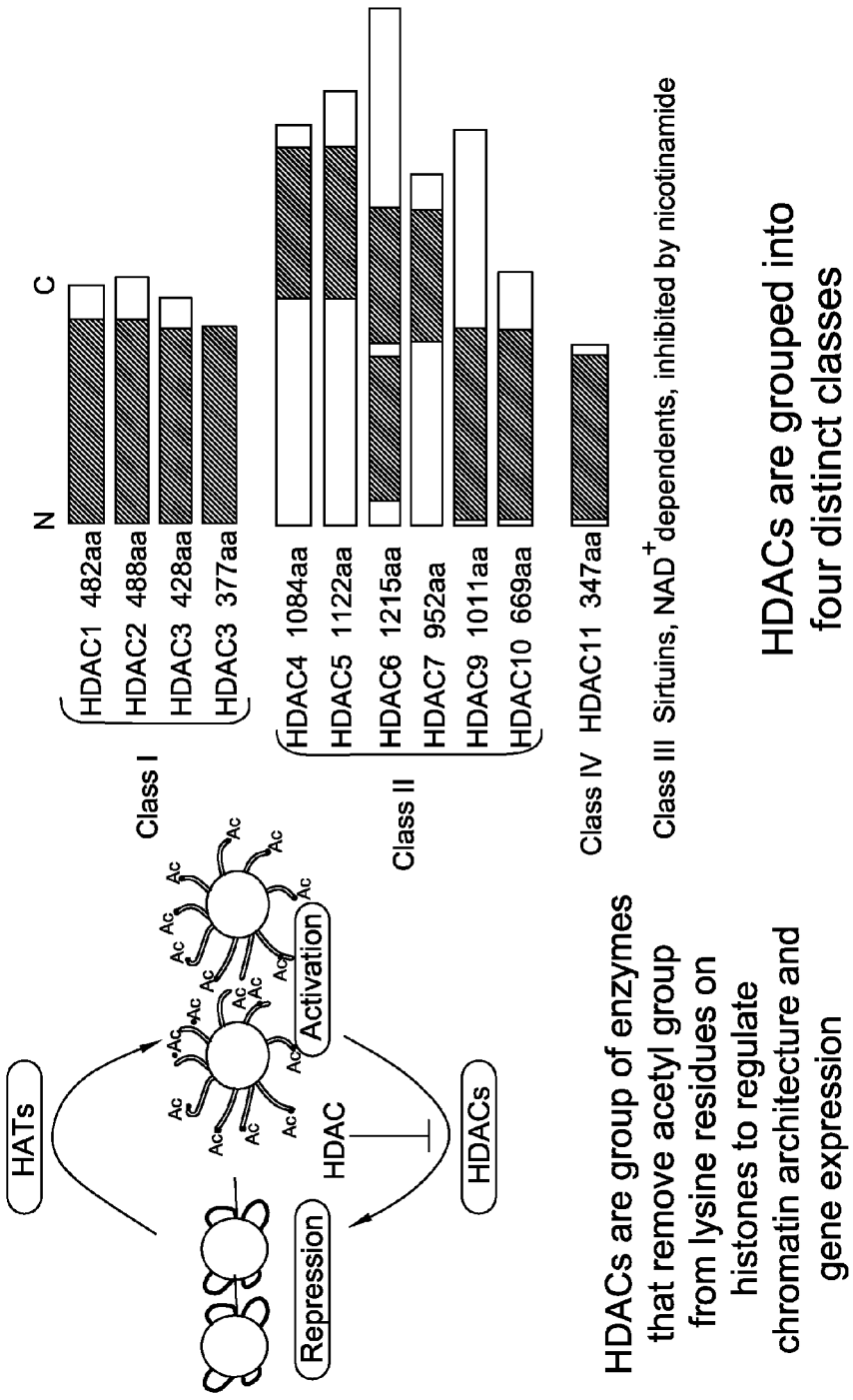
FIG. 1 is an image depicting the grouping of HDACs.

In accordance with the purposes of the disclosed materials, compounds, compositions, articles, devices, and methods, as embodied and broadly described herein, the disclosed subject matter relates to compositions and methods of making and using the compositions. In other aspects, the disclosed subject matter relates to compounds having activity as selective HDAC6 inhibitors, methods of making and using the compounds, and compositions comprising the compounds. In certain aspects, the disclosed subject matter relates to compounds having the chemical structure shown in Formulas I or II, in particular Formula I-A, I-B, and I-C, as defined herein. In still further aspects, the disclosed subject matter relates to methods for treating oncological disorders in a patient. For example, disclosed herein are methods whereby an effective amount of a compound or composition disclosed herein is administered to a patient having an oncological disorder, for example melanoma, and who is in need of treatment thereof. Methods of using the disclosed compounds to inhibit or kill tumor cells, to inhibit HDAC6, and to augment tumor inflammatory responses are also disclosed. Also disclosed are methods of using the disclosed compounds in combination with other cancer treatments. For example, the disclosed inhibitors of HDAC can be administered alone or in combination with a cancer immunotherapy agent. For example, the cancer immunotherapy agent can be an antibody that specifically binds CLTA-4, such as ipilimumab (Bristol-Myers Squibb).

Additional advantages of the disclosed subject matter will be set forth in part in the description that follows and the Figures, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

The materials, compounds, compositions, articles, and methods described herein may be understood more readily by reference to the following detailed description of specific aspects of the disclosed subject matter and the Examples and Figures included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat."

The term "anticancer" refers to the ability to treat or control cellular proliferation and/or tumor growth at any concentration.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as ($Z^1Z^2$)C=C($Z^3Z^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C=O, which is also referred to herein as a "carbonyl."

The terms "amine" or "amino" as used herein are represented by the formula —$NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —C(O)$NZ^1Z^2$.

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)$Z^1$ or —C(O)O$Z^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —$NO_2$.

The term "silyl" as used herein is represented by the formula —Si$Z^1Z^2Z^3$, where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2Z^1$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "thiol" as used herein is represented by the formula —SH.

The term "thio" as used herein is represented by the formula —S—.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are)

selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compounds

A variety of HDAC6 inhibitors have been investigated (Butler et al., "Rational Design and Simple Chemistry Yield a Superior, Neuroprotective HDAC6 Inhibitor, Tubastatin A," *J Am Chem Soc* 2010, 132(31):10842-10846; Kalin et al., "Second-Generation Histone Deacetylase 6 Inhibitors Enhance the Immunosuppressive Effects of Foxp3+ T-Regulatory Cells," *J Med Chem* 2012, 55(2):639-651). A feature of these agents is the presence of a benzylic linker that is built into a canonical inhibitor, which comprises a "cap-linker-zinc binding group" system. There is a report that discloses HDACi's without the zinc-binding group (ZBG) (Vickers et al., "Discovery of HDAC Inhibitors That Lack an Active Site $Zn^{2+}$-Binding Functional Group," *ACS Med Chem Lett* 2012, 3(6):505-508). These agents possessed modest activity against the Class 1 enzymes.

The compounds disclosed herein maintain a ZBG, most preferably a hydroxamic acid group. Further, the disclosed compounds contain certain urea-based cap groups that are incorporated into a benzyl hydroxamic acid scaffold, leading to potent and selective HDAC6 inhibitors with in vitro anti-melanoma activity. As such, disclosed herein are compounds having Formula I:

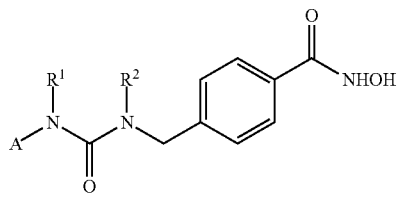

I wherein

A is aryl, heteroaryl, or $C_1$-$C_8$ alkyl, any of which is optionally substituted with one or more groups chosen from acetyl, $C_1$-$C_5$ alkyl, amino, —$NR^6R^7$, —C(O)$NR^6R^7$, $C_1$-$C_4$ alkoxy, $C_1$-$C_4$ alkylhydroxy, $C_5$-$C_6$ cycloalkyl, $C_5$-$C_6$ heterocycloalkyl, aryl, heteroaryl, halo, hydroxy, thiol, cyano, or nitro; and $R^1$ and $R^2$ are independently chosen from hydrogen, $C_1$-$C_8$ alkyl, $C_1$-$C_8$ alkenyl, $C_1$-$C_8$ alkynyl, $C_1$-$C_8$ haloalkyl, $C_5$-$C_6$ cycloalkyl, $C_5$-$C_6$ heterocycloalkyl, $C_1$-$C_3$ alkylaryl, aryl, $C_1$-$C_3$ alkylheteroaryl, or heteroaryl, any of which is optionally substituted with acetyl, $C_1$-$C_5$ alkyl, amino, —$NR^6R^7$, —C(O)$NR^6R^7$, $C_1$-$C_4$ alkoxy, $C_1$-$C_4$ alkylhydroxy, $C_5$-$C_6$ cycloalkyl, $C_5$-$C_6$ heterocycloalkyl, aryl, heteroaryl, carbonyl, halo, hydroxy, thiol, cyano, or nitro; or $R^1$ and $R^2$ are joined such that together they form an alkylene bridge comprising 2 atoms so that a 5-membered ring is formed with the —NC(O)N— moiety, in which case A is as defined above or hydrogen, and which 5-membered ring is optionally substituted with $R^{1'}$, $R^{2'}$, $R^{1''}$, and $R^{2''}$, which are independently, hydrogen, or are $C_1$-$C_8$ alkyl, $C_5$-$C_6$ cycloalkyl, $C_5$-$C_6$ heterocycloalkyl, $C_1$-$C_3$ alkylaryl, aryl, $C_1$-$C_3$ alkylheteroaryl, or heteroaryl any of which is optionally substituted with amino, aryl, $C_1$-$C_4$ alkoxy, halo, or hydroxy; or $R^{1'}$ and $R^{1''}$ together or $R^{2''}$ and $R^{2'}$ together form a carbonyl (i.e., =O); or $R^{1'}$ and $R^{2'}$ are null and $R^{1''}$ and $R^{2''}$ together form a fused phenyl group; and $R^6$ and $R^7$ are independently H, $C_1$-$C_4$ alkyl, or are joined such that together they form an alkylene bridge comprising 4 or 5 atoms so that a 5 or 6-membered ring is formed with the nitrogen;

or a pharmaceutically acceptable salt or hydrate thereof. In some examples, when $R^1$ and $R^2$ are both hydrogen, A is not hydroxyphenyl.

In specific examples, A can be a phenyl, pyridyl, oxazolidyl, or pyrimidyl optionally substituted with $C_1$-$C_5$ alkyl, amino, alkoxy, alkylhydroxy, halo, hydroxy, or thiol. In still other examples, A can be phenyl or phenyl substituted with $C_1$-$C_5$ alkyl, $C_1$-$C_4$ alkoxyl, or halo. In still other example, A can be pyridyl or pyridyl substituted with $C_1$-$C_5$ alkyl, $C_1$-$C_4$ alkoxyl, or halo. In a preferred example, A is phenyl, or methoxyl substituted phenyl, or halo substituted phenyl. In further examples, A can be a phenyl. In still further examples, A can be a phenyl substituted with one or more methoxyl, ethoxyl, or propoxyl groups, for example, A can be a phenyl substituted with one methoxyl group at the ortho-, para-, or meta-position. In a most preferred example, A can be a phenyl substituted with a methoxyl group at the ortho-position. Still further, A can be a phenyl substituted with one or more halo groups, for example, A can be a phenyl with one halo (e.g., Cl, Br, or F) group at the ortho-, para-, or meta-position. In other examples, A can be a phenyl group with one or more carboxylic acids group or an alkyl ester group (e.g., an acetyl group). A can be a $C_1$-$C_8$ alkyl group. In still other examples, A can be a phenyl substituted with one or more $C_1$-$C_4$ alkyl groups. A can be a phenyl substituted with one methyl, ethyl, n-propyl, i-propyl, n-butyl, t-butyl, s-butyl, i-butyl group at the ortho-, para-, or meta-position. A can be a phenyl substituted with one or more $NH_2$ or $N(C_1$-$C_4)_2$ groups, such as $N(CH_3)_2$.

In some examples A can be a heteroaryl. For example, A can be a heteraryl selected from 2-furyl, 3-furyl, 2-thienyl, 3-thienyl, 1-pyrrolyl, 2-pyrrolyl, 3-pyrrolyl, 1-imidazolyl, 2-imidazolyl, 4-imidazolyl, 5-imidazolyl, 1-pyrrolyl, 3-pyrazolyl, 4-pyrazolyl, 5-pyrazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 2-pyridyl, 3-pyridyl, 4-pyridyl, 2-pyrimidyl, A-pyrimidyl, 5-pyrmidinyl, 6-pyrimidinyl, 1,2,3-triazol-1-yl, 1,2,3-triazol-4-yl, or 1,2,3-triazol-5-yl, 1,2,4-triazol-1-yl, 1,2,4-triazol-3-yl, 1,2,4-triazol-5-yl, 1-tetrazolyl, 5-tetrazolyl, 1,2,3-oxadiazol-4-yl, 1,2,3-oxadiazol-5-yl, 1,2,4-oxadiazol-3-yl, 1,2,4-oxadiazol-5-yl, 1,3,4-thiadiazol-2-yl or 1,3,4-thiadiazol-5-yl, 1,2,4-thiadiazol-3-yl, or 1,2,4-thiadiazol-3-5-yl, 1,2,3-thiadiazol-4-yl, 1,2,3-thiadiazol-5-yl, 3-pyridazinyl, A-pyridazinyl, pyrazinyl, 1-indolyl, 2-indolyl, 3-indolyl, 4-indolyl, 5-indolyl, 6-indolyl, 7-indolyl, 4-isoindolyl, 5-isoindolyl, 1-benzimidazolyl, 2-benzimidazolyl, A-benzimidazolyl, 5-benzimidazolyl, 1-benzopyrazolyl, 3-benzopyrazolyl, A-benzopyrazolyl, 5-benzopyrazolyl, 6-benzopyrazolyl, 7-benzopyrazolyl, 2-benzoxazolyl, 4-benzoxazolyl, 5-benzoxazolyl, 6-benzoxazolyl, 7-benzoxazolyl, 3-benzisoxazolyl, 4-benzisoxazolyl, 5-benzisoxazolyl, 6-benzisoxazolyl, 7-benzisoxazolyl, 2-benzothiazolyl, 4-benzothiazolyl, 5-benzothiazolyl, 6-benzothiazolyl, 7-benzothiazolyl, 2-benzisothiazolyl, 4-benzisothiazolyl, 5-benzisothiazolyl, 6-benzisothiazolyl, 7-benzisothiazolyl, 4-benz-2,1,3-oxadiazolyl, 5-benz-2,1,3-oxadiazolyl, 6-benz-2,1,3-oxadiazolyl, 7-benz-2,1,3-oxadiazolyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 3-cinnolinyl, 4-cinnolinyl, 5-cinnolinyl, 6-cinnolinyl, 7-cinnolinyl, 8-cinnolinyl, 2-quinazolinyl, 4-quinazolinyl, 5-quinazolinyl, 6-quinazolinyl, 7-quinazolinyl, 8-quinazolinyl, 5-quinoxalinyl, 6-quinoxalinyl, 2-2H-benz-1,4-oxazinyl, 3-2H-benz-1,4-oxazinyl, 5-2H-benz-1,4-oxazinyl, 6-2H-benz-1,4-oxazinyl, 7-2H-benz-1,4-oxazinyl, 8-2H-benz-1,4-oxazinyl, 1,3-benzodioxol-5-yl, 1,4-benzodioxan-6-yl, 2,1,3-benzothiadiazol-4-yl, 2,1,3-benzothiadiazol-5-yl, and 2,1,3-benzoxadiazol-5-yl.

In some other examples, A can be a heterary selected from 2,3-dihydro-2-furyl, 2,3-dihydro-3-furyl, 2,3-dihydro-4-furyl, 2,3-dihydro-5-furyl, 2,5-dihydro-2-furyl, 2,5-dihydro-3-furyl, 2,5-dihydro-4-furyl, 2,5-dihydro-5-furyl, tetrahydro-2-furyl, tetrahydro-3-furyl, 1,3-dioxolan-4-yl, tetrahydro-2-thienyl, tetrahydro-3-thienyl, 2,3-dihydro-1-pyrrolyl, 2,3-dihydro-2-pyrrolyl, 2,3-dihydro-3-pyrrolyl, 2,3-dihydro-4-pyrrolyl, 2,3-dihydro-5-pyrrolyl, 2,5-dihydro-1-pyrrolyl, 2,5-dihydro-2-pyrrolyl, 2,5-dihydro-3-pyrrolyl, 2,5-dihydro-4-pyrrolyl, 2,5-dihydro-5-pyrrolyl, 1-pyrrolidinyl, 2-pyrrolidinyl, 3-pyrrolidinyl, tetrahydro-1-imidazolyl, tetrahydro-2-imidazolyl, tetrahydro-4-imidazolyl, 2,3-dihydro-1-pyrazolyl, 2,3-dihydro-2-pyrazolyl, 2,3-dihydro-3-pyrazolyl, 2,3-dihydro-4-pyrazolyl, 2,3-dihydro-5-pyrazolyl, tetrahydro-1-pyrazolyl, tetrahydro-3-pyrazolyl, tetrahydro-4-pyrazolyl, 1,4-dihydro-1-pyridyl, 1,4-dihydro-2-pyridyl, 1,4-dihydro-3-pyridyl, 1,4-dihydro-4-pyridyl, 1,2,3,4-tetrahydro-1-, 1,2,3,4-tetrahydro-2-, 1,2,3,4-tetrahydro-3-pyridyl, 1,2,3,4-tetrahydro-4-pyridyl, 1,2,3,4-tetrahydro-5-pyridyl, 1,2,3,4-tetrahydro-6-pyridyl, 1-piperidinyl, 2-piperidinyl, 3-piperidinyl, 4-piperidinyl, 2-morpholinyl, 3-morpholinyl, 4-morpholinyl, tetrahydro-2-pyranyl, tetrahydro-3-pyranyl, tetrahydro-4-pyranyl, 1,4-dioxanyl, 1,3-dioxan-2-yl, 1,3-dioxan-4-yl, 1,3-dioxan-5-yl, hexahydro-1-pyridazinyl, hexahydro-3-pyridazinyl, hexahydro-4-pyridazinyl, hexahydro-1-pyrimidinyl, hexahydro-2-pyrimidinyl, hexahydro-4-pyrimidinyl, hexahydro-5-pyrimidinyl, 1-piperazinyl, 2-piperazinyl, 3-piperazinyl, 1,2,3,4-tetrahydro-1-, 1,2,3,4-tetrahydro-2-quinolyl, 1,2,3,4-tetrahydro-3-quinolyl, 1,2,3,4-tetrahydro-4-quinolyl, 1,2,3,4-tetrahydro-5-quinolyl, 1,2,3,4-tetrahydro-6-quinolyl, 1,2,3,4-tetrahydro-7-quinolyl, 1,2,3,4-tetrahydro-8-quinolyl, 1,2,3,4-tetrahydro-1-isoquinolyl, 1,2,3,4-tetrahydro-2-isoquinolyl, 1,2,3,4-tetrahydro-3-isoquinolyl, 1,2,3,4-tetrahydro-4-isoquinolyl, 1,2,3,4-tetrahydro-5-isoquinolyl, 1,2,3,4-tetrahydro-6-isoquinolyl, 1,2,3,4-tetrahydro-7-isoquinolyl, 1,2,3,4-tetrahydro-8-isoquinolyl, 2-3,4-dihydro-2H-benzo-1,4-oxazinyl, 3-3,4-dihydro-2H-benzo-1,4-oxazinyl, 5-3,4-dihydro-2H-benzo-1,4-oxazinyl, 6-3,4-dihydro-2H-benzo-1,4-oxazinyl, 7-3,4-dihydro-2H-benzo-1,4-oxazinyl, 8-3,4-dihydro-2H-benzo-1,4-oxazinyl, 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofiiran-5-yl, 2,3-dihydrobenzofuran-6-yl, 2,3-(2-oxomethylenedioxy)phenyl, 3,4-dihydro-2H-1,5-benzodioxepin-6-yl, 3,4-dihydro-2H-1,5-benzodioxepin-7-yl, 2,3-dihydrobenzofltranyl, or 2,3-dihydro-2-oxofuranyl.

In certain specific examples A can be a substituted or unsubstituted pyrimidine or A can be a substituted or unsubstituted 1H-indazole.

In other examples, A can be a n-propyl, i-propyl, n-butyl, t-butyl, s-butyl, i-butyl, n-pentyl, i-pentyl, or s-pentyl group.

In specific examples, $R^1$ can be hydrogen, $C_1$-$C_8$ alkyl, $C_5$-$C_6$ cycloalkyl, $C_5$-$C_6$ heterocycloalkyl, aryl, or heteroaryl, any of which is optionally substituted with $C_1$-$C_3$ alkyl, amino, —$NR^6R^7$, $C_1$-$C_4$ alkoxy, $C_1$-$C_4$ alkylhydroxy, carbonyl, hydroxy, thiol, or cyano. In specific examples, $R^1$ can be $C_1$-$C_8$ alkyl, for example a $C_1$-$C_4$ alkyl. In other examples, $R^1$ can be a $C_1$-$C_8$ alkyl which is optionally substituted with acetyl, $NH_2$, $N(C_1$-$C_4)_2$ $C_1$-$C_4$ alkoxy, $C_1$-$C_4$ $C_5$-$C_6$ heterocycloalkyl, carbonyl, halo, or hydroxy. In preferred examples, $R^1$ is hydrogen.

In specific examples, $R^2$ can be hydrogen, $C_1$-$C_8$ alkyl, $C_5$-$C_6$ cycloalkyl, $C_5$-$C_6$ heterocycloalkyl, aryl, or heteroaryl, any of which is optionally substituted with $C_1$-$C_5$ alkyl, amino, —$NR^6R^7$, $C_1$-$C_4$ alkoxy, $C_1$-$C_4$ alkylhydroxy, carbonyl, hydroxy, thiol, or cyano. In specific examples, $R^2$ can be $C_1$-$C_5$ alkyl, or $C_1$-$C_5$ alkyl substituted with a methoxy, amino, —$NR^6R^7$, alkylhydroxy, carbonyl, hydroxy, cyano. In other examples, $R^2$ can be a $C_1$-$C_4$ alkyl substituted with a heteroaryl, such as imidazole or indole. In other examples $R^2$ can be a $C_1$-$C_4$ alkyl substituted with a phenyl, hydroxy substituted phenyl, methoxy substituted phenyl, halo substituted phenyl, or amino substituted phenyl. In preferred examples, $R^2$ is butyl.

In further examples, the disclosed compounds can have Formula I-A

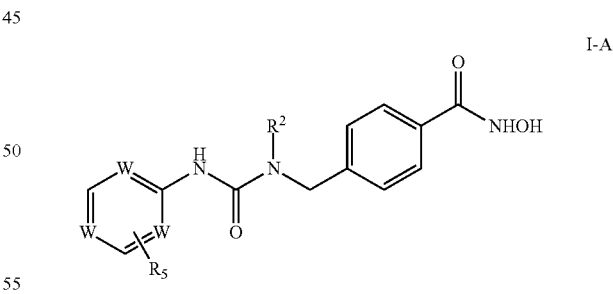

I-A where $R^2$ is as noted herein; each W is independent of the others CH or N; and $R^5$ is hydrogen, $C_1$-$C_8$ alkyl, $C_1$-$C_8$ alkenyl, $C_1$-$C_8$ alkynyl, $C_1$-$C_8$ haloalkyl, $C_5$-$C_6$ cycloalkyl, $C_5$-$C_6$ heterocycloalkyl, aryl, or heteroaryl, any of which is optionally substituted with acetyl, $C_1$-$C_5$ alkyl, amino, —$NR^6R^7$, —$C(O)NR^6R^7$, $C_1$-$C_4$ alkoxy, $C_1$-$C_4$ alkylhydroxy, $C_5$-$C_6$ cycloalkyl, $C_5$-$C_6$ heterocycloalkyl, aryl, heteroaryl, carbonyl, halo, hydroxy, thiol, cyano, or nitro, or a pharmaceutically acceptable salt or hydrate thereof.

In further examples, the disclosed compounds can have Formula I-B

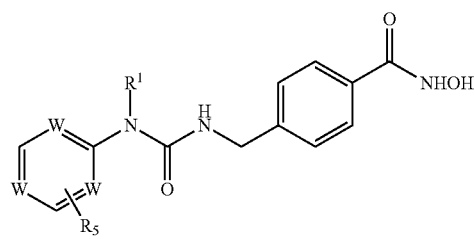

where R[1] is as noted herein; each W is independent of the others CH or N; and R[5] is hydrogen, $C_1$-$C_8$ alkyl, $C_1$-$C_8$ alkenyl, $C_1$-$C_8$ alkynyl, $C_1$-$C_8$ haloalkyl, $C_5$-$C_6$ cycloalkyl, $C_5$-$C_6$ heterocycloalkyl, aryl, or heteroaryl, any of which is optionally substituted with acetyl, $C_1$-$C_5$ alkyl, amino, —NR[6]R[7], —C(O)NR[6]R[7], $C_1$-$C_4$ alkoxy, $C_1$-$C_4$ alkylhydroxy, $C_5$-$C_6$ cycloalkyl, $C_5$-$C_6$ heterocycloalkyl, aryl, heteroaryl, carbonyl, halo, hydroxy, thiol, cyano, or nitro, or a pharmaceutically acceptable salt or hydrate thereof.

The disclosed compounds can be selective HDAC6i's. A homology model (Butler et al., *J Am Chem Soc* 2010, 132(30:10842-10846) shows the entrance to the binding site is wider and shallower for HDAC6 than that of HDAC1. This model also shows a lipophillic cavity. As such, the disclosed compounds can contain certain branched-elements incorporated into the aryl urea cap group, primarily at A, R[1] and/or R[2], to enhance both the potency and selectivity by accessing this side cavity and leading to better interactions with the surface of HDAC6.

Accessing this side cavity can be, in one aspect, accomplished through substituting the proximal nitrogen atom of the urea linker relative to the benzyl linker, i.e., R[2] in Formula I. The synthesis of these branched acyclic ureas is accomplished as outlined in Scheme 1. As an example, a variety of amines undergo reductive amination with methyl 4-formylbenzoate 2 to form the desired secondary amines 3a-h. Subsequent reaction of 3a-h with the appropriate isocyanates affords the branched urea esters 4a-h. Aryl isocyanates are shown in Scheme 1; however, other isocyanates can be used to vary the "A" group in Formula I (e.g., heteroaryl, or alkyl). This chemistry generates a series of ureas displaying branched substitutions on the nitrogen proximal to the benzylic linker (R[2]). The hydroxamic acid group is installed using hydroxylamine under basic conditions to provide the hydroxamic acids 5a-h.

Scheme 1: Synthesis of proximal N-substituted hydroxamic acids

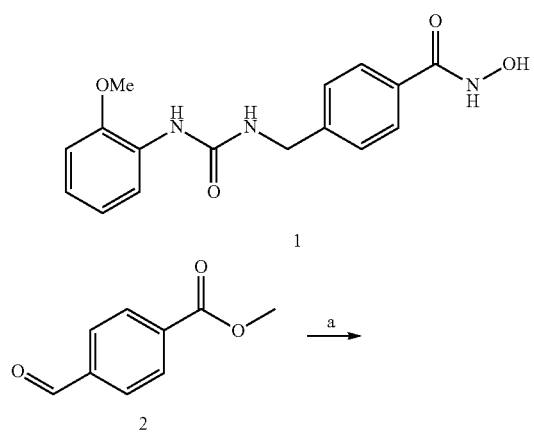

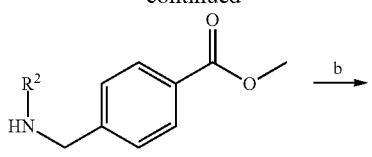

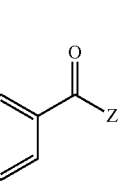

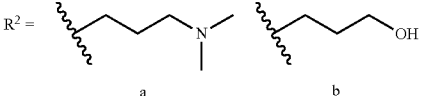

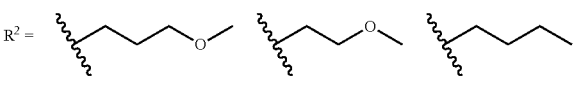

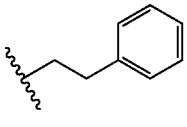

Reagents and conditions: (a) R[2]—NH$_2$, NaCNBH$_3$, rt, 5% AcOH/DCM, 16 h; (b) Aryl-NCO, DCM, rt, 16 h; (c) 50% wt NH$_2$OH, NaOH, THF/MEOH (1:1), 0° C. to rt, 30 min.

Accessing this side cavity can be, in another aspect, accomplished through substituting the distal nitrogen atom of the urea linker relative to the benzyl linker, i.e., R[1] in Formula I. The synthesis of these branched acyclic ureas is accomplished as outlined in Scheme 2. As an example, a copper-mediated Buchwald coupling reaction is used in order to assemble anilines 6a-b from iodobenzene, as these intermediates are not commercially available (Kwong et al., "Copper-catalyzed coupling of alkylamines and aryl iodides: An efficient system even in an air atmosphere" *Org Lett* 2002, 4(4):581-584). Triphosgene chemistry is implemented to convert methyl 4-(aminomethyl)benzoate into the corresponding isocyanate, which undergoes reaction with secondary amines 6a-c to afford the penultimate esters 7a-c. Final conversion to the hydroxamic acids is accomplished as in Scheme 1 to complete the synthesis of 8a-c.

Scheme 2: Synthesis of distal N-substituted hydroxamic acids
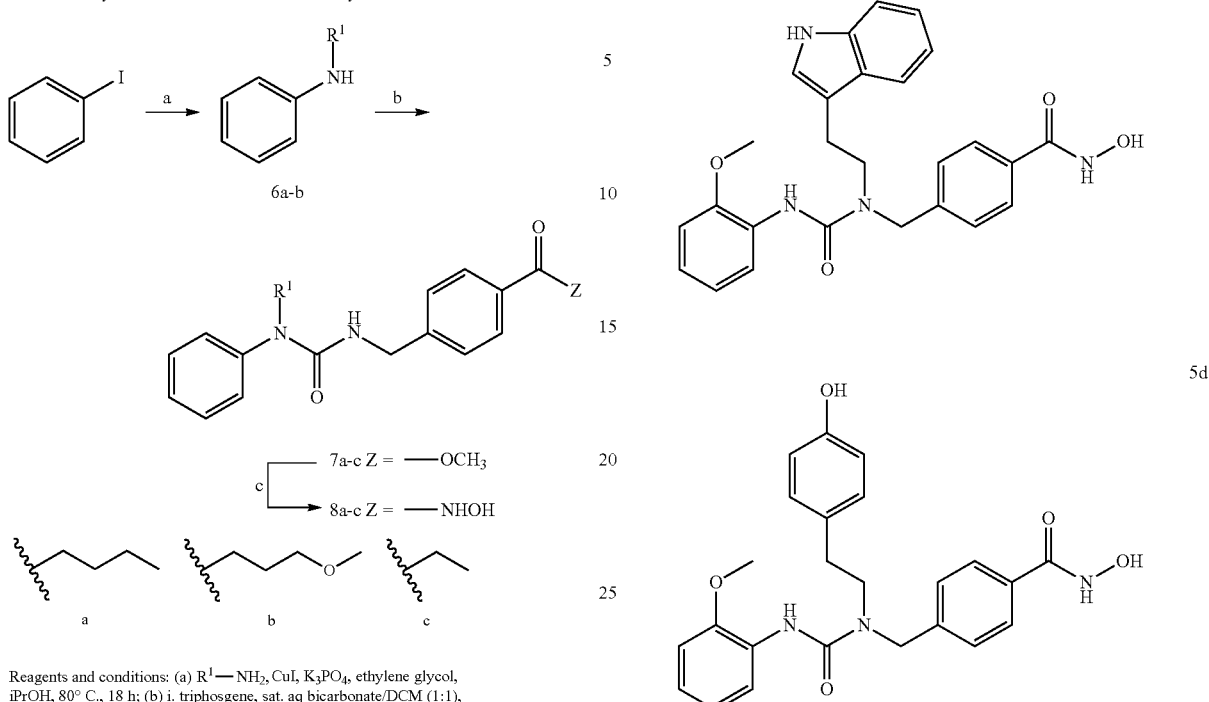
Reagents and conditions: (a) R¹—NH₂, CuI, K₃PO₄, ethylene glycol, iPrOH, 80° C., 18 h; (b) i. triphosgene, sat. aq bicarbonate/DCM (1:1), 0° C., 30 min; ii. methyl 4-(aminomethyl)benzoate-HCl, Et₃N, DCM, rt, 16 h; (c) 50% wt NH₂OH, NaOH, THF/MeOH (1:1), 0° C. to rt, 30 min.
Specific compounds according to Formula I are as follows.
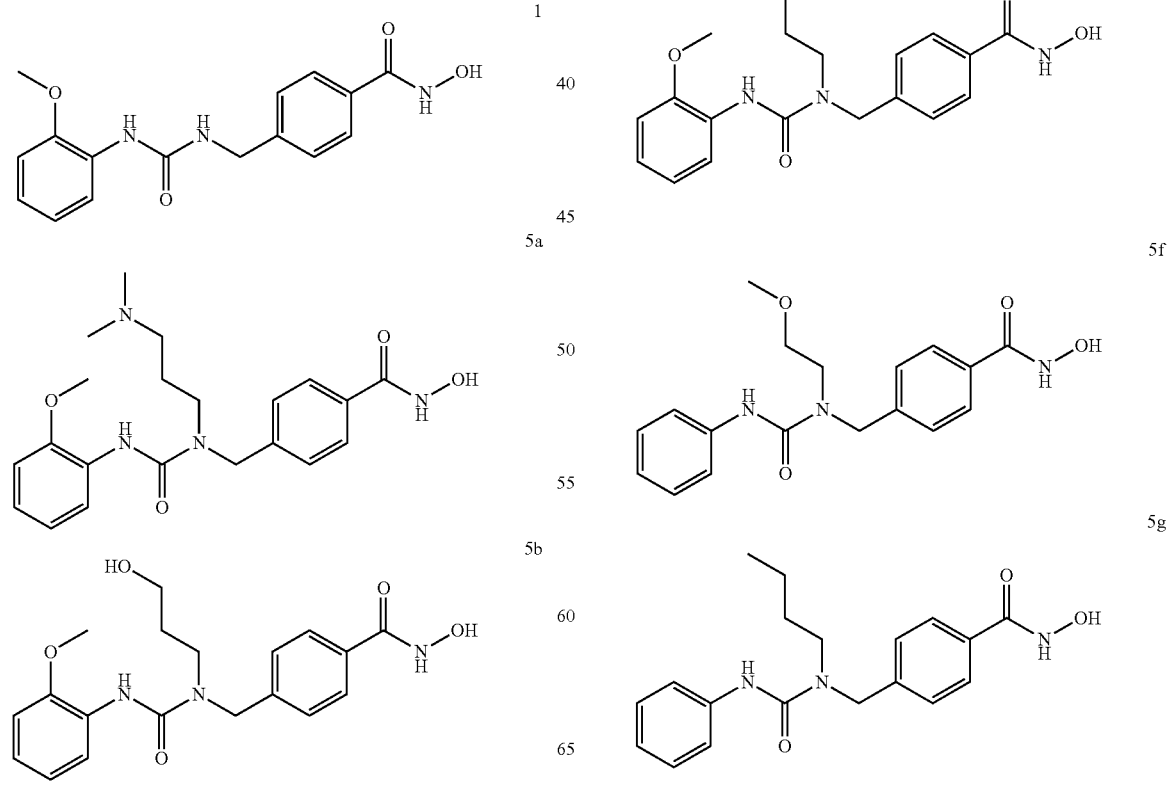

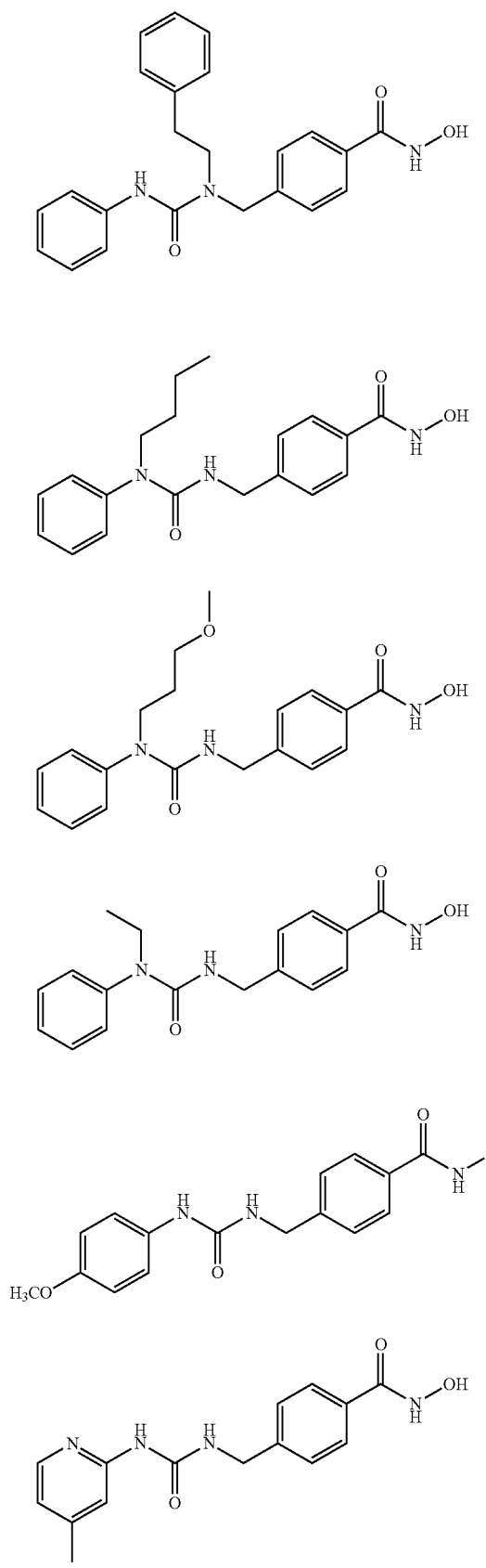
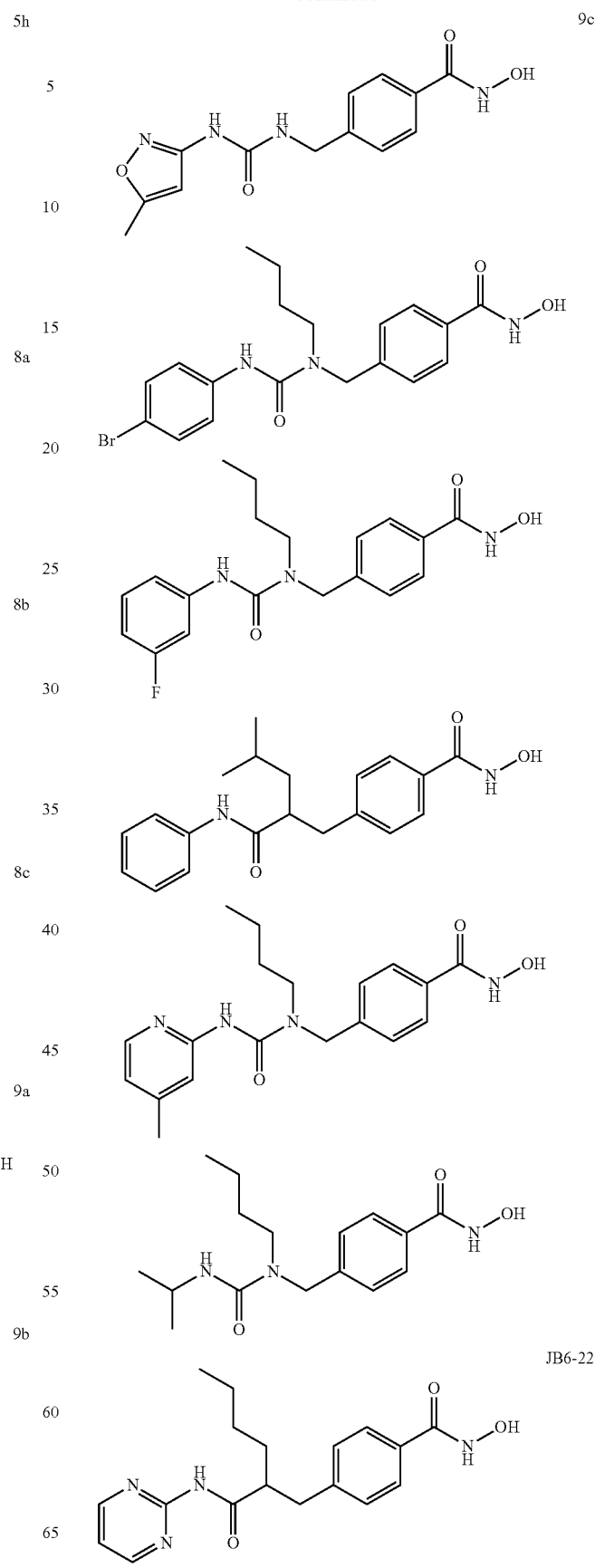

-continued

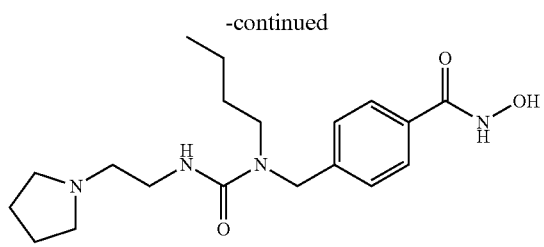

JB7-20

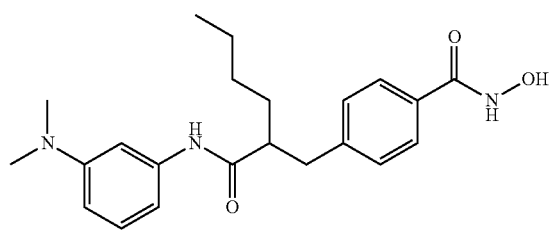

JB7-19

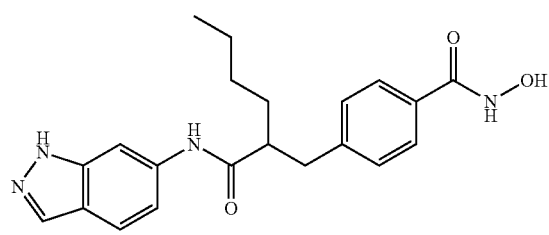

or pharmaceutically acceptable salts or hydrates thereof.

Accessing the side cavity of HDAC6 can also be, in still another aspect, accomplished through linking the distal and proximal nitrogen atoms of the urea linker via an alkylene bridge, i.e., joining $R^1$ and $R^2$ together to form a 5-membered ring with the
—NC(O)N— moiety in Formula I. Thus, in further examples the disclosed compounds can have Formula I-C

I-C wherein
A is hydrogen, or A is aryl, heteroaryl, or $C_1$-$C_8$ alkyl, any of which is optionally substituted with one or more groups chosen from acetyl, $C_1$-$C_5$ alkyl, amino, —$NR^6R^7$, —C(O)$NR^6R^7$, $C_1$-$C_4$ alkoxy, $C_1$-$C_4$ alkylhydroxy, $C_5$-$C_6$ cycloalkyl, $C_5$-$C_6$ heterocycloalkyl, aryl, heteroaryl, halo, hydroxy, thiol, cyano, or nitro, with $R^6$ and $R^7$ as defined above; and
$R^{1'}$, $R^{2'}$, $R^{1'''}$, and $R^{2'''}$, are independently, hydrogen, or are $C_1$-$C_8$ alkyl, $C_5$-$C_6$ cycloalkyl, $C_5$-$C_6$ heterocycloalkyl, $C_1$-$C_3$ alkylaryl, aryl, $C_1$-$C_3$ alkylheteroaryl, or heteroaryl any of which is optionally substituted with amino, aryl, $C_1$-$C_4$ alkoxy, halo, or hydroxy; or $R^{1'}$ and $R^{1'''}$ together or $R^{2'''}$ and $R^{2'}$ together form a carbonyl (i.e., =O); or $R^{1'}$ and $R^{2'}$ are null and $R^{1'''}$ and $R^{2'''}$ together form a fused phenyl group.

In certain examples, $R^{2'}$ and $R^{2'''}$ are both methyl. In other examples $R^{2'}$ is hydrogen and $R^{2'''}$ is methyl, ethyl, propyl, i-propyl, n-butyl, i-butyl, benzyl, tosyl, hydroxyphenyl, $C_1$-$C_4$ alkoxyphenyl, or aminophenyl. In other examples $R^{2'}$ and $R^{2'''}$ form a carboxyl (i.e., =O) group, or a pharmaceutically acceptable salt or hydrate thereof.

In certain examples, $R^{1'}$ and $R^{1'''}$ are both methyl. In other examples $R^{1'}$ is hydrogen and $R^{1'''}$ is methyl, ethyl, propyl, i-propyl, n-butyl, i-butyl, benzyl, tosyl, hydroxyphenyl, $C_1$-$C_4$ alkoxyphenyl, or aminophenyl. In other examples $R^{1'}$ and $R^{1'''}$ form a carboxyl (i.e., =O) group.

The synthesis of these cyclic ureas is accomplished as outlined in Scheme 3.

Scheme 3: Synthesis of cyclic urea hydroxamic acids

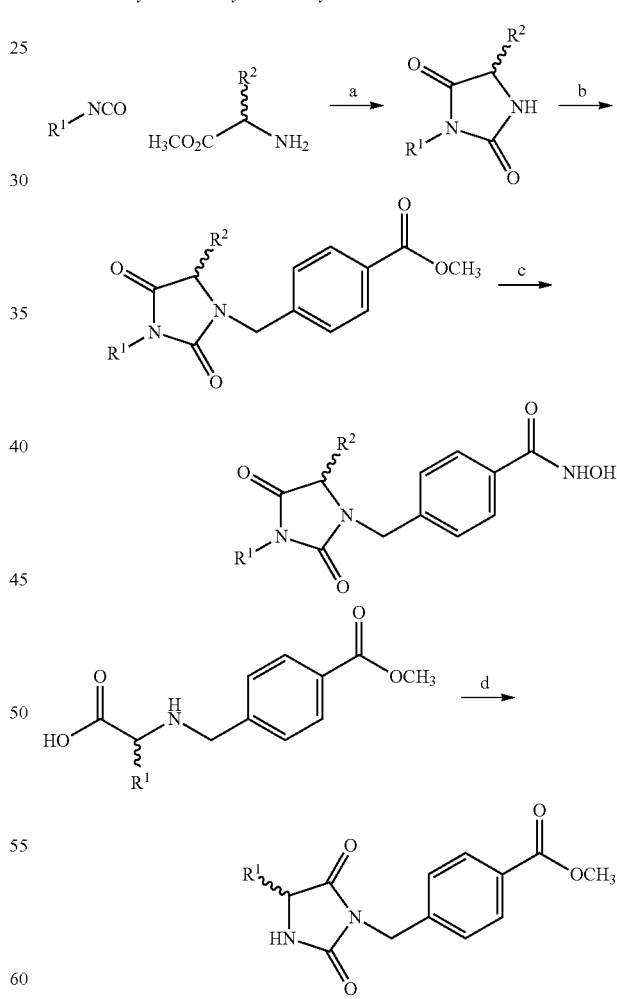

Reagents and conditions: (a) i. aq NaOH, ii. H+ 60° C. 1 h; (b) KOtBu, DMF, 0° C.-RT; (c) aq NH$_2$OH, NaOH, THF/MeOH; (d) triphosgene, Et$_3$N.

Specific examples of compounds of Formula I-C are as follows.

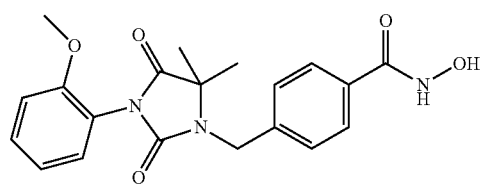

10a

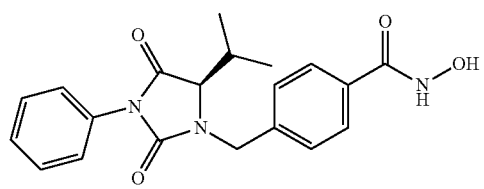

10b

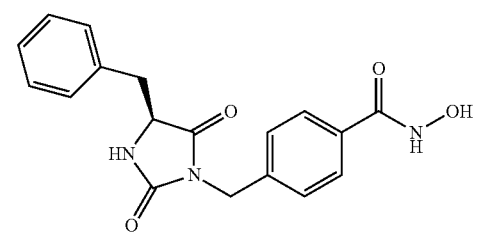

11a

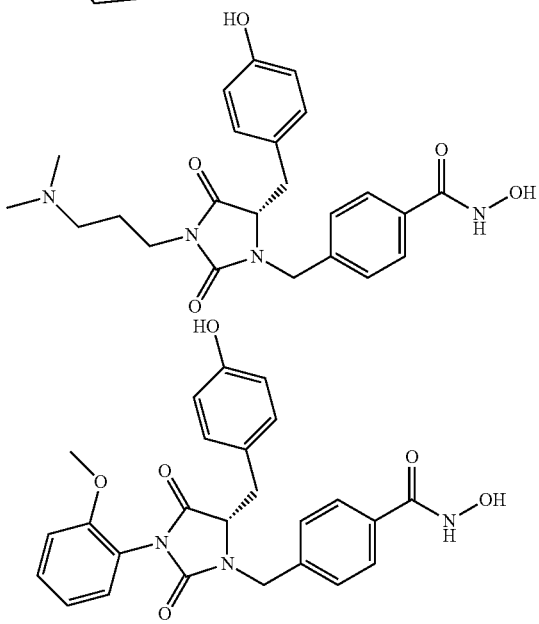

or pharmaceutically acceptable salts or hydrates thereof.

The disclosed compounds comprise, in one aspect, branched aryl or alkyl urea cap groups, or cyclic urea cap groups, introduced into the canonical HDACi platform. Introduction of branching elements, particularly to the proximal nitrogen atom of the urea motif, has led to the discovery of potent inhibitors that show excellent selectivity for HDAC6 versus the full panel of HDACs and are capable of inducing selective hyperacetylation of α-tubulin compared to histone protein. The SAR developed to this point indicates the branched urea scaffold imparts substantial gains in the desired biochemical activity. These compounds were also screened in cell systems, and both 5g and 5h were found to be capable of inhibiting the growth of B16 melanoma cell line.

Also disclosed are hydroxamate compounds that are devoid of the urea motif. Such compounds have Formula II.

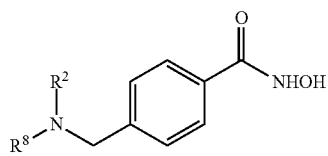

II wherein $R^2$ is as defined above and $R^8$ is acetyl, $C_1$-$C_5$ alkyloxycarbonyl, carbobenzyloxy, methoxybenzyl carbonyl, benzoyl, benzyl, methoxybenzyl, dimethoxybenzyl, methoxyphenyl, $C_1$-$C_5$ alkylcarbamate, or aryl sulfonyl, i.e., $R^9(SO_2)$, where $R^9$ is aryl optionally substituted with $C_1$-$C_5$ alkyl, amino, methoxyl, halo, or hydroxy, or a pharmaceutically acceptable salt or hydrate thereof. In preferred examples, $R^8$ can be $C_1$-$C_5$ alkyloxycarbonyl or arylsulfonyl. Specific examples of compounds of Formula II are as follows.

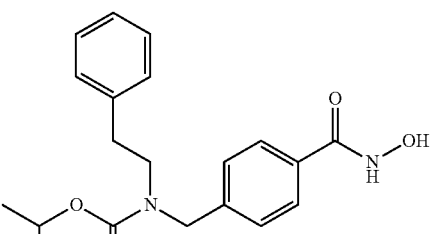

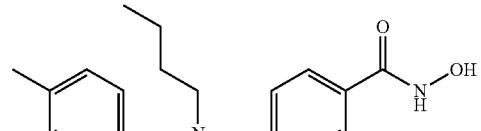

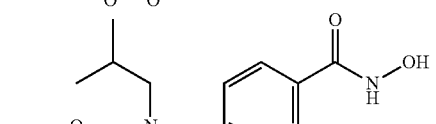

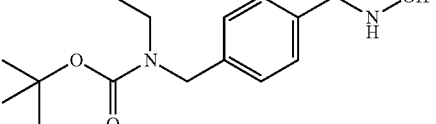

or pharmaceutically acceptable salts or hydrates thereof.

Also disclosed herein are pharmaceutically-acceptable salts and hydrates of the disclosed compounds. Pharmaceutically-acceptable salts include salts of the disclosed compounds that are prepared with acids or bases, depending on the particular substituents found on the compounds. Under conditions where the compounds disclosed herein are sufficiently basic or acidic to form stable nontoxic acid or base salts, administration of the compounds as salts can be appropriate. Examples of pharmaceutically-acceptable base addition salts include sodium, potassium, calcium, ammonium, or magnesium salt. Examples of physiologically-acceptable acid addition salts include hydrochloric, hydrobromic, nitric, phosphoric, carbonic, sulphuric, and organic acids like acetic, propionic, benzoic, succinic, fumaric, mandelic, oxalic, citric, tartaric, malonic, ascorbic, alpha-ketoglutaric, alpha-glycophosphoric, maleic, tosyl acid, methanesulfonic, and the like. Thus, disclosed herein are the hydrochloride, nitrate, phosphate, carbonate, bicarbonate, sulfate, acetate, propionate, benzoate, succinate, fumarate, mandelate, oxalate, citrate, tartarate, malonate, ascorbate, alpha-ketoglutarate, alpha-glycophosphate, maleate, tosylate, and mesylate salts. Pharmaceutically acceptable salts of a compound can be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Methods of Use

Further provided herein are methods of treating or preventing cancer in a subject, comprising administering to the subject an effective amount of a compound or composition as disclosed herein (e.g., JB7-19 or 20). Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation. Methods of treating inflammation in a subject are further provided herein, the methods comprising administering to the subject an effective amount of a compound or composition as described herein. Optionally, the methods can further include administering a second compound or composition (e.g., an anti-inflammatory agent).

The disclosed subject matter also concerns methods for treating a subject having an oncological disorder or condition. In one embodiment, an effective amount of one or more compounds or compositions disclosed herein is administered to a subject having an oncological disorder and who is in need of treatment thereof. The disclosed methods can optionally include identifying a subject who is or can be in need of treatment of an oncological disorder. The subject can be a human or other mammal, such as a primate (monkey, chimpanzee, ape, etc.), dog, cat, cow, pig, or horse, or other animals having an oncological disorder. Means for administering and formulating compounds for administration to a subject are known in the art, examples of which are described herein. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lung cancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor.

In one specific example, disclosed is a method of treating a subject with Human cutaneous T-cell lymphoma (CTCL) by administering an effective amount of a compound or compositions as disclosed herein.

In some aspect, disclosed are methods for treating a tumor or tumor metastases in a subject by the administration to the subject a combination of at least one HDAC inhibitor as disclosed herein and at least one cancer immunotherapeutic agent. The disclosed compounds can be administered alone or in combination with a cancer immunotherapeutic agent. The subject can receive the therapeutic compositions prior to, during or after surgical intervention to remove all or part of a tumor. Administration may be accomplished via direct immersion; systemic or localized intravenous (i.v.), intraperitoneal (i.p.), subcutaneous (s.c.), intramuscular (i.m.), or direct injection into a tumor mass; and/or by oral administration of the appropriate formulations.

A cancer immunotherapeutic agent suitable for use in the methods disclosed herein is an immunotherapeutic agent which comprises a cell effector component joined to a tumor associated antigen targeting component. Suitable cell effector components can include cytotoxic chemicals, cytotoxic radioisotopes, and cell signaling agents such as cytokines. Suitable tumor targeting components are polypeptide chains which bind to tumor associated antigens present on or in the surrounding tissue matrix of a tumor cell such as receptor protein chains or immunoglobulin chains.

Tumor associated antigens which can be used for targets of the immunotherapeutic agents include a tumor associated antigen selected from the group consisting of AFP, CA 125, CEA, CD19, CD20, CD44, CD45, EGF Receptor, GD[2], GD[3], GM1, GM2, Her-2/Neu, Ep-CAM (KSA), IL-2 receptor, Lewis-Y, Lewis-X (CD 15), melanoma-associated proteoglycan MCSP, PSA and Transferrin Receptor.

Examples of immunotherapeutic agents have an effector component that is a cytokine polypeptide joined to a targeting component which is an immunoglobulin (Ig) polypeptide chain.

The Ig polypeptide chain comprises a variable region which binds to a tumor associated antigen. It is preferred that said immunoglobulin chain, when combined with the appropriate complementary chain (i.e. a heavy chain complements a light chain) defines an antibody active site which is specific for a tumor associated antigen.

The tumor targeting Ig portion of the immunotherapeutic agent can comprise an entire immunoglobulin chain amino acid sequence, or at least the fragment of which comprises the antigen binding specificity portion of the protein. Thus, a suitable Ig polypeptide chain will have at least an Ig variable region specific for a tumor associated antigen.

An antibody and polypeptide chains therefrom, suitable for use in the disclosed methods, will have an amino acid sequence that can be of any mammalian origin. Where such antibody protein is not of the same origin as the anticipated patient, fragments of the antibody protein, such as F(ab')2, Fab, Fv or engineered Fv single chain antibody protein can be used. To further reduce antigenicity of the antibody protein, modification of the antibody amino acid sequence may be accomplished to reduce such by making the protein appear more like the patients normal antibody components. For example, monoclonal murine antibody amino acid sequences can be modified to appear more human, for administration to human patients by a variety of processes for humanization of the antibody.

Specific examples of cancer immunotherapeutic agents include an antibody that specifically binds CLTA-4, such as ipilimumab (Bristol-Myers Squibb), anti-PD-1, anti-PDL1. Other immunotherapeutic agents include the TNFα antagonists (e.g. etanercept), the B cell depleting agent rituximab, the anti-IL-6 receptor tocilizumab, and the costimulation blocker abatacept can be administered with the compounds or compositions disclosed herein.

In one specific example, the disclosed compounds are administered to a subject to treat cancer along with an IL-10 inhibitor. IL-10 is a cytokine with broad antiinflammatory properties. It acts primarily on APCs, including dendritic cells, monocytes, and macrophages, by inhibiting production of proinflammatory cytokines such as TNF and IL-12 and blocking cell maturation and upregulation of costimulatory molecules. This potent inhibitory effect on APCs makes the blockade of IL-10 a potential strategy for cancer therapy. Indeed, stimulation of tumor-resident APCs with Toll-like receptor agonists leads to poor responses unless IL-10 signaling is blocked through targeting of IL-10, IL-10R, or STAT3. The blockade leads to increased proinflammatory cytokine production, tumor necrosis, upregulation of costimulatory CD40, migration of dendritic cells to draining lymph nodes, and induction of antitumor inflammation and immunity. Therefore, IL-10 is a therapeutic target when combined with other immunotherapy.

The disclosed compounds can also be administered with toll like receptor (TLR) agonist. TLR agonist is a ligand for a TLR selected from the group consisting of TLR1, TLR2, TLR3, TLR4, and TLR9. For example, the TLR agonist can be a ligand selected from the group consisting of Pam3CSK4, Pam3CSK4, poly I:C, Ribomunyl, and CpG ODN.

The disclosed compounds can also be administered with an angiogenesis inhibiting agent, which is one which can inhibit the formation of new blood vessels (neovascularization) or enlargement of existing capillary networks into the tissues near a tumor cell. Suitable angiogenesis inhibiting agents can be peptides with angiogenesis inhibiting activity, such as the tumor associated antigen PSA. Other suitable angiogenesis inhibiting agents can be antagonists of VEGF associated angiogenesis, for example antagonists of the VEGF receptor on the surface of cells. One monoclonal antibody which can be used is LM609 (ATCC HB 9537).

Melanoma and Mantle Cell Lymphoma

In a preferred embodiment, disclosed herein is a method of treating a subject with melanoma by administering an effective amount of a compound of Formula 1 or II. Melanoma is currently the fastest growing cancer in incidence according to the World Health Organization. Currently, few therapies provide significant prolongation of survival for metastatic melanoma. Immunotherapy is an attractive modality with potentially few side effects due to the antigen specificity of adaptive immunity. The latest therapy approved by the FDA for the treatment of melanoma was ipilimumab, an antibody against CTLA-4, a key regulator of T-cell activity; however, this therapy offers modest improvements in overall survival.

Overcoming mechanisms of tumor-mediated immune suppression requires targeting multiple pathways. One strategy that has gained attention has been the use of histone deacetylase inhibitors (HDACi). Indeed, HDACi treatment has been shown to augment the expression of immunologically relevant genes such as MHC and co-stimulatory molecules. Inhibition of IL-10 is a potent anti-inflammatory cytokine upon treatment of macrophages with an HDACi. However; most studies to date have used pan-HDACi, which inhibit all 11 zinc-dependent HDACs. Therefore, the use of more selective HDACi is preferable in order to minimize side effects.

As demonstrated herein, HDAC6 is a molecular target in at least melanoma. Both pharmacologic and genetic disruption of HDAC6 in B16 murine melanoma cells' using HDAC6-selective inhibitors (HDAC6i) and targeted shRNA (HDAC6KD), respectively, led to inhibition of proliferation, characterized by G1 arrest measured by propidium iodine staining for DNA content. Furthermore, treatment with the HDAC6i led to enhanced expression of immunologically relevant receptors including MHC-I and MHC-II. In vivo, subcutaneous injection in wild type mice of HDAC6KD B16 cells led to delayed tumor growth as compared with control cells. However, this effect was abrogated in experiments using SCID mice, which lack T- and B-cells, suggesting a critical immune component for tumor control in vivo.

The mechanism(s) by which HDAC6 regulates tumor immunogenicity are yet to be defined. One possible mechanism arises from protein immunoprecipitation studies which demonstrate that HDAC6 interacts with, and potentially regulates of STAT3, an important survival and pathogenic factor in melanoma, which also has implications for immune tolerance.

The expression HDAC6 was found to be upregulated in a majority of melanoma patient tumor biopsies by gene microarray analysis, as compared with normal skin. This observation was supported by immunohistochemically-stained patient melanoma tissue microarray.

Taken together, HDAC6 inhibition is an attractive therapeutic target in melanoma and mantle cell lymphoma by both delaying tumor growth and conferring a more attractive immune target, providing rationale for the development and use of selective HDAC6i.

Inflammatory Responses

It has previously been shown that tumor antigen specific CD8+ T cells are unresponsive in patients with melanoma (Lee et al., *Nat. Med.* 1999, 5:677-85). T cells infiltrating the bone marrow of patients with multiple myeloma are also unresponsive (Noonan et al. Cancer Res. 65:2026-34, 2005). The conclusion of these studies, along with several other reports in the literature, is that CD4+ T cells are rendered tolerant to tumor antigens early in tumor progression. This presents a significant barrier to the development of effective cancer immunotherapy.

The role of histone deacetylases (HDACs) in the epigenetic regulation of inflammatory responses in APCs is disclosed herein. HDACs are a group of enzymes that remove an acetyl group from lysine residues on histones to regulate chromatin architecture and gene expression. HDACs are grouped into four distinct classes as depicted in FIG. 1.

HDACs are targets for histone deacetylase inhibitors (HDACi) as depicted in FIG. 2. HDACi's are structurally diverse compounds that are capable of targeting several HDACs. HDACi's induce differentiation, cell cycle and growth arrest in cancer cells. There is an emerging role for HDACi's as modulators of inflammation and antitumor responses.

It was previously found that Pan-HDACi LAQ824 augments inflammatory responses in macrophages through transcriptional regulation of IL-10. Pan-HDACI LAQ824 was also found to restore the responsiveness of tolerant T cells (Wang et al. *J Immunol* 2011, 186:3986-96). The mechanisms and relevant targets of Pan-HDACIs are difficult to elucidate given their multiple effects. Understanding the expression and function of specific HDACs in APCs may unveil novel targets to influence immune activation versus immune tolerance. The identified target(s) may then be subject to pharmacologic inhibition with isotype-selective HDACi's.

Figure 3:
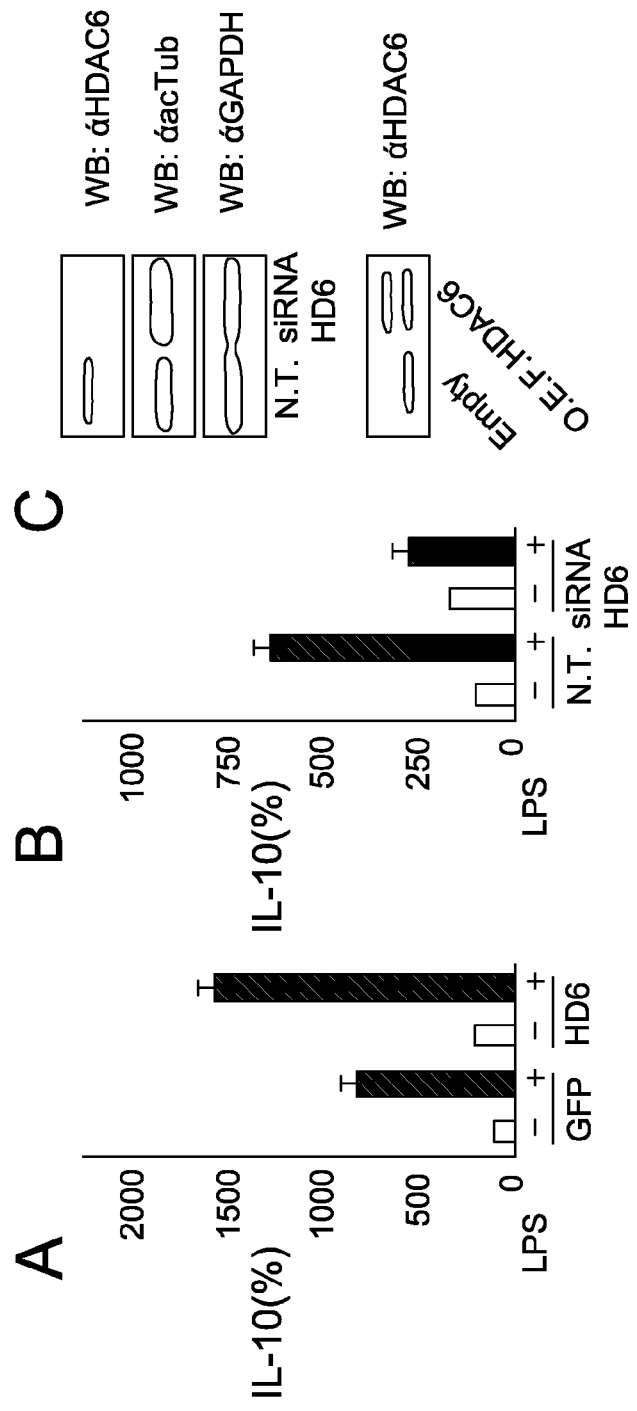
FIG. 3 is an image depicting HDAC6 was found to influence the IL-10 gene expression in APCs.
Figure 4:
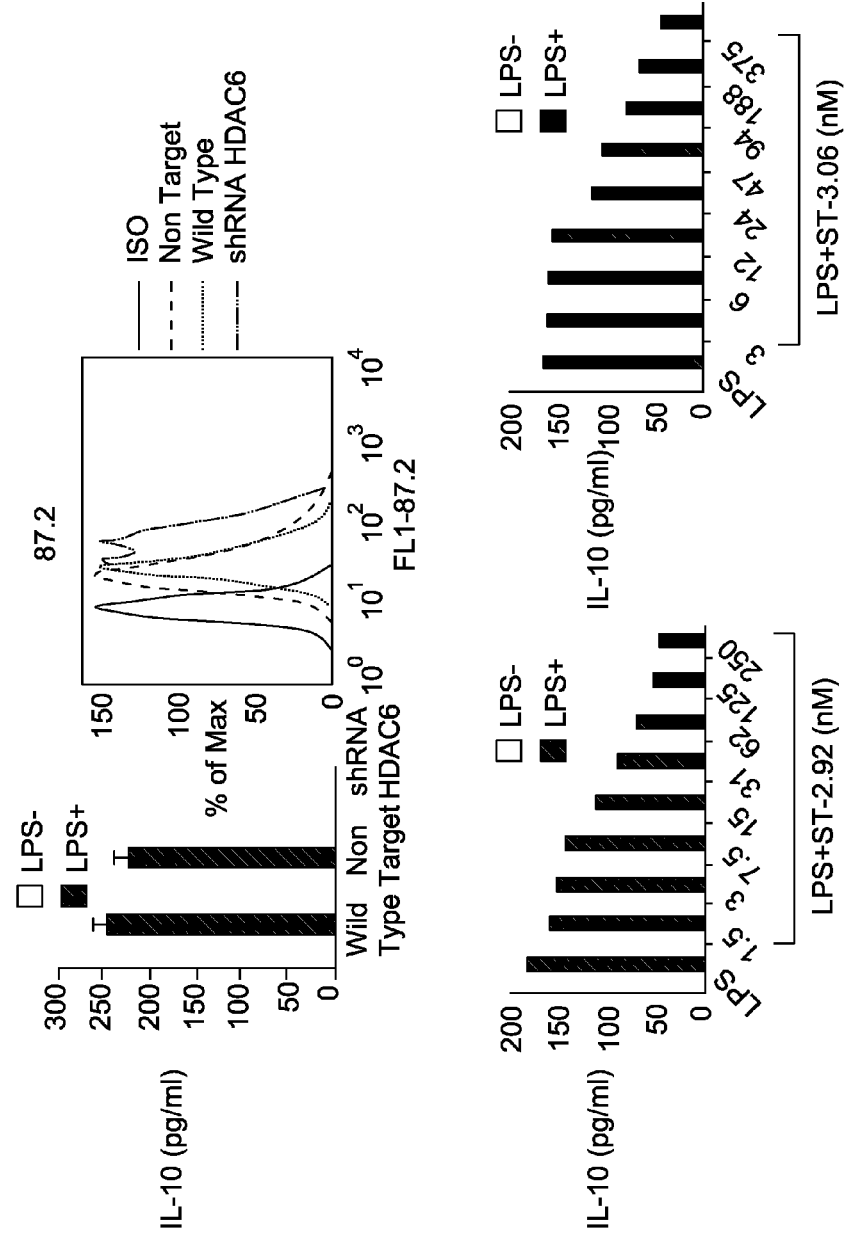
FIG. 4 is an image depicting the genetic or pharmacologic disruption of HDAC6 inhibits IL-IO.
Figure 5:
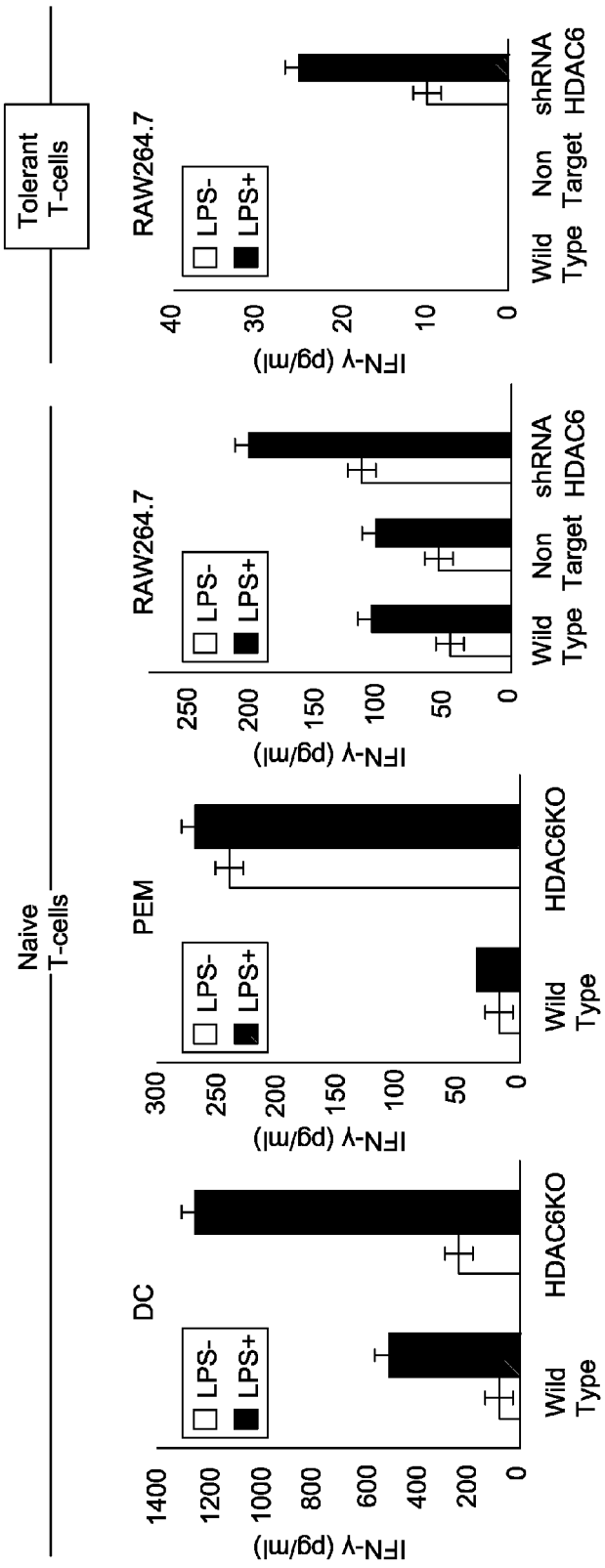
FIG. 5 is an image depicting the genetic disruption of HDAC6 enhances APC function.
Figure 6:
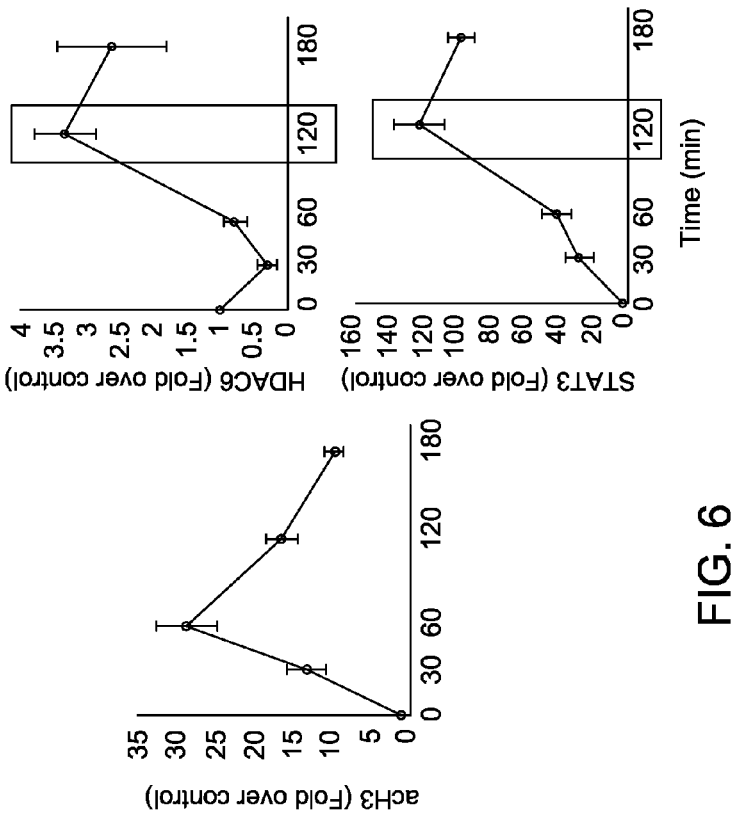
FIG. 6 is an image depicting mechanisms as shown by CHIP analysis of IL-I0gene promotor in macrophages include H3 and H4 acetylation; HDAC6 recruitment; and binding of STAT3 and other transcription factors at several timepoints after LPS stimulation.

HDAC6 was found to influence the IL-10 gene expression in APCs as shown in FIG. 3. HDAC6 is a 131 kDa protein encoded on the X chromosome that is mainly cytoplasmic; however, recent data suggests that HDAC6 may also be present in the nucleus). HDAC6 has tubulin deacetylase activity related to cell motility and T cell/APC synapse. There are isotype-selective HDAC6 inhibitors available. FIG. 4 illustrates the genetic or pharmacologic disruption of HDAC6 inhibits IL-10. FIG. 5 illustrates the genetic disruption of HDAC6 enhances APC function. Mechanisms as shown by CHIP analysis of IL-I0 gene promotor in macrophages include H3 and H4 acetylation; HDAC6 recruitment; and binding of STAT3 and other transcription factors at several timepoints after LPS stimulation as shown in FIG. 6.

Figure 7:
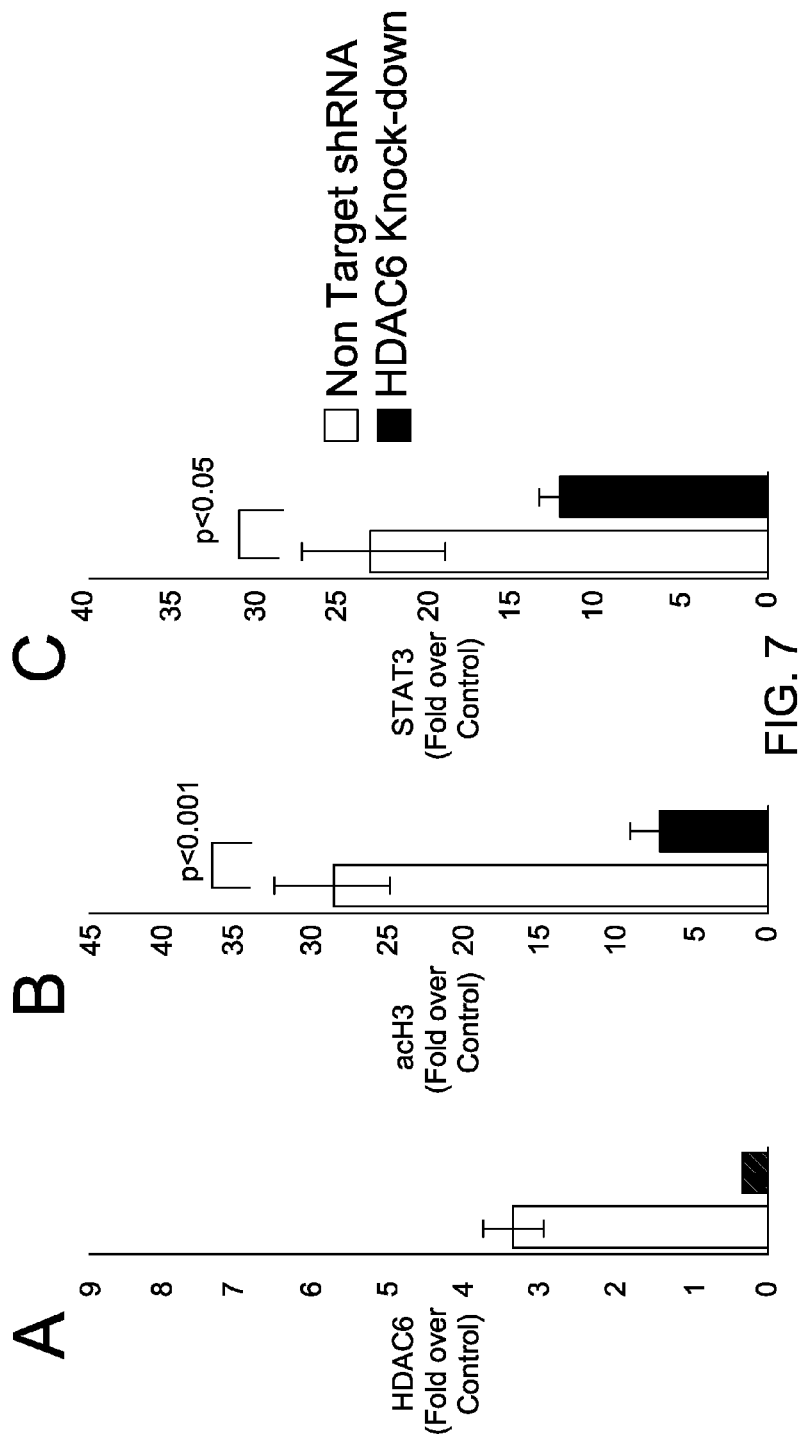
FIG. 7 is an image depicting that knocking down HDAC6 results in a decreased recruitment of the transcriptional activator STAT3 to the IL-10 gene promotor.
Figure 8:
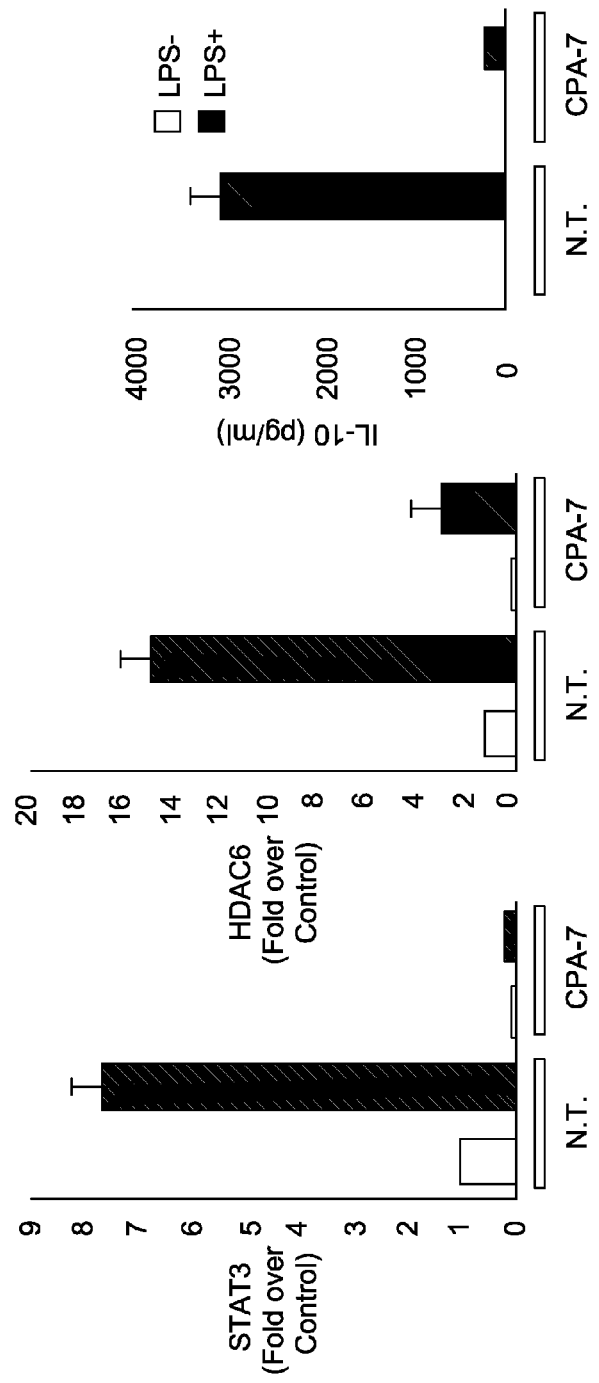
FIG. 8 is an image depicting disruption of STAT3 binding to the gene promoter resulted in decreased recruitment of HDAC6 and diminished IL-10 production.
Figure 9:
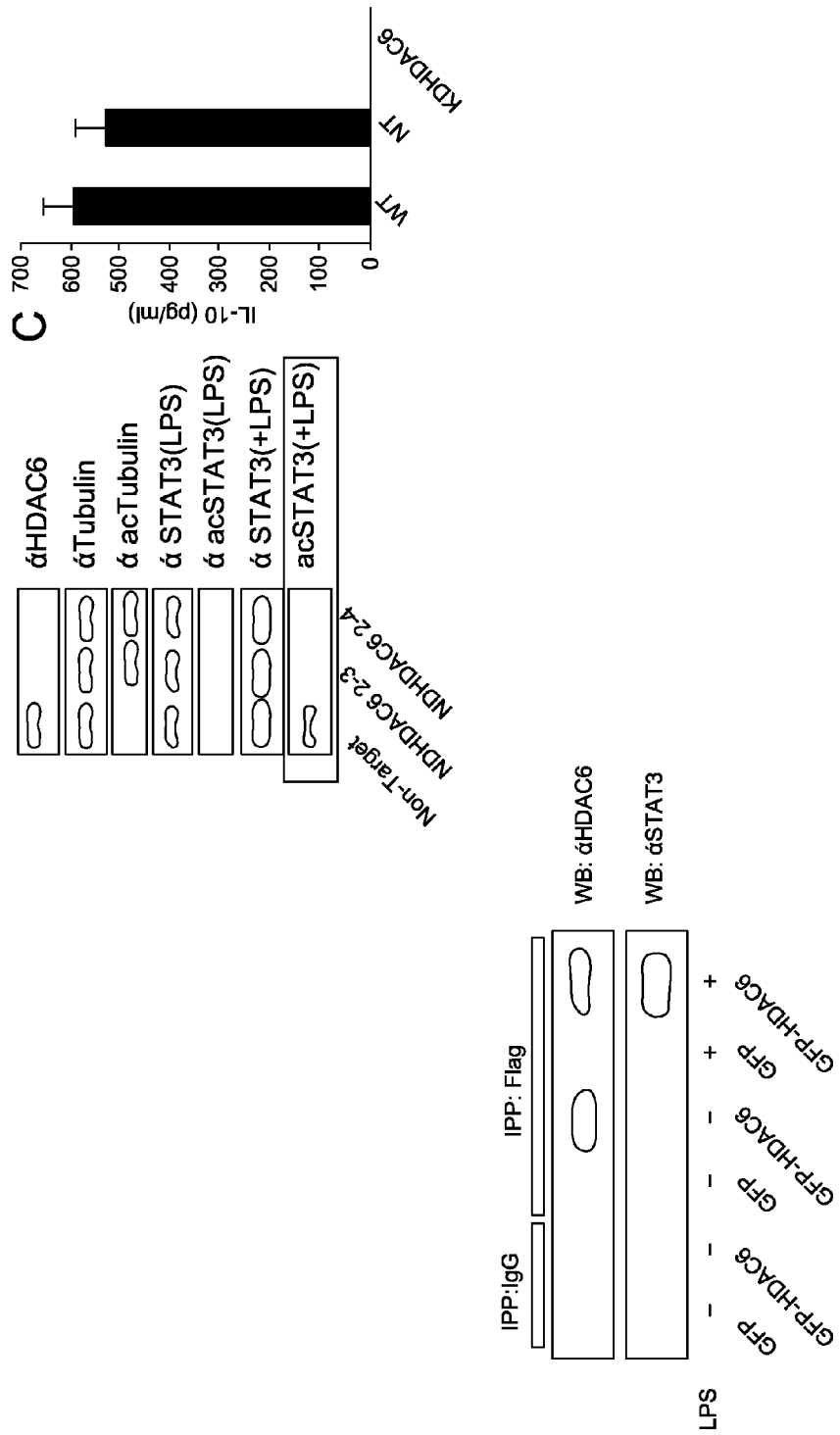
FIG. 9 is an image depicting disruption of HDAC6 inhibits STAT3 phosphorylation.

FIG. 7 illustrates that knocking down HDAC6 results in a decreased recruitment of the transcriptional activator STAT3 to the IL-10 gene promotor. The C-terminus of HDAC6 is required for interaction with HDAC11. FIG. 8 illustrates that disruption of STAT3 binding to the gene promotor resulted in decreased recruitment of HDAC6 and diminished IL-10 production. FIG. 9 illustrates that the disruption of HDAC6 inhibits STAT3 phosphorylation.

Figure 10:
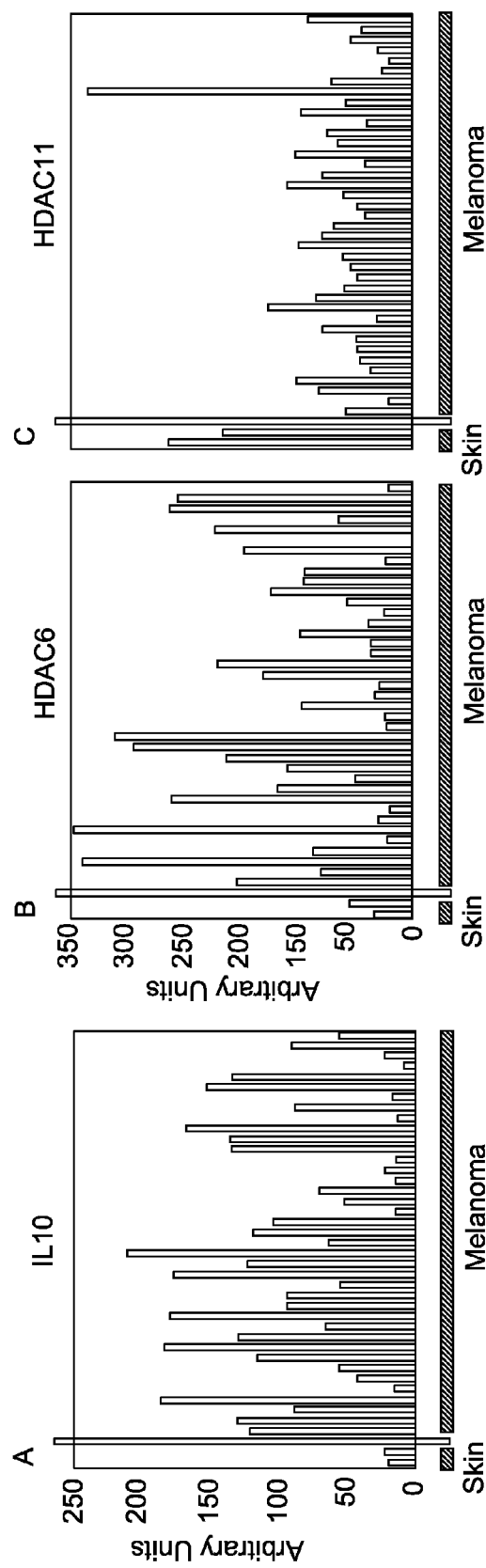
FIG. 10 is a series of images depicting that increased expression of HDAC6 and IL-10mRNA in human melanoma.
Figure 11:
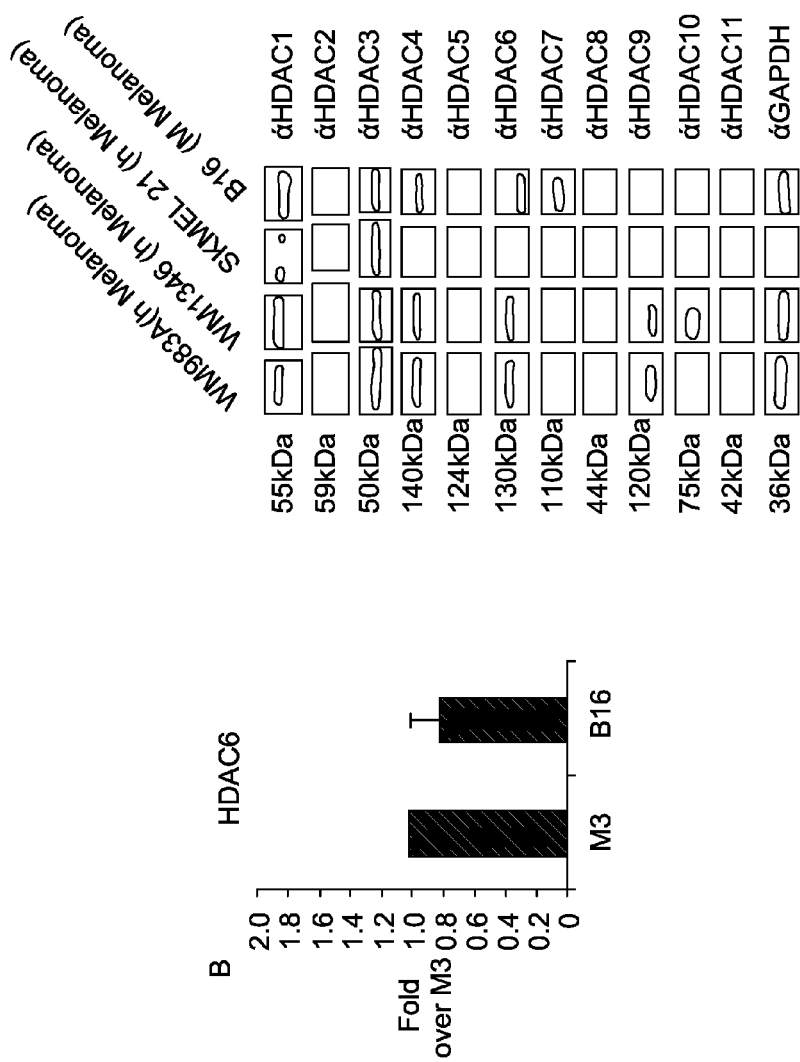
FIG. 11 is a series of images that illustrate HDAC6 expression in murine and human melanoma cell lines.
Figure 12:
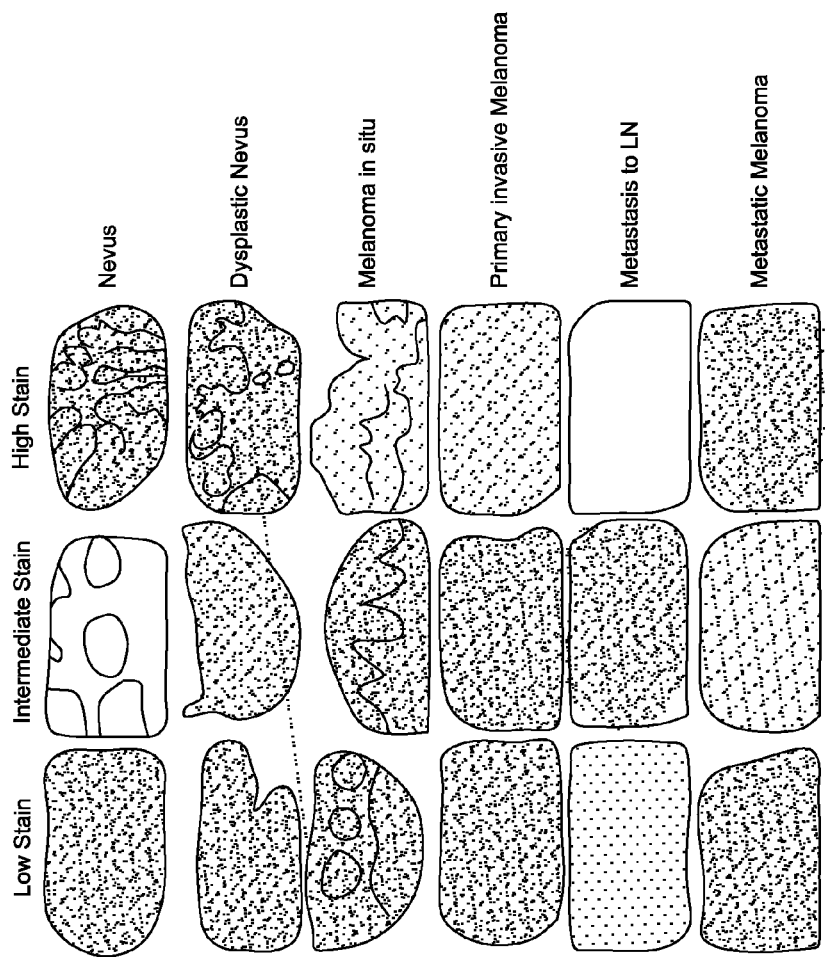
FIG. 12 is a series of images depicting HDAC protein expression in melanoma.
Figure 13:
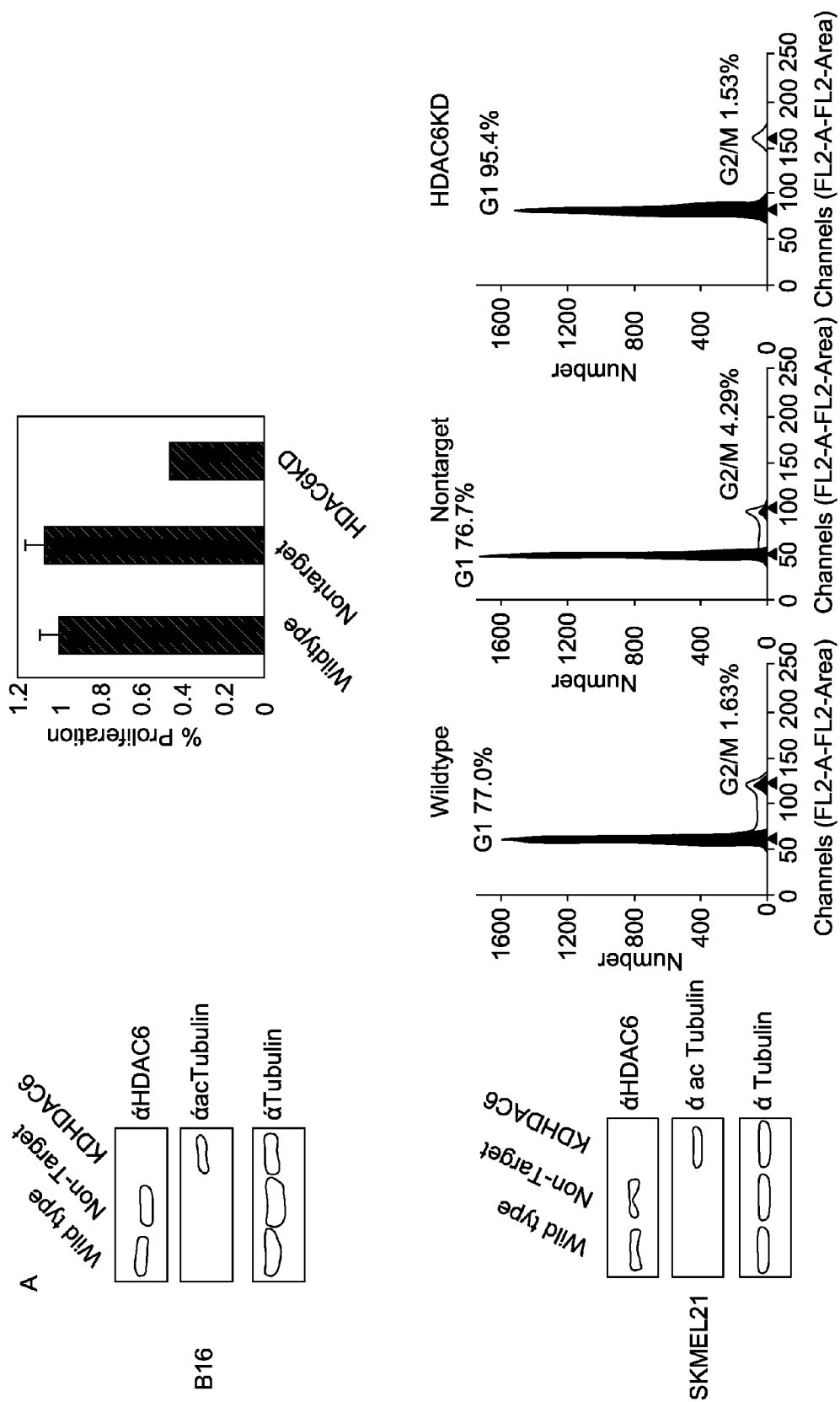
FIG. 13 is a series of images depicting decreased proliferation and cell cycle arrest in melanoma cells lacking HDAC6.
Figure 14:
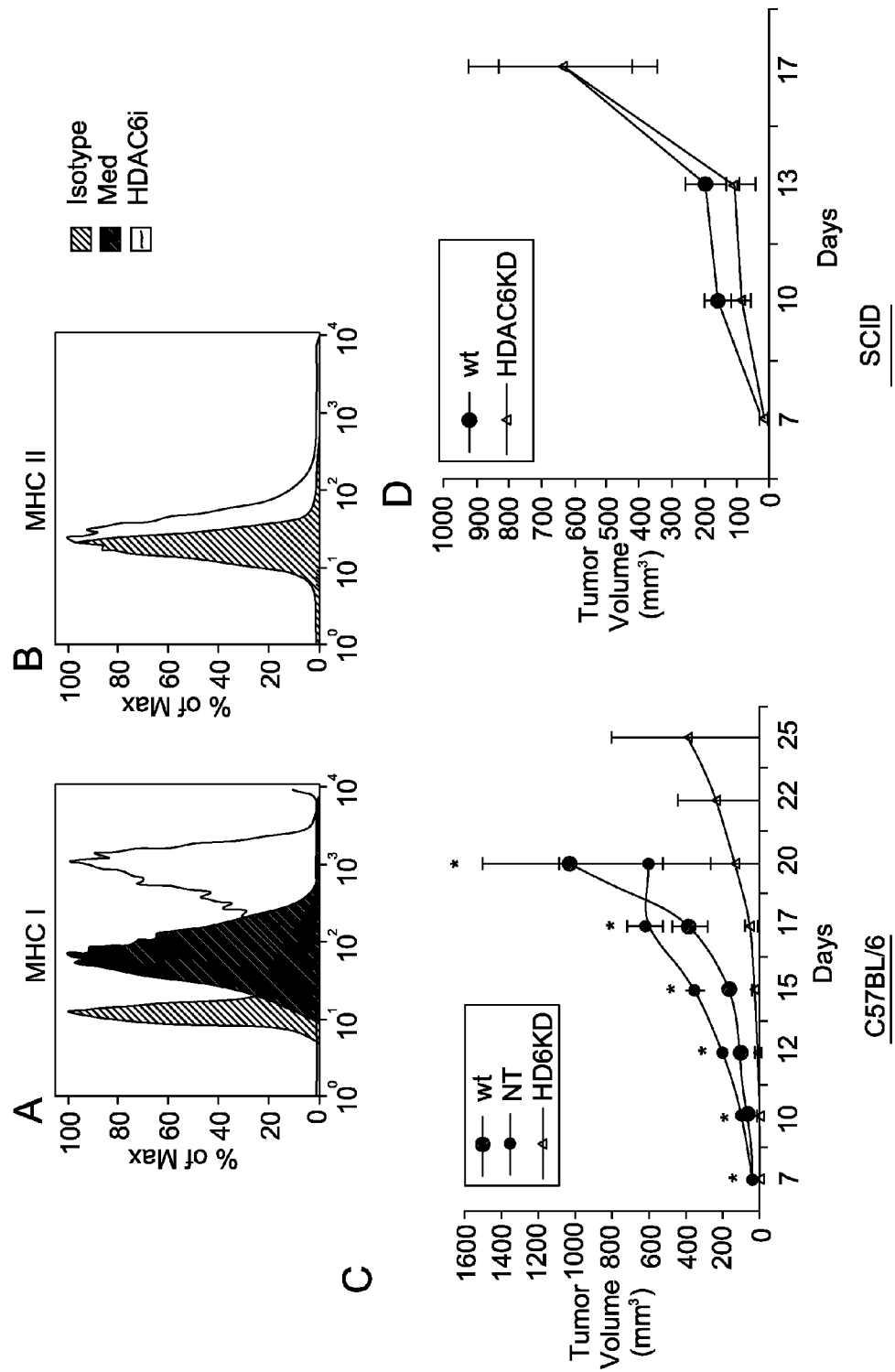
FIG. 14 is a series of images depicting melanoma cells lacking in HDAC6 are more Immunogemc.

FIG. 10 illustrates that there is increased expression of HDAC6 and IL-10mRNA in human melanoma. FIG. 11 is a series of images that illustrate HDAC6 expression in murine and human melanoma cell lines. FIG. 12 is a series of images depicting HDAC protein expression in melanoma. FIG. 13 is a series of images depicting decreased proliferation and cell cycle arrest in melanoma cells lacking HDAC6. FIG. 14 is a series of images depicting melanoma cells lacking in HDAC6 are more immunogenic.

As shown in FIGS. 14A and 14B, B16 cells treated with the HDAC6i ST-2-92 displayed an elevated expression of MHC-I and -II molecules relative to untreated B16 cells. Similar changes in MHC expression were observed in B16 cells in which HDAC6 was knocked down. Of note, a delay in tumor growth was observed in C57BL16 mice challenged in vivo with B16-KDHDAC6 cells (FIG. 14C). This delay in tumor growth in KDHDAC6 melanoma cells could be a reflection of their diminished proliferation (FIGS. 12-13) and/or an increase in their immunogenicity leading to improved immune recognition and clearance. To address this question, C57BL16 SCID mice were challenged with either KDHDAC6 or WTB16 melanoma cells. Unlike immune competent mice in which a delay in KDHDAC6 tumor growth was observed (FIG. 14C); such an effect was not observed in SCID mice challenged with the same KDHDAC6 cells (FIG. 14D). These results suggest that the immunological effects triggered by disruption of HDAC6 in melanoma cells make these cells "better seen" by the immune system.

Figure 15:
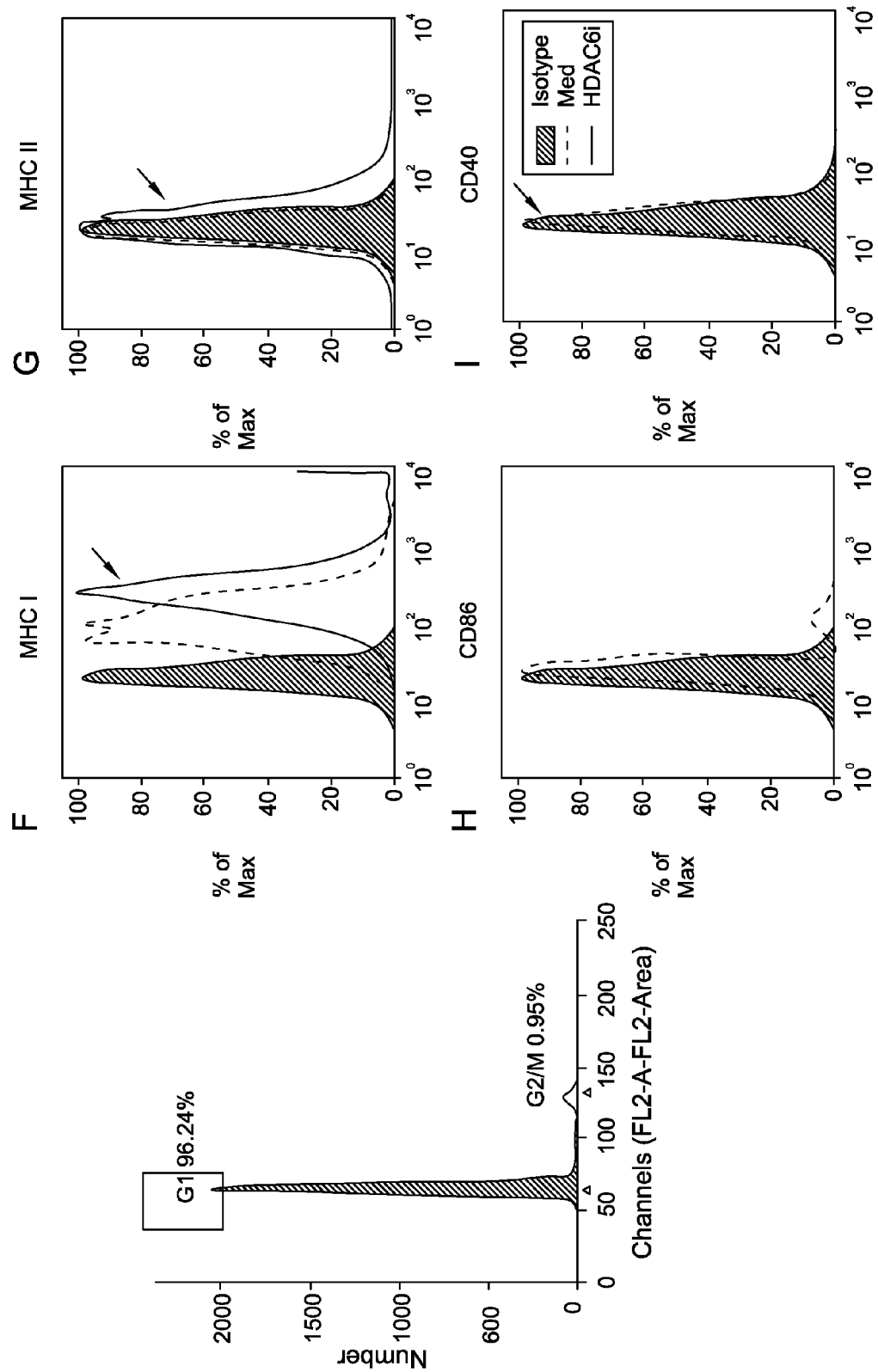
FIG. 15 is a series of images depicting the pharmacologic inhibition of HDAC6 in melanoma cells resulted in cell cycle arrest and increased expression of MHC molecules.

FIG. 15 is a series of images depicting the pharmacologic inhibition of HDAC6 in melanoma cells resulted in cell cycle arrest and increased expression of MHC molecules. It was also found that melanoma cells treated with HDAC6 specific inhibitors are better activators of T-cells (CD4 and/or CD8). The procedures for this finding include loading OVA-peptide into melanoma cells (treated or not with Tubastatin A) and adding OT-1 or OT-II transgenic T-cells (naive or tolerized) and determining their production of IL-2 and IFN-gamma.

Figure 16:
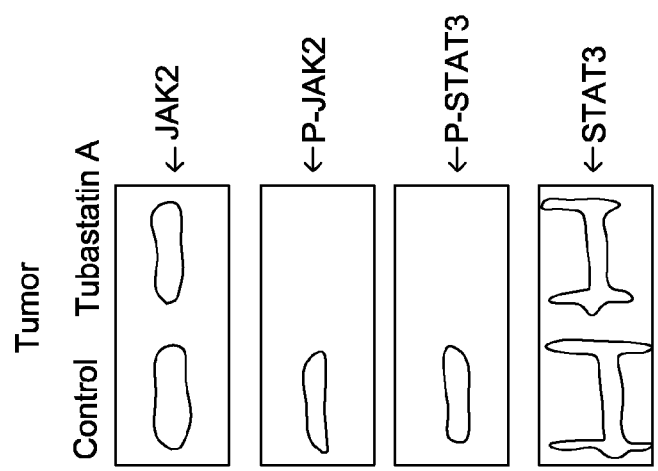
FIG. 16 is an image depicting tubastatin-A inhibits JAK2/STAT3 phosphorylation in B16 murine melanoma cells in vivo.
Figure 17:
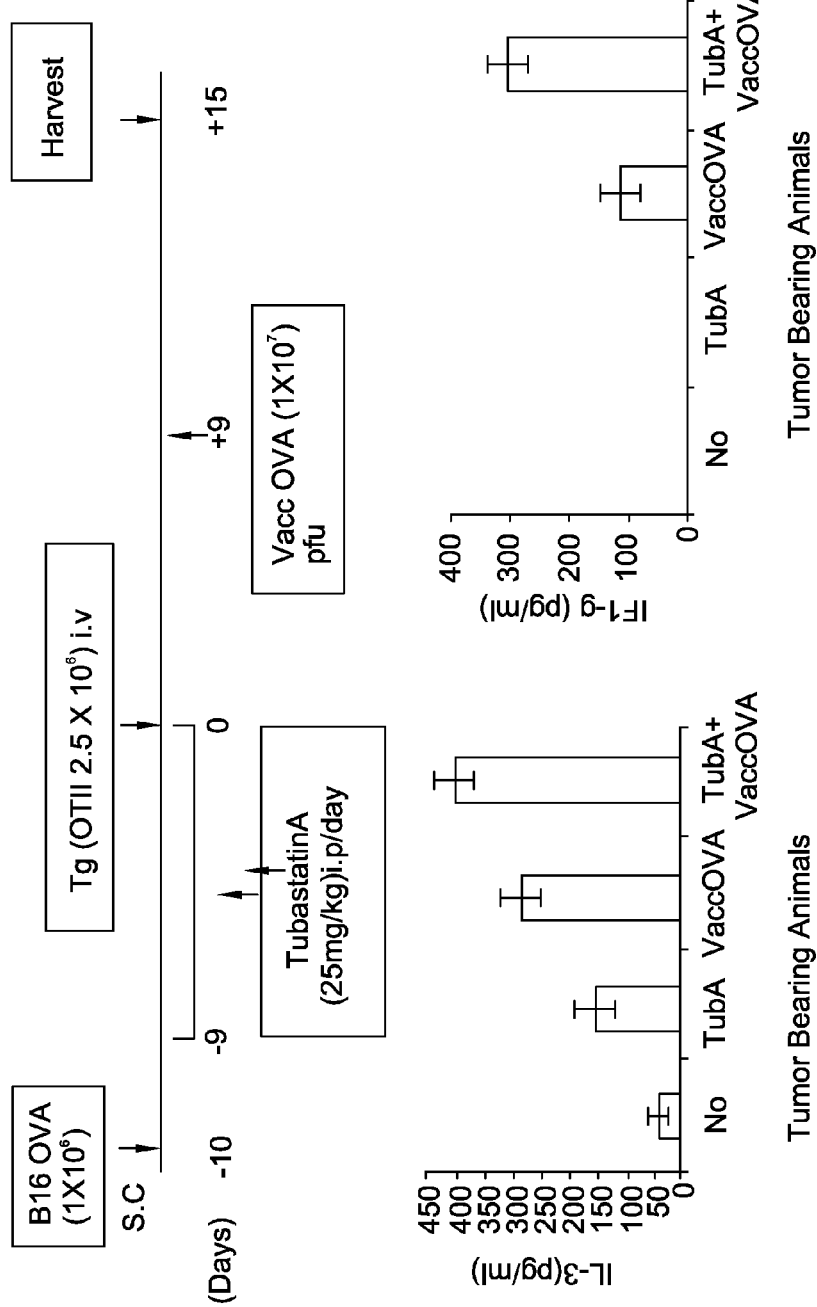
FIG. 17 is a series of images depicting tubastatin A augments antigen-specific CD4+T-cell responses to vaccination in melanoma bearing mice.

FIG. 16 is an image depicting Tubastatin-A inhibits JAK2/STAT3 phosphorylation in B16 murine melanoma cells in vivo. FIG. 17 is a series of images depicting Tubastatin A augments antigen-specific CD4+ T-cell responses to vaccination in melanoma bearing mice. There is an anti-melanoma effect after administration of tubastatin A in vivo (alone or in combination with anti-CLTA4).

Figure 18:
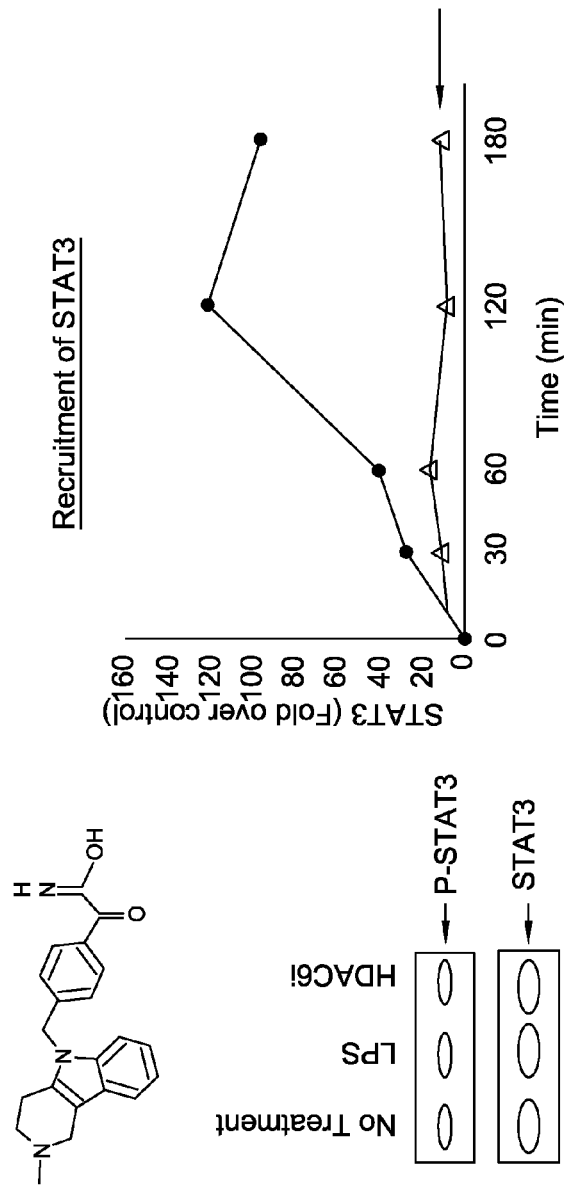
FIG. 18 is an image depicting tubastatin A, a selective HDAC6 inhibitor decreased STAT3 phosphorylation and recruitment to the IL-10 gene promotor in APCs.
Figure 19:
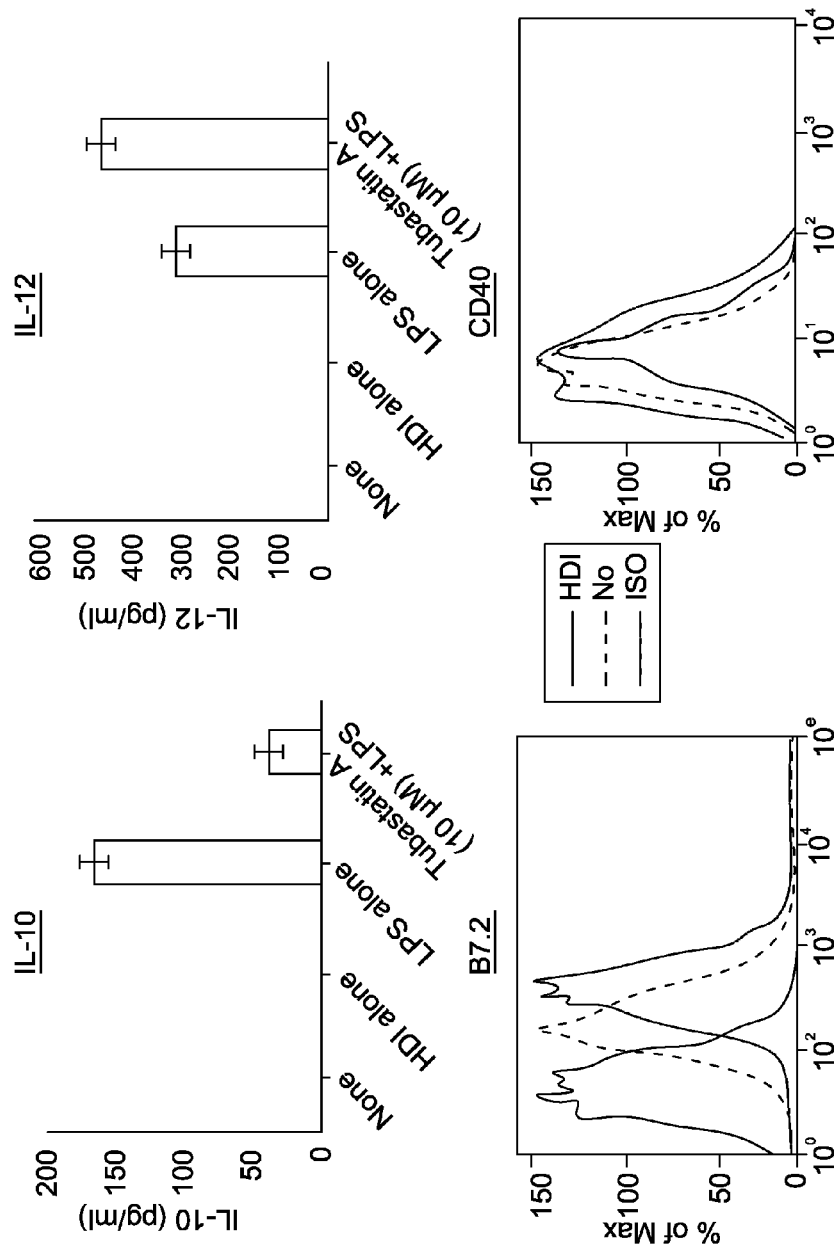
FIG. 19 is an image depicting the phenotypic and functional changes in APCs treated with Tubastatin A.
Figure 20:
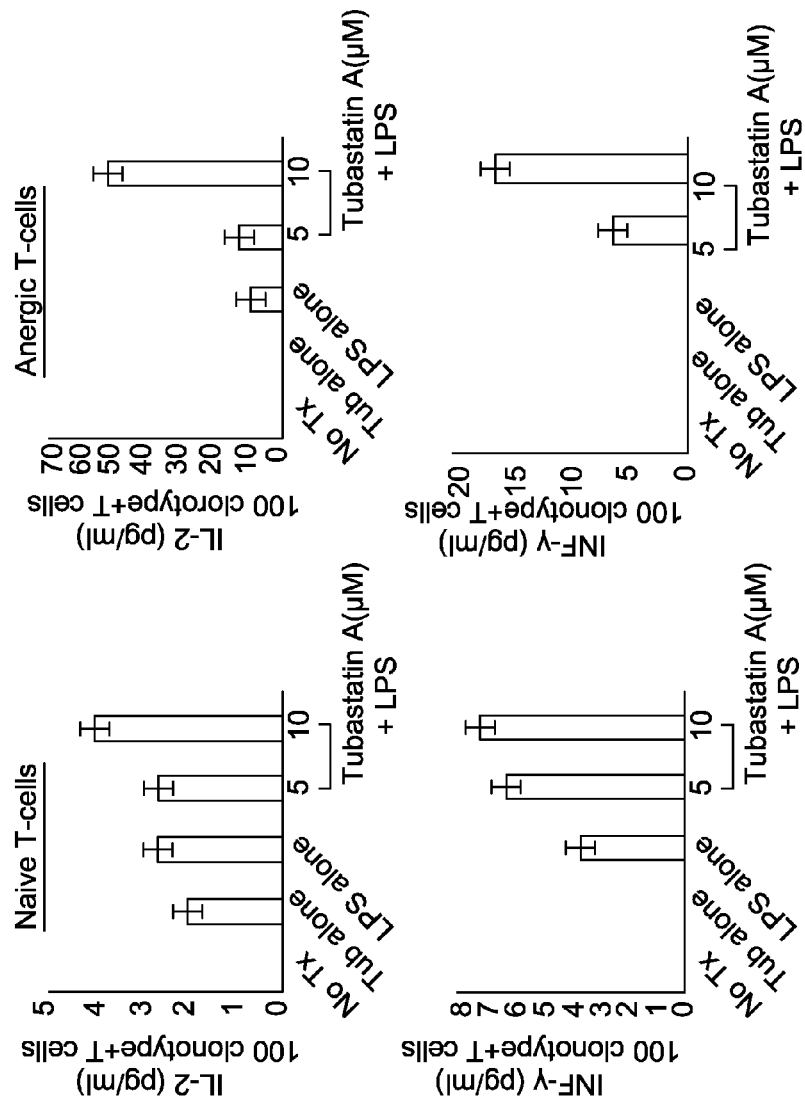
FIG. 20 is an image depicting tubastatin A-treated APCs are better activators of naïve T-cells and restore the responsiveness of anergic T cells.
Figure 21:
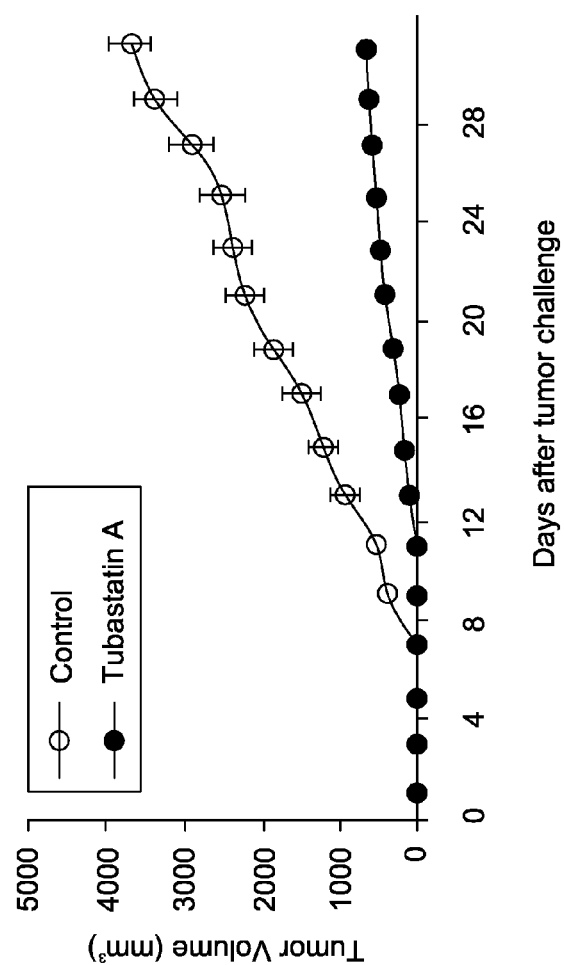
FIG. 21 is a graph depicting the antitumor effect of tubastatin A in vivo.
Figure 22:
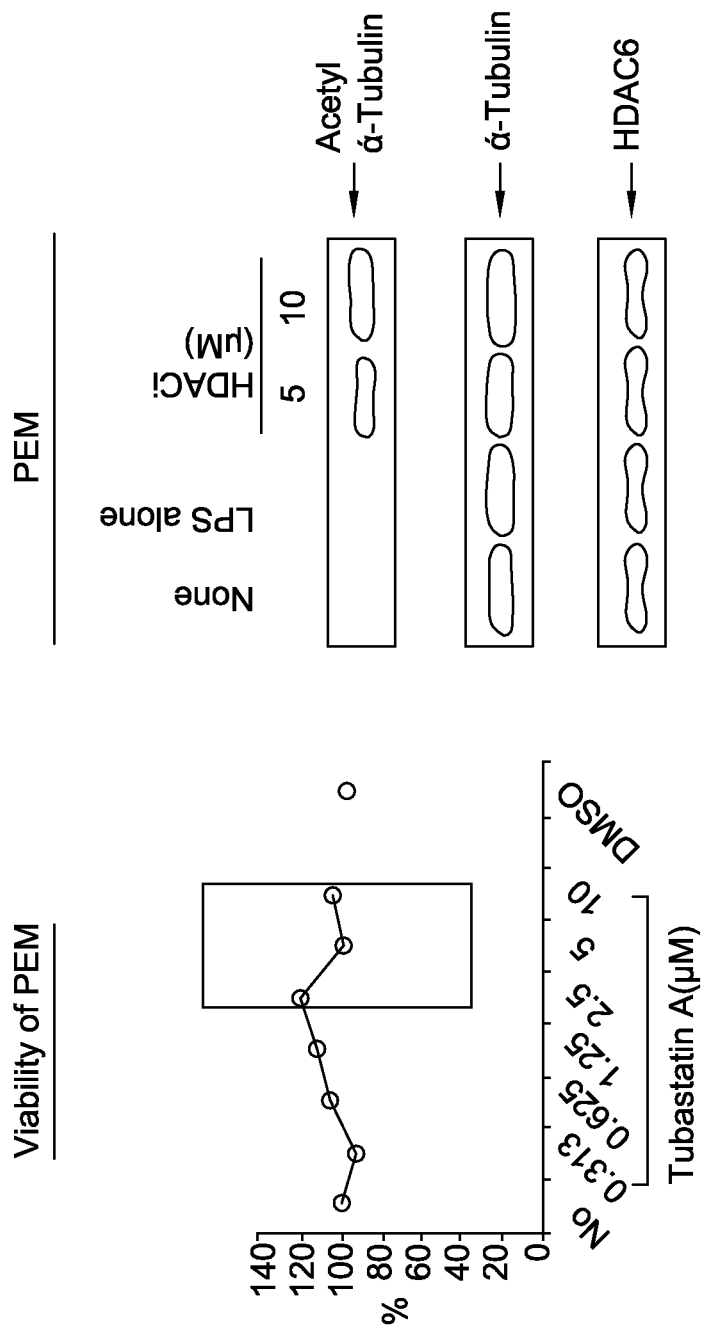
FIG. 22 is a series of images depicting that tubastatin A does not affect PEM.
Figure 24:
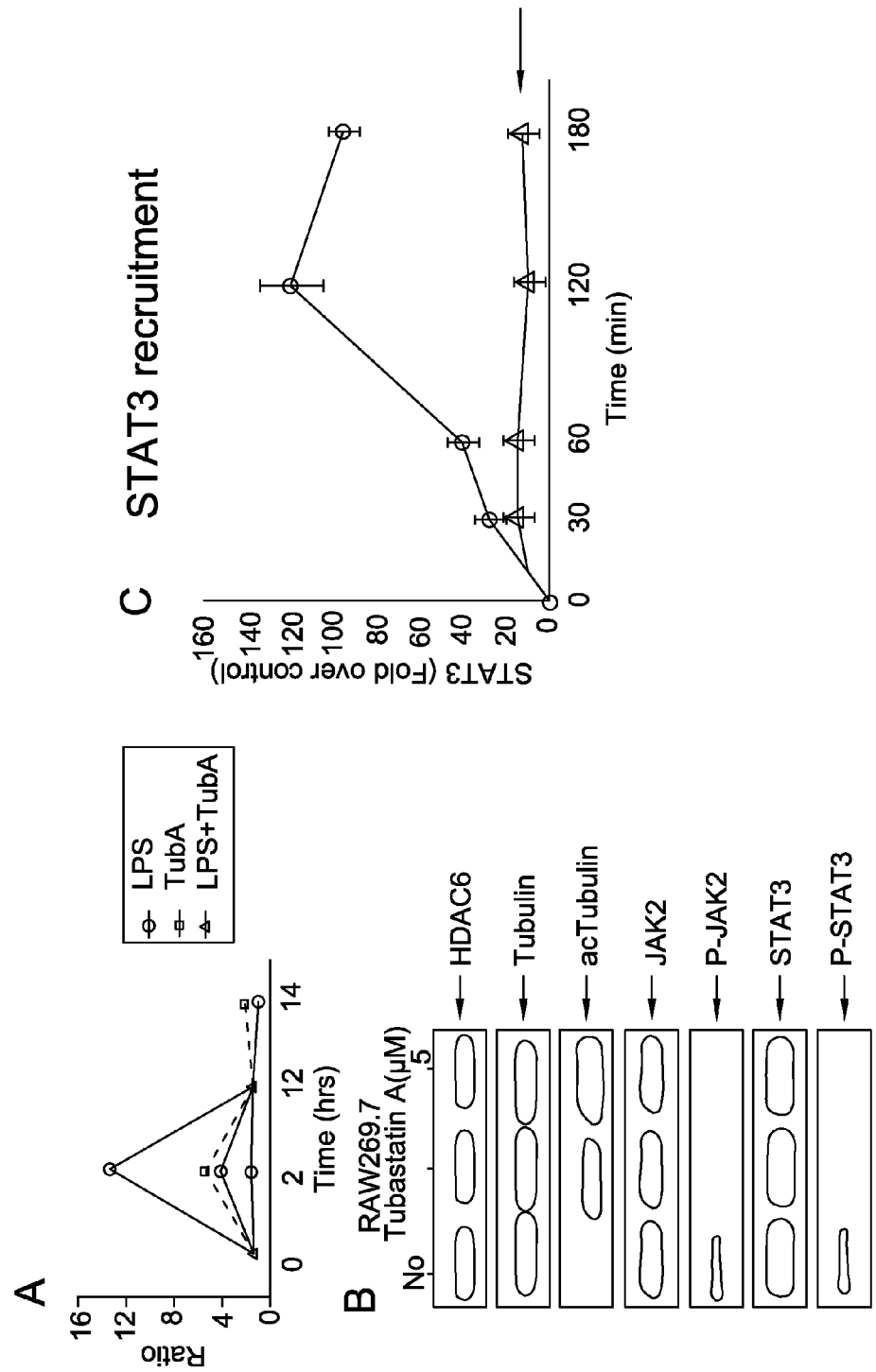
FIG. 24 is a series of images depicting Tubastatin A inhibits IL-I0 transcription by disrupting the JAKISTAT3 pathway in macrophages.
Figure 25:
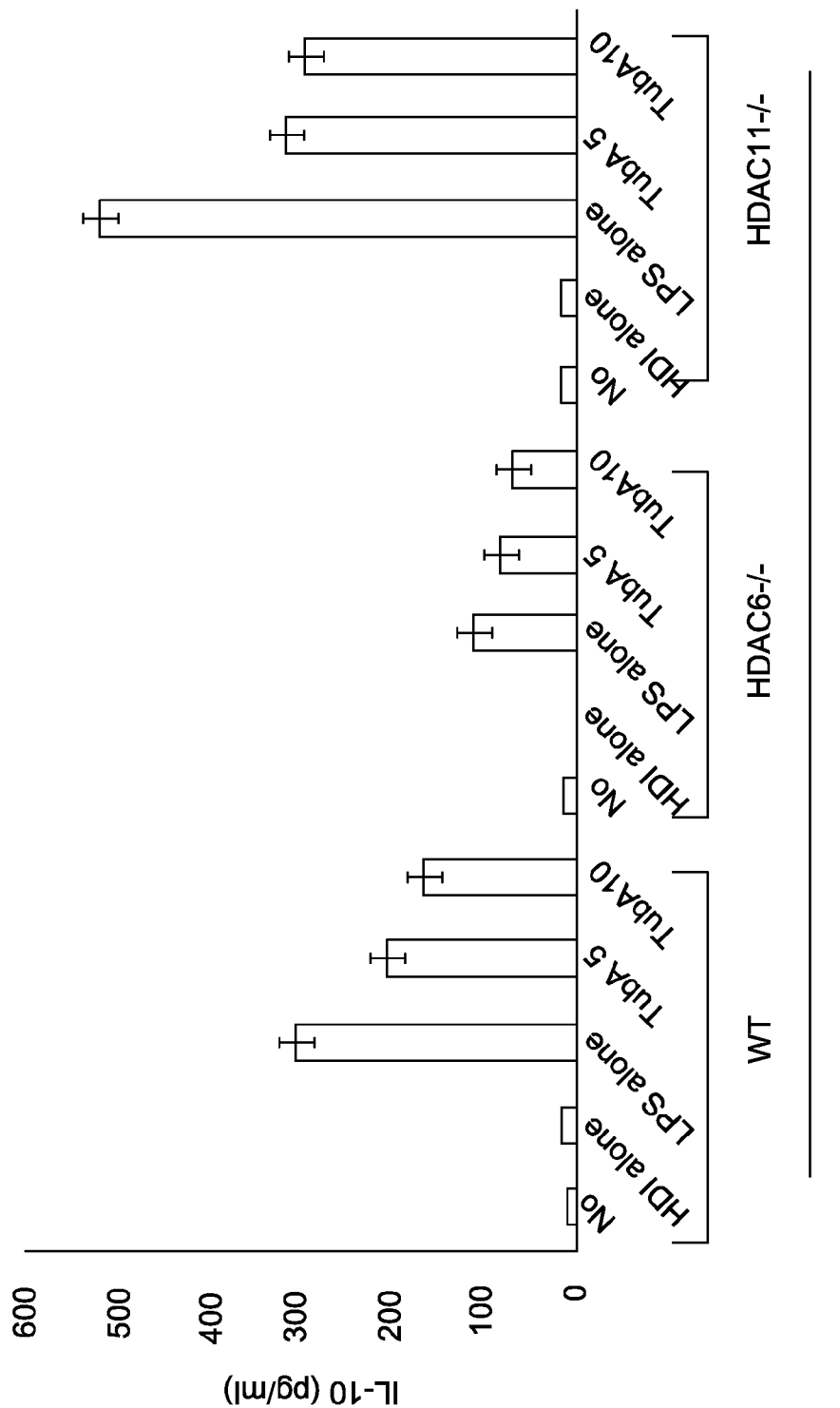
FIG. 25 is a graph depicting the inhibitory effect of tubastatin A upon IL-I0 production is lost in the absence of HDAC6.
Figure 26:
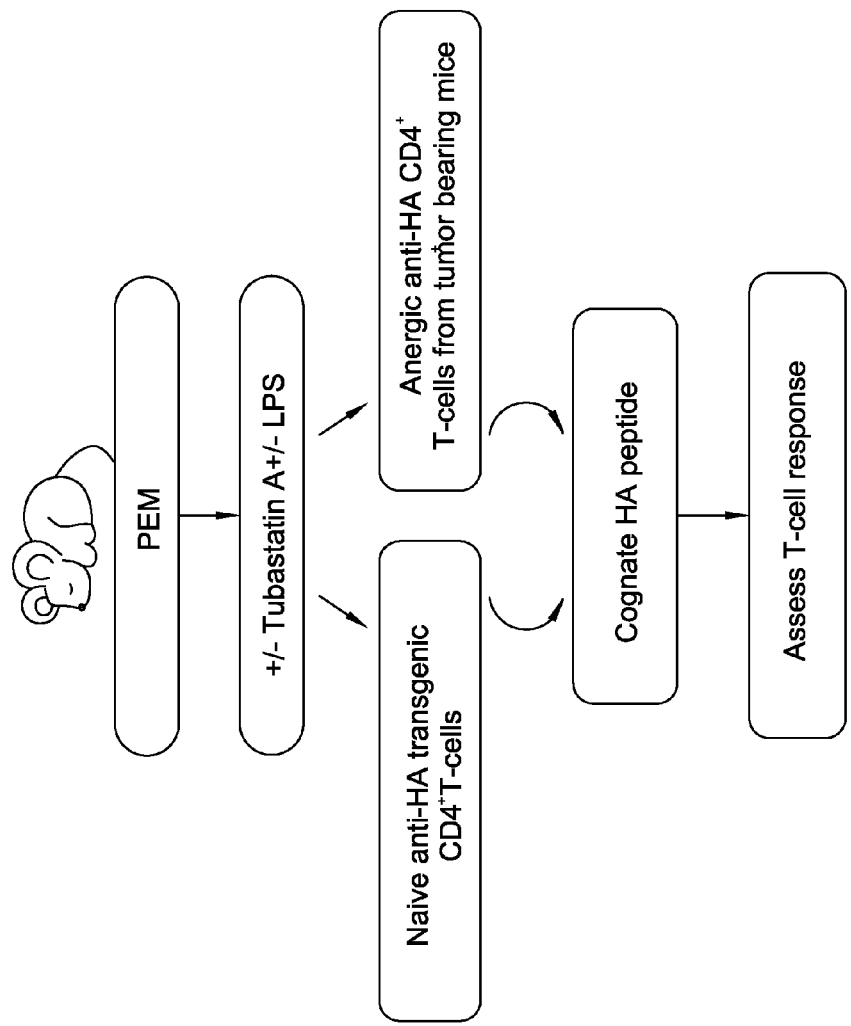
FIG. 26 is a flow chart depicting the experimental design of the in vitro antigen presenting studies.
Figure 27:
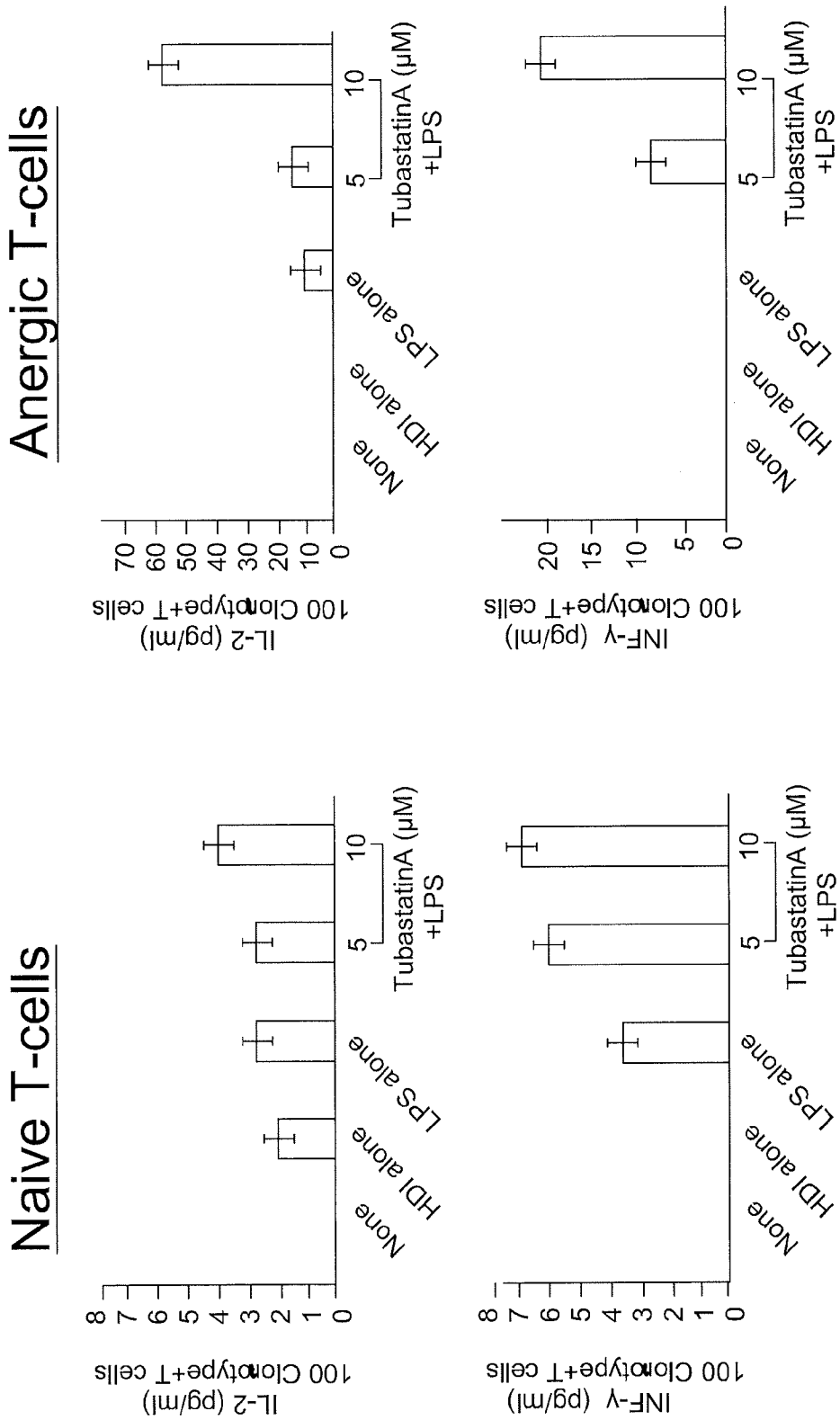
FIG. 27 is a series of images depicting that tubastatin A treated macrophages are better activators of naïve T-cells and restore function of anergic T-cells.
Figure 28:
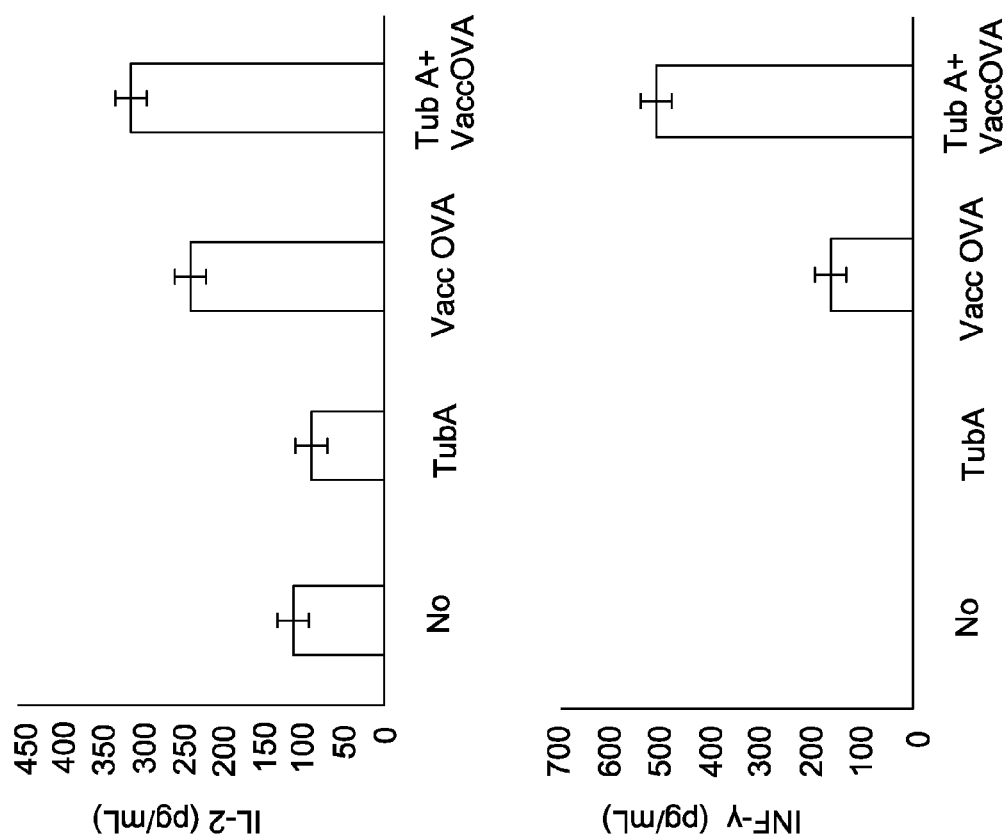
FIG. 28 is a series of images depicting in vivo treatment with tubastatin A augment the response of antigen-specific T-cell to vaccination.

FIG. 18 illustrates the Tubastatin A, a selective HDAC6 inhibitor decreased STAT3 phosphorylation and recruitment to the 1L-10 gene promotor in APCs. FIG. 19 illustrates the phenotypic and functional changes in APCs treated with Tubastatin A. FIG. 20 illustrates that tubastatin A-treated APCs are better activators of naive T cells and restore the responsiveness of anergic T cells. FIG. 21 is a graph depicting the antitumor effect of Tubastatin A in vivo. FIG. 22 depicts that Tubastatin A does not affect PEM. FIG. 23 is a series of images depicting the immunological effects of Tubastatin A upon macrophages. FIG. 24 is a series of images depicting Tubastatin A inhibits IL-10 transcription by disrupting the JAKISTAT3 pathway in macrophages. FIG. 25 is a graph depicting the inhibitory effect of Tubastatin A upon IL-10 production is lost in the absence of HDAC6. FIG. 26 is a flow chart depicting the experimental design of the in vitro antigen-presenting studies. FIG. 27 is a series of images depicting that Tubastatin A treated macrophages are better activators of naIve Tcells and restore function of anergic T-cells. FIG. 28 is a series of images depicting in vivo treatment with tubastatin A augment the response of antigen-specific T-cell to vaccination.

The experiments with Tubastatin A in APCs above indicate that treatment of macrophages with Tubastatin-A increased the expression of co-stimulatory molecules and inhibits IL-10 production by these cells. Tubastatin A-treated macrophages are better activators of naïve T-cells and restore the responsiveness of anergic T-cells in vitro. In vivo treatment with Tubastatin-A enhances antigen-specific T-cell responses to vaccination. Mechanistically, Tubastatin-A disrupt JAKISTAT3/IL-iO pathway and tip the balance towards immunogenic rather than tolerogenic macrophages.

Figure 29:
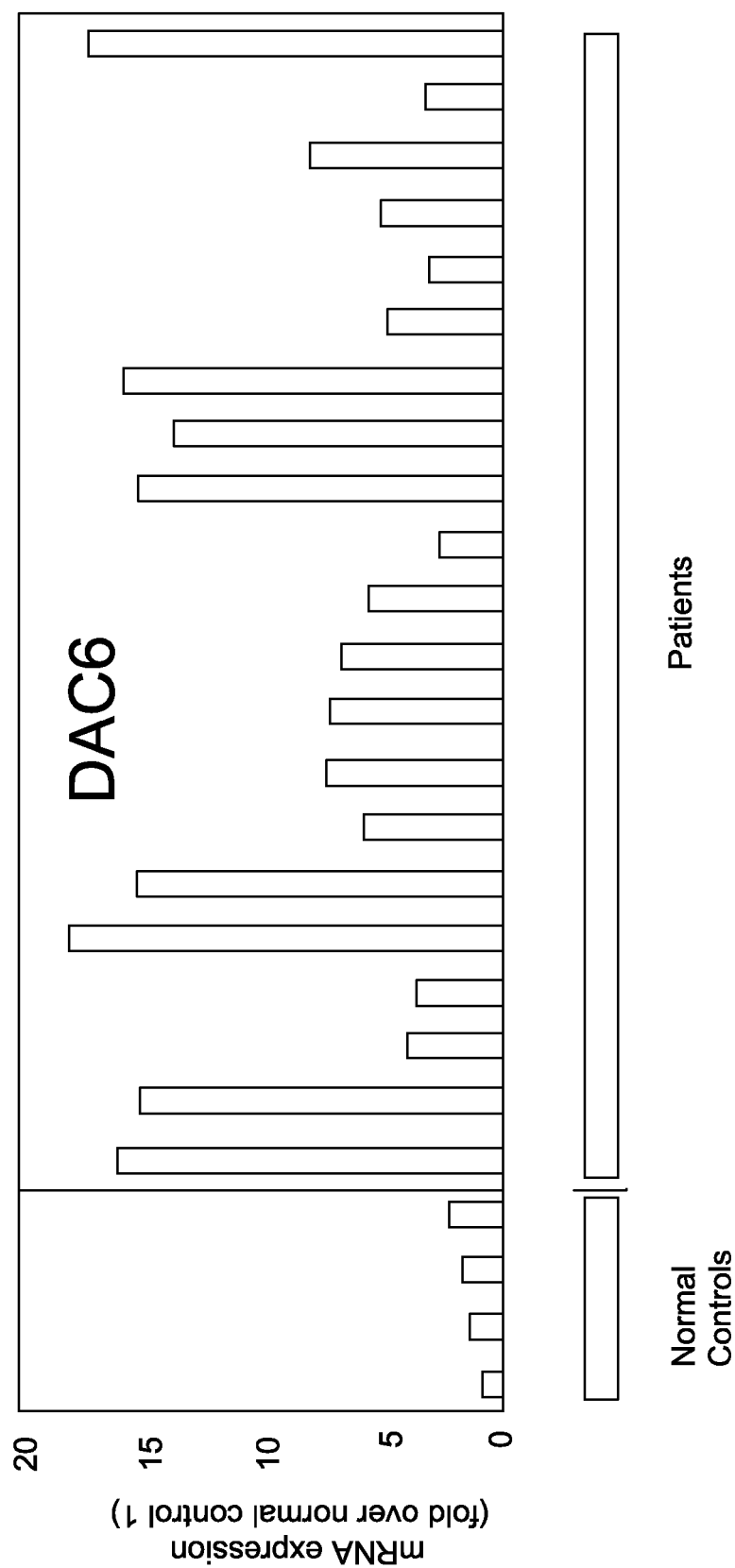
FIG. 29 is an image depicting HDAC6 expression in human MCL.
Figure 31:
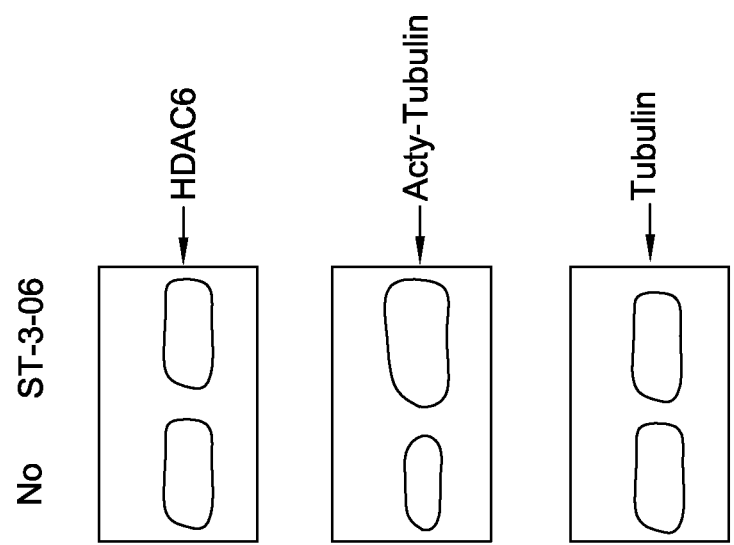
FIG. 31 is an image depicting the disruption of HDAC6 in murine FC-muMCLI cells.
Figure 32:
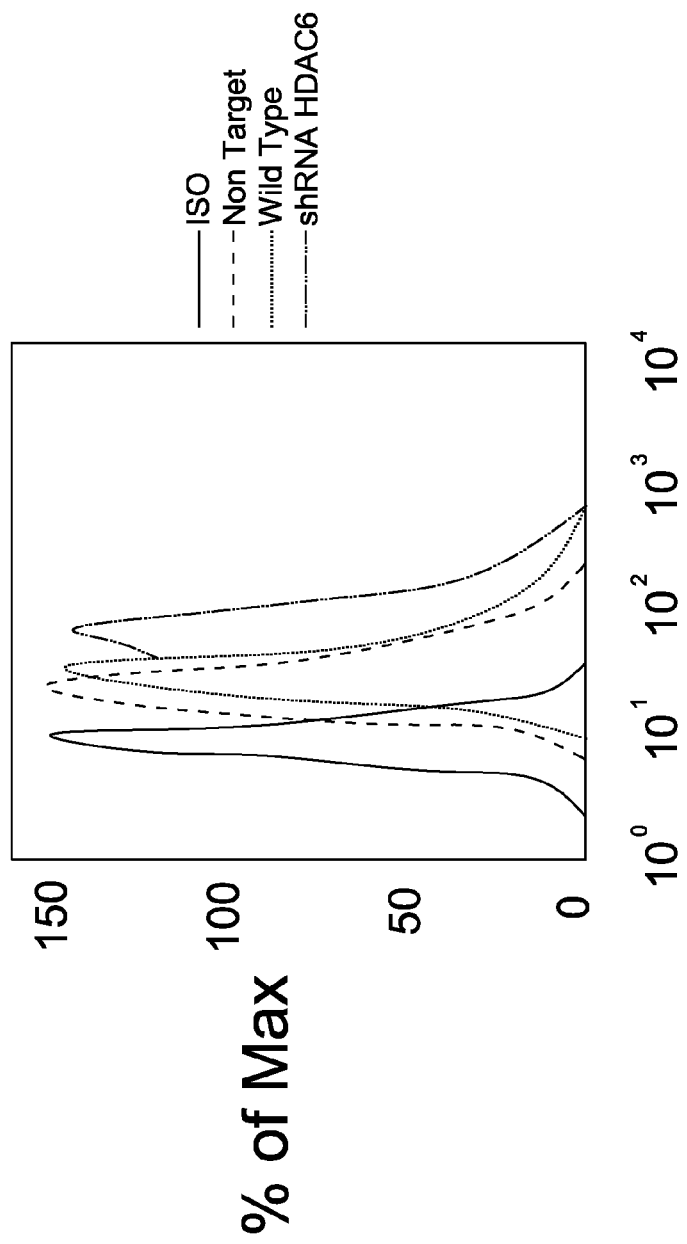
FIG. 32 is an image depicting the immunological effects of HDAC6 inhibition in MCL. Changes in MHC, co-stimulatory molecules and/or cytokine production in response to LPS or CpG+/− ST-3-06 or Tubastatin A are show.
Figure 33:
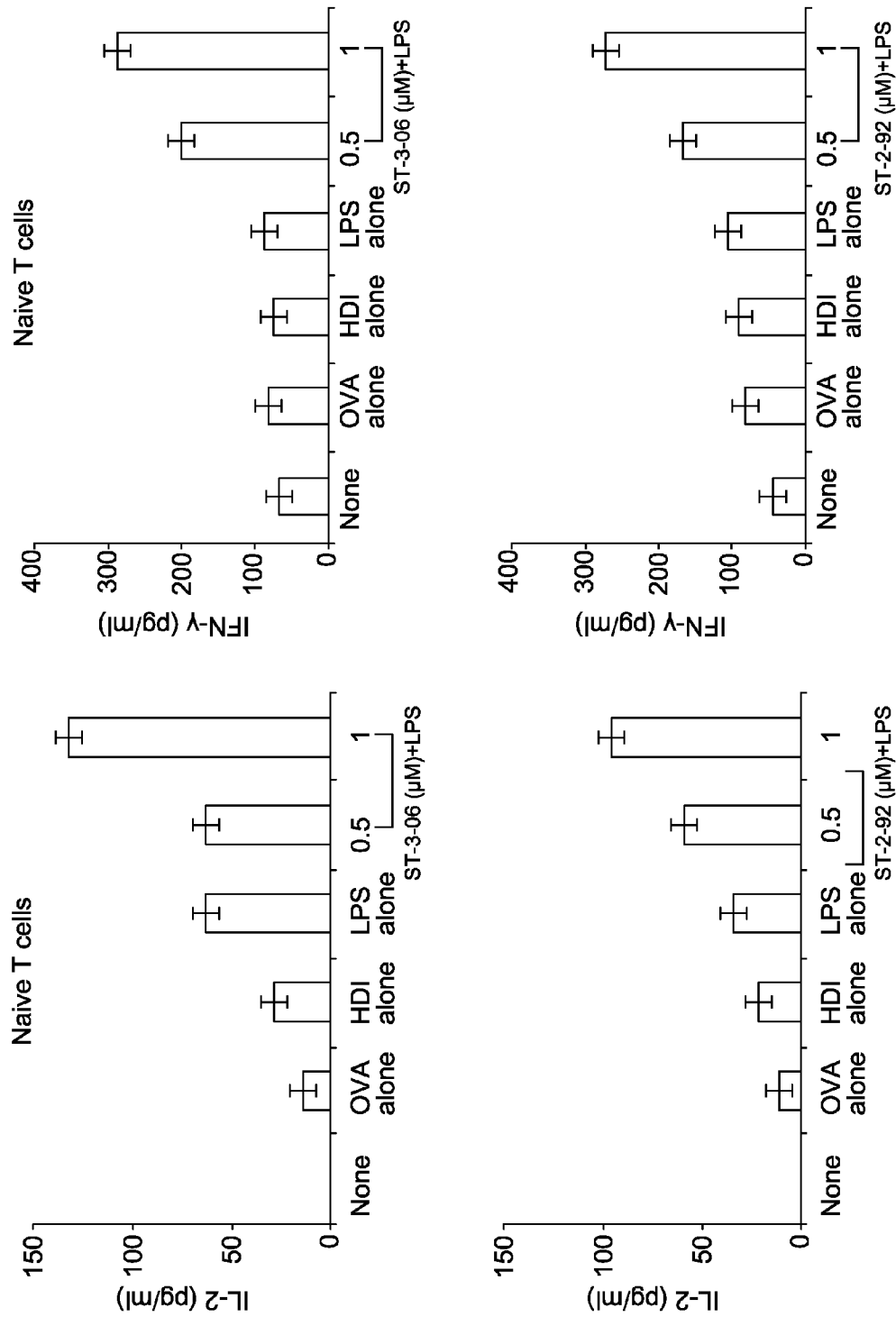
FIG. 33 is a series of images depicting the antigen-presenting function of FCmuMCLI cells treated with ST-3-06.
Figure 34:
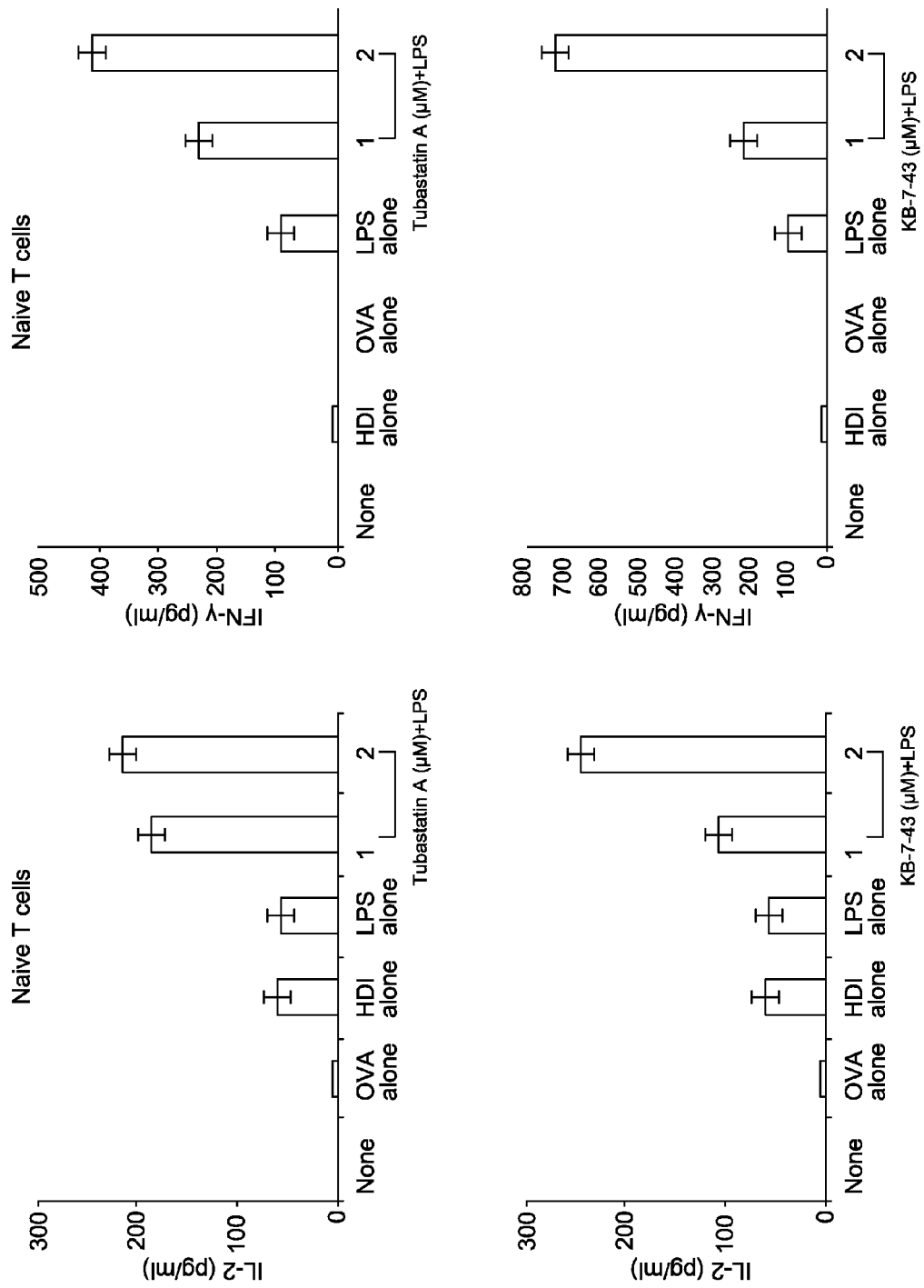
FIG. 34 is a senes of images depicting the antigen-presenting function of FCmuMCL1 cells treated with tubastatin A.
Figure 35:
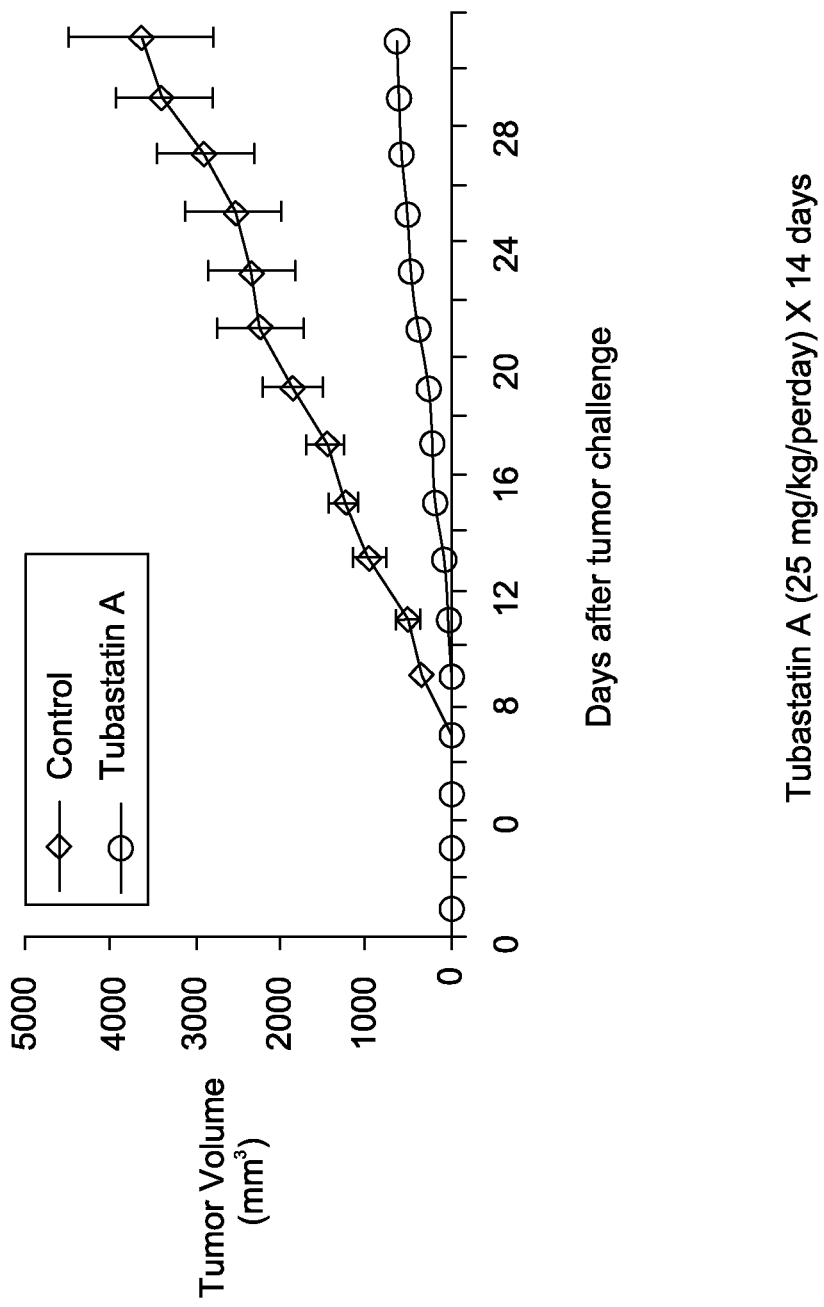
FIG. 35 is an image depicting the antitumor effect of tubastat in A in vivo.

FIG. 29 is an image depicting HDAC6 expression in human MCL. FIG. 30 is a series of images depicting the disruption of HDAC6 in human MCL cell lines. FIG. 31 is an image depicting the disruption of HDAC6 in murine FC-muMCLI cells. FIG. 32 is an image depicting the immunological effects of HDAC6 inhibition in MCL. Changes in MHC, costimulatory molecules and/or cytokine production in response to LPS or CpG+/− ST-3-06 or Tubastatin A are show. FIG. 33 is a series of images depicting the antigen presenting function of FC-muMCLI cells treated with ST-3-06. FIG. 34 is a series of images depicting the antigen-presenting function of FC-muMCLI cells treated with Tubastatin A. FIG. 35 is an image depicting the antitumor effect of tubastatin A in vivo. The data showed that HDAC6 inhibition augments the immunogenicity of MCL cells. HDAC6 is required for STAT3 activation in APCs and STAT3 diminishes the immunogenicity of tumor cells.

Figure 36:
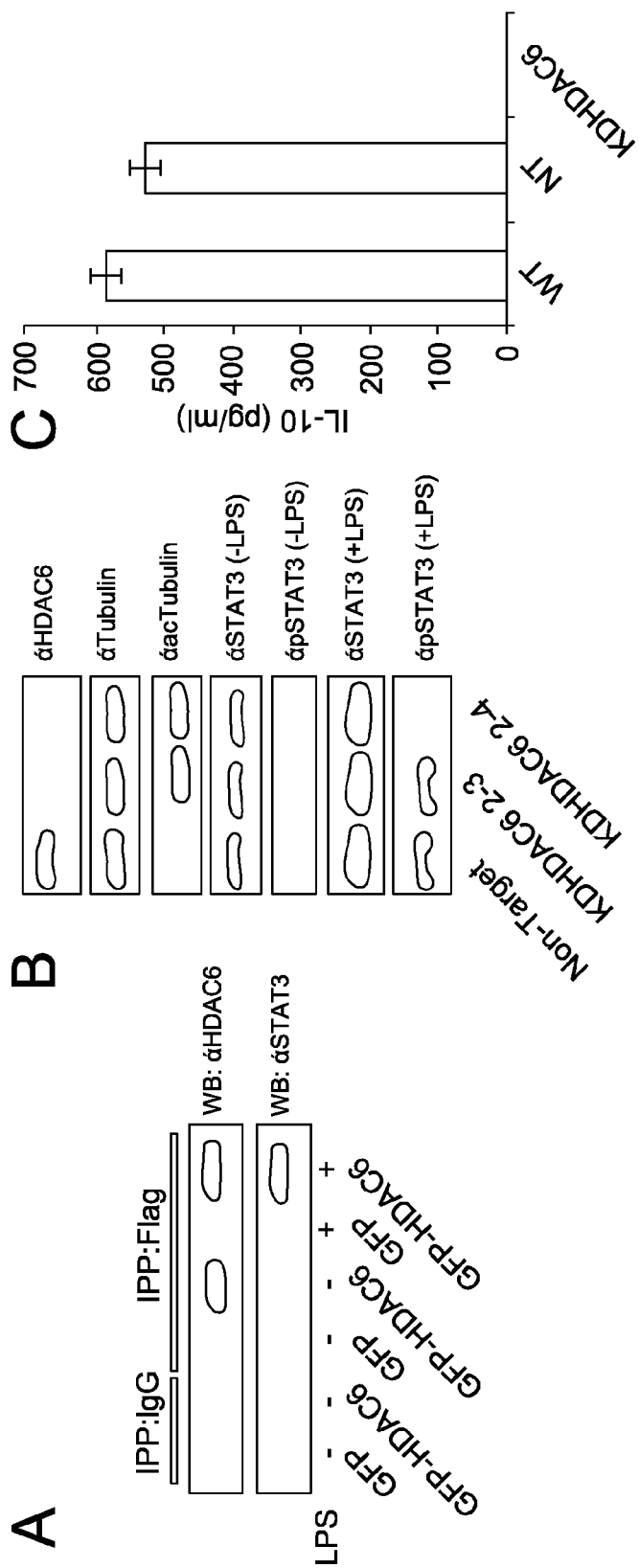
FIG. 36 is a series of images depicting the disruption of HDAC6 inhibits STAT3 phosphorylation in APCs.
Figure 38:
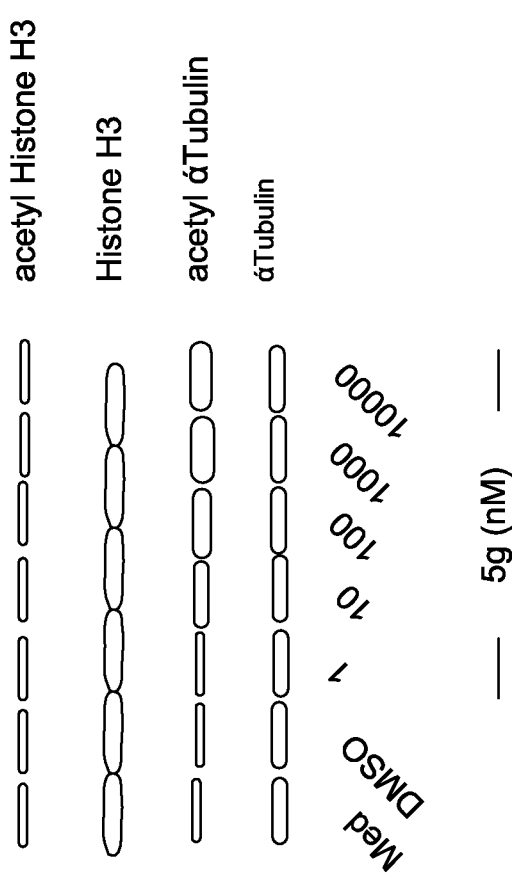
FIG. 38 is a Western blot showcasing substrate specificity of 5g.

FIG. 36 is a series of images depicting the disruption of HDAC6 inhibits STAT3 phosphorylation in APCs. The C-terminus of HDAC6 is required for interaction with HDAC 11. (A) Constructs of HDAC6 coding for different lengths of the proteins and carrying the FLAG epitope. (B) HDAC6 constructs were over-expressed in HeLa cells and their expression was evaluated by western blot using an anti-FLAG antibody or (C) immunoprecipatated to evaluate their interaction with HDAC 11.

FIG. 37 is a series of images depicting ST-3-06 decreased STAT3 phosphorylation and recruitment to the IL-10 gene promotor in APCs. Human MCL cells display an enhanced expression of HDAC6. Disruption of HDAC6 in malignant B-cells inhibits their proliferation and is associated with induction of apoptosis. Pharmacologic or genetic disruption of HDAC6 in MCL cells augment their antigen-presenting capabilities leading to better T-cell activation and restoration of function of anergic Tcells in vitro. In vivo treatment of MCL-bearing mice with Tubastatin-A is associated with a strong antitumor effect. Mechanistically, is has been have found that HDAC6 interacts with STAT3 in APCs. Disclosed herein is the rationale to use HDAC6 specific inhibitor(s) alone or in combination with STAT3 inhibitors in MCL.

Compositions, Formulations and Methods of Administration

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib. In other aspect, the disclosed compounds are coadministered with other HDAC inhibitors like ACY-1215, Tubacin, Tubastatin A, ST-3-06, OR ST-2-92.

In certain examples, compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, or hydrates thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Kits

The disclosed subject matter also concerns a packaged dosage formulation comprising in one or more containers at least one inhibitor compound or composition disclosed herein, e.g., any compound of Formulas I through II. A packaged dosage formulation can optionally comprise in one or more containers a pharmaceutically acceptable carrier or diluent. A packaged dosage formulation can also optionally comprise, in addition to an inhibitor compound or composition disclosed herein, other HDAC inhibitors, or an immunotherapeutic such as ipilimumab.

Depending upon the disorder or disease condition to be treated, a suitable dose(s) can be that amount that will reduce proliferation or growth of the target cell(s). In the context of cancer, a suitable dose(s) is that which will result in a concentration of the active agent in cancer tissue, such as a malignant tumor, which is known to achieve the desired response. The preferred dosage is the amount which results in maximum inhibition of cancer cell growth, without unmanageable side effects. Administration of a compound and/or agent can be continuous or at distinct intervals, as can be determined by a person of ordinary skill in the art.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

$^1$H and $^{13}$C spectra were obtained on a Bruker spectrometer with TMS as an internal standard. The following abbreviations for multiplicity were used: s=singlet, d=doublet, t=triplet, m=multiplet, dd=double doublet, br=broad. Reactions were monitored by TLC using precoated silica gel plates (Merck silica gel 60 $F_{254}$, 250 μm thickness) and visualized under UV light. LRMS experiments were carried out using an Agilent 1946A LC-MSD with MeCN and $H_2O$ spiked with 0.1% formic acid as mobile phase. HRMS determinations were done with a Shimadzu IT-TOF instrument with MeCN and $H_2O$ spiked with 0.1% formic acid as mobile phase. Flash chromatography was accomplished using the automated CombiFlash $R_f$ system from Teledyne ISCO and prepacked silica gel cartridges according to the recommended loading capacity.

Preparatory HPLC was used in purification of all final compounds using a Shimadzu preparative liquid chromatograph with the following specifications: Column: ACE 5AQ (150×21.2 mm) with 5 μm particle size. Method 1—25-100% MeOH/$H_2O$, 30 min; 100% MeOH, 5 min; 100-25% MeOH/$H_2O$, 4 min. Method 2—8-100% MeOH/$H_2O$, 30 min; 100% MeOH, 5 min; 100-8% MeOH/$H_2O$, 4 min.

Method 3—0% MeOH, 5 min; 0-100% MeOH/H$_2$O, 25 min; 100% MeOH, 5 min; 100-0% MeOH/H$_2$O, 4 min. Flow rate=17 mL/min with monitoring at 254 and 280 nm. Both solvents were spiked with 0.05% TFA. Analytical HPLC was carried out using an Agilent 1100 series instrument with the following specifications: column: Luna 5 C18(2) 100A (150×4.60 mm) 5 μm particle size; gradient—10-100% MeOH/H$_2$O, 18 min, 100% MeOH, 3 min; 100-10% MeOH/H$_2$O, 3 min; 10% MeOH/H$_2$O, 5 min. Both solvents were spiked with 0.05% TFA. The purity of all tested compounds was >95%, as determined by analytical HPLC.

All animal studies were performed in compliance with approved protocols by the IACUC at the University of South Florida. C57BL/6 mice were purchased from the NCI laboratories (Fredrick, Md., USA), and B6.CB17-Prkdc (scid)/SzJ immunodeficient mice were purchased from Jackson Laboratories (Bar Harbor, Mass., USA) For in vivo tumor studies, mice were injected subcutaneously into the shaved flank with 1.3×10$^5$ B16 melanoma cells suspended in 100 μL in PBS 1×.

B16-F10-luc murine melanoma cell line were obtained from the ATCC and cultured in RPMI 1640 supplemented with 10% FBS, 100 IU/mL Penicillin, and 100 μg/mL Streptomycin. The human melanocyte cell line, HEMn-LP, was obtained from Invitrogen and grow in Medium 254 supplemented with HMGS. Human melanoma cell lines were obtained from Dr. Smalley's Lab at Moffitt Cancer Center. All cell lines were grown under humidified conditions at 37° C. and 5% CO2.

Compound Synthesis: Making Reference to Scheme 1

Methyl 4-(((3-(dimethylamino)propyl)amino)methyl) benzoate (3a) The synthesis of 3a is representative, General Procedure A: A round-bottom flask charged with methyl 4-formyl benzoate (328 mg, 2 mmol) and 3-dimethylamino propylamine (0.252 mL, 2 mmol) was taken up in a solution of 5% AcOH in DCM (10 mL). After 5 minutes NaCNBH$_3$ (126 mg, 2 mmol) was added in portions and the resulting mixture was allowed to stir at room temperature under an atmosphere of Ar overnight. The reaction was quenched with 1N NaOH (10 mL) and the aqueous layer extracted with DCM (3×10 mL). The combined organic extracts were washed with brine, dried over sodium sulfate, concentrated in vacuo and purified via flash chromatography affording the product as a waxy solid (313 mg, 63%). $^1$H NMR (400 MHz, CDCl$_3$) δ 7.98 (d, J=8.0 Hz, 2H), 7.38 (d, J=8.0 Hz, 2H), 3.89 (s, 3H), 3.84 (s, 2H), 2.79 (br s, 1H), 2.68 (t, J=6.8 Hz, 2H), 2.35 (t, J=6.8 Hz, 2H), 2.23 (s, 6H), 1.70 (quint, J=6.8 Hz, 2H). $^{13}$C NMR (100 MHz, CDCl3) δ 166.96, 145.27, 129.71, 128.87, 127.95, 58.04, 53.42, 51.99, 47.87, 45.36, 27.41. LRMS ESI: [M+H]$^+$=251.1

Methyl 4-(((3-hydroxypropyl)amino)methyl)benzoate (3b Made according to General Procedure A affording a waxy solid (89 mg, 29%). $^1$H NMR (400 MHz, CDCl$_3$) δ 8.00 (d, J=8.0 Hz, 2H), 7.39 (d, J=8.0 Hz, 2H), 3.91 (s, 3H), 3.90 (s, 2H), 3.78 (broad, 4H), 2.93 (t, J=5.6 Hz, 2H), 1.78-1.73 (m, 2H). $^{13}$C NMR (100 MHz, CDCl$_3$) δ 166.79, 143.16, 129.77, 129.44, 128.26, 63.55, 53.14, 52.10, 48.88, 30.18. LRMS ESI: [M+H]$^+$=224.2.

Methyl 4-(((2-(1H-indol-3-yl)ethyl)amino)methyl)benzoate (3c) Made according to General Procedure A affording a waxy solid (446 mg, 72%). $^1$H NMR (400 MHz, CDCl$_3$) δ 8.28 (br s, 1H), 7.98 (d, J=8.0 Hz, 2H), 7.62 (d, J=7.6 Hz, 1H), 7.36-7.34 (m, 3H), 7.21 (t, J=7.6 Hz, 1H), 7.13 (t, J=7.6 Hz, 1H), 7.00 (s, 1H), 3.92 (s, 3H), 3.87 (s, 2H), 3.02-2.98 (m, 4H), 1.68 (br s, 1H). $^{13}$C NMR (100 MHz, CDCl$_3$) δ 167.06, 145.66, 136.34, 129.60, 128.62, 127.85, 127.31, 122.02, 121.89, 119.13, 118.74, 113.47, 111.15, 53.36, 51.97, 49.28, 25.64. LRMS ESI: [M+H]$^+$=309.1.

Methyl 4-(((4-hydroxyphenethyl)amino)methyl)benzoate (3d) Made according to General Procedure A affording a waxy solid (130 mg, 46%). $^1$H NMR (400 MHz, CDCl$_3$) δ 7.97 (d, J=8.0 Hz, 2H), 7.32 (d, J=8.0 Hz, 2H), 7.01 (d, J=8.4 Hz, 2H), 6.71 (d, J=8.4 Hz, 2H), 3.90 (s, 3H), 3.86 (s, 2H), 2.86 (t, J=6.8 Hz, 2H), 2.76 (t, J=6.8 Hz, 2H). $^{13}$C NMR (100 MHz, CDCl$_3$) δ 167.07, 154.60, 145.02, 131.05129.78, 129.75, 128.91, 128.04, 115.55, 53.29, 52.08, 50.37, 35.02. LRMS ESI: [M+H]$^+$=268.1.

Methyl 4-(((3-methoxypropyl)amino)methyl)benzoate (3e) Made according to General Procedure A affording a colorless oil (127 mg, 54%). $^1$H NMR (400 MHz, CDCl$_3$) δ 7.94 (d, J=8.0 Hz, 2H), 7.35 (d, J=8.0 Hz, 2H), 3.86 (s, 3H), 3.80 (s, 2H), 3.41 (t, J=6.4 Hz, 2H), 3.28 (s, 3H), 2.67 (t, J=6.4 Hz, 2H), 1.72 (m, 2H). $^{13}$C NMR (100 MHz, CDCl$_3$) δ 166.88, 145.78, 129.54, 128.58, 127.76, 71.17, 58.48, 53.50, 51.85, 46.72, 29.83. LRMS ESI: [M+H]$^+$=238.2.

Methyl 4-(((2-methoxyethyl)amino)methyl)benzoate (3f) Made according to General Procedure A affording a colorless oil (29 mg, 13%). $^1$H NMR (400 MHz, CDCl$_3$) δ 7.97 (d, J=8.0 Hz, 2H), 7.38 (d, J=8.0 Hz, 2H), 3.88 (s, 3H), 3.84 (s, 2H), 3.49 (t, J=5.2 Hz, 2H), 3.33 (s, 3H), 2.77 (t, J=5.2 Hz, 2H), 1.88 (br, 1H). $^{13}$C NMR (100 MHz, CDCl$_3$) δ 166.98, 145.58, 129.65, 128.74, 127.90, 71.85, 58.74, 53.47, 51.94, 48.69. LRMS ESI: [M+H]$^+$=224.2.

Methyl 4-((butylamino)methyl)benzoate (3g) Made according to General Procedure A affording colorless oil (150 mg, 68%). $^1$H NMR (400 MHz, CDCl$_3$) δ 7.99 (d, J=8.0 Hz, 2H), 7.39 (d, J=8.0 Hz, 2H), 3.91 (s, 3H), 3.84 (s, 2H), 2.62 (t, J=7.2 Hz, 2H), 1.49 (m, 2H), 1.34 (m, 3H), 0.91 (t, J=7.2 Hz, 3H). $^{13}$C NMR (100 MHz, CDCl$_3$) δ 167.00, 145.89, 129.65, 128.70, 127.87, 53.63, 51.95, 49.14, 32.14, 20.38, 13.93. LRMS ESI: [M+H]$^+$=222.1.

Methyl 4-((phenethylamino)methyl)benzoate (3h) Made according to General Procedure A affording a colorless oil (203 mg, 75%). 1H NMR (400 MHz, CDCl3) δ 8.01 (m, 2H), 7.35 (m, 4H), 7.22 (m, 3H), 3.93 (s, 3H), 3.88 (s, 2H), 2.89 (m, 4H). 13C NMR (100 MHz, CDCl3) δ 166.97, 145.66, 139.81, 129.65, 128.65, 128.43, 127.82, 126.15, 53.38, 51.96, 50.46, 36.29. LRMS ESI: [M+H]$^+$=270.1.

Methyl 4-((1-(3-(dimethylamino)propyl)-3-(2-methoxyphenyl)ureido)methyl)-benzoate (4a) The synthesis of 4a is representative, General Procedure B. A solution of 3a (99 mg, 0.395 mmol) in DCM (5 mL) was added the appropriate isocyante (0.053 mL, 0.395 mmol) at room temperature under and atmosphere of Ar and the resulting solution was allowed to stir overnight. The reaction was quenched with saturated bicarbonate (10 mL) and extracted with DCM (3×10 mL). The combined organics were washed with brine (15 mL), dried over sodium sulfate, concentrated in vacuo and purified via flash chromatography affording the urea ester as a waxy solid (156 mg, 98%). $^1$H NMR (400 MHz, CDCl$_3$) δ 8.64 (br s, 1H), 8.18 (d, J=7.2 Hz, 1H), 7.99 (d, J=8.0 Hz, 2H), 7.40 (d, J=8.0 Hz, 2H), 6.97-6.94 (m, 2H), 6.84 (d, J=7.2 Hz, 1H), 4.64 (s, 2H), 3.91 (s, 3H), 3.81 (s, 3H), 3.42 (t, J=6.0 Hz, 2H), 2.34 (t, J=6.0 Hz, 2H), 2.20 (s, 6H), 1.74 (quint, J=6.0 Hz, 2H). $^{13}$C NMR (100 MHz, CDCl$_3$) δ 166.85, 156.64, 148.86, 143.75, 129.77, 129.43, 129.02, 127.53, 122.25, 120.94, 120.36, 109.92, 55.52, 54.60, 51.96, 49.19, 44.64, 44.18, 24.98. LRMS ESI: [M+H]$^+$=400.2.

Methyl 4-((1-(3-hydroxypropyl)-3-(2-methoxyphenyl) ureido)methyl)benzoate (4b)
Made according to General Procedure B affording a waxy solid (113 mg, 74%). $^1$H NMR (400 MHz, CDCl$_3$) δ

8.07-8.03 (m, 3H), 7.39 (d, J=8.0 Hz, 2H), 7.20 (br s, 1H), 6.93-6.90 (m, 2H), 6.77-6.47 (m, 1H), 4.59 (s, 2H), 3.91 (s, 3H), 3.67-3.62 (m, 7H), 1.80-1.77 (m, 2H). $^{13}$C NMR (100 MHz, CDCl$_3$) δ 166.65, 156.31, 147.85, 142.24, 130.14, 129.70, 128.43, 126.77, 122.44, 121.04, 119.48, 109.88, 58.25, 55.53, 52.12, 50.41, 44.00, 30.32. LRMS ESI: [M+H]$^+$=373.2.

Methyl 4-((1-(2-(1H-indol-3-yl)ethyl)-3-(2-methoxyphenyl)ureido)methyl)-benzoate (4c) Made according to General Procedure B affording a solid (200 mg, 95%). $^1$H NMR (400 MHz, CDCl$_3$) δ 8.23-8.21 (m, 1H), 8.15 (br s, 1H), 7.99 (d, J=8.0 Hz, 2H), 7.60 (d, J=7.6 Hz, 1H), 7.36-7.34 (m, 3H), 7.22-7.10 (m, 3H), 7.02 (s, 1H), 6.97-6.94 (m, 2H), 6.81-6.79 (m, 1H), 4.59 (s, 2H), 3.91 (s, 3H), 3.70-3.67 (m, 5H), 3.12 (t, J=7.6 Hz, 2H). $^{13}$C NMR (100 MHz, CDCl$_3$) δ 166.83, 155.17, 147.60, 143.28, 136.29, 129.98, 129.34, 128.79, 127.30, 127.13, 122.18, 122.08, 121.15, 119.51, 118.96, 118.46, 112.53, 111.29, 109.29, 55.56, 52.10, 50.89, 48.98. LRMS ESI: [M+H]$^+$=458.2.

Methyl 4-((1-(4-hydroxyphenethyl)-3-(2-methoxyphenyl)ureido)methyl)-benzoate (4d) Made according to General Procedure B affording a solid (178 mg, 90%). $^1$H NMR (400 MHz, CDCl$_3$) δ 8.15 (d, J=4.8 Hz, 1H), 8.01 (d, J=7.6 Hz, 2H), 7.35 (d, J=8.0 Hz, 2H), 7.11 (s, 1H), 7.02 (d, J=8.0 Hz, 2H), 6.95-6.93 (m, 2H), 6.80-6.77 (m, 3H), 6.43 (br s, 1H), 4.53 (s, 2H), 3.91 (s, 3H), 3.73 (s, 3H), 3.56 (t, J=6.8 Hz, 2H), 2.87 (t, J=6.8 Hz, 2H). $^{13}$C NMR (100 MHz, CDCl$_3$) δ 166.89, 155.25, 154.99, 147.69, 142.93, 130.04, 129.83, 129.76, 129.40, 128.50, 127.21, 122.35, 121.18, 119.10, 115.67, 109.78, 55.60, 52.15, 50.97, 50.33, 33.88. LRMS: [M+H]$^+$=435.2.

Methyl 4-((1-(3-methoxypropyl)-3-phenylureido)methyl)benzoate (4e) Made according to General Procedure B affording a colorless oil (70 mg, 73%). $^1$H NMR (400 MHz, CDCl$_3$) δ 8.00 (d, J=8.4 Hz, 2H), 7.84 (s, 1H), 7.45 (d, J=8.4. Hz, 2H), 7.40 (d, J=8.0 Hz, 2H), 7.30 (m, 2H), 7.02 (t, J=7.6 Hz, 1H), 4.64 (s, 2H), 3.92 (s, 3H), 3.49 (t, J=5.2 Hz, 2H), 3.44 (s, 3H), 3.415 (t, J=6.4 Hz, 2H), 1.77 (m, 2H). $^{13}$C NMR (100 MHz, CDCl$_3$) δ 166.87, 156.36, 143.76, 139.85, 129.88, 129.18, 128.81, 127.72, 122.45, 119.17, 68.16, 58.63, 52.05, 49.41, 43.05, 27.55. LRMS ESI: [M+H]$^+$=358.2.

Methyl 4-((1-(2-methoxyethyl)-3-phenylureido)methyl)benzoate (4f) Made according to General Procedure B affording a colorless oil (40 mg, 91%). $^1$H NMR (400 MHz, CDCl$_3$) δ 8.33 (br, 1H), 8.02 (d, J=8.0 Hz, 2H), 7.35 (m, 6H), 7.02 (t, J=7.2 Hz, 1H), 4.68 (s, 2H), 3.93 (s, 3H), 3.50 (s, 3H), 3.46 (s, 4H). $^{13}$C NMR (100 MHz, CDCl$_3$) δ 166.88, 157.07, 143.81, 139.37, 129.92, 129.28, 128.81, 127.73, 122.34, 119.15, 72.59, 59.28, 52.07, 50.90, 48.44. LRMS ESI: [M+H]$^+$=343.2.

Methyl 4-((1-butyl-3-phenylureido)methyl)benzoate (4g) Made according to General Procedure B affording colorless oil (59 mg, 98%). $^1$H NMR (400 MHz, CDCl$_3$) δ 8.04 (d, J=8.0 Hz, 2H), 7.39 (d, J=8.0 Hz, 2H), 7.27 (m, 4H), 7.03 (t, J=7.2 Hz, 1H), 6.32 (s, 1H), 4.65 (s, 2H), 3.93 (s, 3H), 3.36 (t, J=7.2 Hz, 2H), 1.64 (m, 2H), 1.37 (m, 2H), 0.96 (t, J=7.2 Hz, 3H). $^{13}$C NMR (100 MHz, CDCl$_3$) δ 166.74, 155.30, 143.11, 138.83, 130.14, 129.50, 128.85, 127.04, 123.16, 119.90, 52.12, 50.49, 47.74, 30.52, 20.18, 13.81. LRMS ESI: [M+H]$^+$=341.1

Methyl 4-((1-phenethyl-3-phenylureido)methyl)benzoate (4h) Made according to General Procedure B affording a colorless oil (113 mg, 92%). $^1$H NMR (400 MHz, CDCl$_3$) δ 8.02 (d, J=8.4 Hz, 2H), 7.36 (m, 4H), 7.30 (d, J=7.2 Hz, 1H), 7.21 (m, 4H), 7.08 (d, J=8.0 Hz, 2H), 6.99 (t, J=7.2 Hz, 1H), 6.00 (s, 1H), 4.58 (s, 2H), 3.91 (s, 3H), 3.59 (t, J=6.8 Hz, 2H), 2.90 (t, J=6.8 Hz, 2H). $^{13}$C NMR (100 MHz, CDCl$_3$) δ 166.71, 155.61, 142.99, 138.86, 138.72, 130.06, 129.43, 129.00, 128.86, 128.65, 127.28, 126.92, 122.95, 119.83, 52.08, 50.38, 49.94, 34.74. LRMS ESI: [M+H]$^+$=389.2.

4-((1-(3-(dimethylamino)propyl)-3-(2-methoxyphenyl)ureido)methyl)-N-hydroxybenzamide (5a) The synthesis of 5a is representative, General Procedure C. Solid NaOH (125 mg, 3.12 mmol) was dissolved in an aq. solution (50% wt, 1 mL) at 0° C. Then a solution of 4a (156 mg, 0.390 mmol) in THF/MeOH (1:1, 6 mL total) was added dropwise where the biphasic solution became homogenous upon compete addition. The resulting solution was allowed to stir 30 min at room temperature. The reaction was quenched with AcOH (0.223 mL, 3.90 mmol) and concentrated in vacuo, and the crude product was purified via HPLC Method 2 and neutralized with bicarbonate wash affording the title compound (20 mg, 13%). $^1$H NMR (400 MHz, DMSO-d$_6$) δ 11.22 (br s, 1H), 9.02 (br s, 1H), 7.80-7.76 (m, 3H), 7.39 (d, J=8.4 Hz, 2H), 7.00-6.94 (m, 2H), 6.88-6.84 (m, 2H), 4.62 (s, 2H), 3.72 (s, 3H), 3.43-3.40 (m, 2H), 2.82 (br s, 2H), 2.56 (s, 6H), 1.91-1.86 (m, 2H). $^{13}$C NMR (100 MHz, DMSO-d$_6$) δ 155.35, 149.62, 141.56, 131.69, 128.60, 127.24, 127.15, 127.02, 123.14, 121.40, 120.23, 110.78, 55.62, 54.33, 49.32, 44.24, 42.76, 23.45. HRMS ESI: calc. for C$_{21}$H$_{28}$N$_4$O$_4$ [M+H]$^+$ m/z=401.2183. found 401.2164.

N-hydroxy-4-((1-(3-hydroxypropyl)-3-(2-methoxyphenyl)ureido)methyl)-benzamide (5b) Made according to General Procedure C and purified via Method 3 affording the title compound (95 mg, 84%). $^1$H NMR (400 MHz, DMSO-d$_6$) δ 11.19 (br s, 1H), 7.82 (d, J=7.6 Hz, 1H), 7.76-7.71 (m, 3H), 7.37 (d, J=8.0 Hz, 2H), 6.95 (d, J=4.0 Hz, 2H), 6.88-06.85 (m, 1H), 4.58 (s, 2H), 3.74 (s, 3H), 3.48 (t, J=5.6 Hz, 2H), 3.40 (t, J=6.8 Hz, 2H), 1.73-1.69 (m, 2H). $^{13}$C NMR (100 MHz, DMSO-d$_6$) δ 164.10, 155.18, 149.08, 141.99, 131.56, 128.91, 127.18, 127.10, 126.93, 122.61, 120.49, 120.29, 110.76, 57.59, 55.69, 49.28, 43.97, 30.61. HRMS ESI: calc. for C$_{19}$H$_{23}$N$_3$O$_5$ [M+H]$^+$ m/z=374.1710. found 374.1693.

4-((1-(2-(1H-indol-3-yl)ethyl)-3-(2-methoxyphenyl)ureido)methyl)-N-hydroxybenzamide (5c) Made according to General Procedure C and purified via Method 1 affording the title compound (62 mg, 57%). $^1$H NMR (400 MHz, DMSO-d$_6$) δ 11.21 (br s, 1H), 10.86 (s, 1H), 10.12 (br s, 1H), 7.86 (t, J=7.6 Hz, 1H), 7.75 (d, J=8.0 Hz, 2H), 7.56 (d, J=8.0 Hz, 1H), 7.42-7.40 (m, 3H), 7.34 (d, J=8.0 Hz, 1H), 7.18 (s, 1H), 7.07 (t, J=7.2 Hz, 1H), 7.01-6.96 (m, 3H), 6.90-6.86 (m, 1H), 4.64 (s, 2H), 3.71 (s, 3H), 3.62 (t, J=7.6 Hz, 2H), 3.00 (t, J=7.6 Hz, 2H). $^{13}$C NMR (100 MHz, DMSO-d$_6$) δ 163.97, 158.37, 154.72, 148.88, 141.90, 136.21, 131.65, 128.70, 127.12, 122.98, 122.65, 120.97, 120.35, 118.31, 118.18, 111.41, 111.11, 110.66, 55.66, 49.77, 48.47, 23.89. HRMS ESI: calc. for C$_{26}$H$_{26}$N$_4$O$_4$ [M+H]$^+$ m/z=459.2027. found 459.2030.

N-hydroxy-4-((1-(4-hydroxyphenethyl)-3-(2-methoxyphenyl)ureido)methyl)-benzamide (5d) Made according to General Procedure C and purified via Method 2 affording the title compound (63 mg, 63%). $^1$H NMR (400 MHz, DMSO-d$_6$) δ 11.20 (br s, 1H), 9.20 (br s, 1H), 7.82 (d, J=8.0 Hz, 2H), 7.74 (d, J=8.0 Hz, 2H), 7.38 (d, J=8.4 Hz, 2H), 7.37 (s, 1H), 7.04 (d, J=8.4 Hz, 2H), 6.98 (d, J=8.0 Hz, 2H), 6.89-6.85 (m, 1H), 6.69 (d, J=8.4 Hz, 2H), 4.57 (s, 2H), 3.75 (s, 3H), 3.49 (t, J=7.6 Hz, 2H), 2.75 (t, J=7.6 Hz, 2H). $^{13}$C NMR (100 MHz, DMSO-d$_6$) δ 164.00, 155.76, 154.62, 148.97, 141.88, 131.63, 129.63, 128.83, 127.12, 122.72, 120.44, 120.33, 115.22, 110.69, 55.69, 49.68, 49.49, 33.21. HRMS ESI: calc. for C$_{24}$H$_{25}$N$_3$O$_5$ [M+H]$^+$ m/z=436.1867. found 436.1858.

N-hydroxy-4-((1-(3-methoxypropyl)-3-phenylureido)methyl)benzamide (5e) Made according to General Procedure C and purified via Method 2 affording the title compound (48 mg, 76%). $^1$H NMR (400 MHz, DMSO-$d_6$) δ 11.19 (br, 1H), 8.36 (s, 1H), 7.72 (d, J=8.4 Hz, 2H), 7.45 (d, J=7.6 Hz, 2H), 7.32 (d, J=8.4 Hz, 2H), 7.23 (m, 2H), 6.94 (t, J=7.2 Hz, 1H), 4.61 (s, 2H), 3.34 (m, 4H), 3.21 (s, 3H), 1.74 (m, 2H). $^{13}$C NMR (100 MHz, DMSO-$d_6$) δ164.04, 155.30, 142.25, 140.42, 131.49, 128.31, 127.06, 121.87, 119.88, 69.16, 57.88, 49.08, 43.56, 27.81. HRMS ESI: calc. for $C_{19}H_{23}N_3O_4$ [M+H]$^+$ m/z=358.1761. found 358.1785.

N-hydroxy-4-((1-(2-methoxyethyl)-3-phenylureido)methyl)benzamide (5f) Made according to General Procedure C and purified Method 2 affording the title compound (20 mg, 50%). $^1$H NMR (400 MHz, DMSO-$d_6$) δ 11.17 (s, 1H), 9.01 (br, 1H), 8.44 (s, 1H), 7.72 (d, J=8.0 Hz, 2H), 7.42 (d, J=7.6 Hz, 2H), 7.32 (d, J=8.0 Hz, 2H), 7.23 (t, J=7.6 Hz, 2H)H, 6.94 (t, J=7.2 Hz, 1H), 4.64 (s, 2H), 3.49 (s, 4H), 3.28 (s, 3H). $^{13}$C NMR (100 MHz, DMSO-$d_6$) δ 164.06, 155.46, 142.17, 140.30, 131.43, 128.32, 126.97, 121.83, 119.64, 70.88, 58.31, 49.82, 46.35. HRMS ESI: calc. for $C_{18}H_{21}N_3O_4$ [M+H]$^+$ m/z=344.1605. found 344.1601.

4-((1-butyl-3-phenylureido)methyl)-N-hydroxybenzamide (5g) Made according to General Procedure C and purified by Method 2 affording the title compound (40 mg, 68%). $^1$H NMR (400 MHz, DMSO-$d_6$) δ 11.17 (br, 1H), 8.36 (s, 1H), 7.72 (d, J=8.0 Hz, 2H), 7.46 (d, J=7.6 Hz, 2H), 7.32 (d, J=8.0 Hz, 2H), 7.22 (t, J=7.6 Hz, 2H), 6.94 (t, J=7.2 Hz, 1H), 4.62 (s, 2H), 3.30 (m, 1H), 1.48 (m, 2H), 1.27 (m, 2H), 0.86 (t, J=7.6 Hz, 3H). $^{13}$C NMR (100 MHz, DMSO-$d_6$) δ 164.01, 155.22, 142.30, 140.45, 131.42, 128.19, 127.00, 126.96, 121.80, 120.04, 49.01, 46.11, 29.64, 19.43, 13.77. HRMS ESI: calc. for $C_{19}H_{23}N_3O_3$ [M+H]$^+$ m/z=342.1812. found 342.1802.

N-hydroxy-4-((1-phenethyl-3-phenylureido)methyl)benzamide (5h) Made according to General Procedure C and purified by Method 2 affording the title compound (71 mg, 63%). $^1$H NMR (400 MHz, DMSO-$d_6$) δ 11.15 (br, 1H), 7.72 (d, J=8.0 Hz, 2H), 7.45 (d, J=8.0 Hz, 2H), 7.31 (d, J=8.0 Hz, 2H), 7.24 (m, 7H), 6.95 (t, J=7.2 Hz, 1H), 4.60 (s, 2H), 3.54 (t, J=7.6 Hz, 2H), 2.82 (t, J=7.6 Hz, 2H). $^{13}$C NMR (100 MHz, DMSO-$d_6$) δ 164.04, 155.12, 142.12, 140.35, 139.04, 131.50, 128.77, 128.31, 128.20, 127.09, 127.05, 126.16, 121.91, 120.13, 49.20, 48.04, 33.91. HRMS ESI: calc. for $C_{23}H_{23}N_3O_3$ [M+H]$^+$ m/z=390.1812. found 390.1793.

Compound Synthesis: Making Reference to Scheme 2

N-butylaniline (6a) Was synthesized in an analogous manner previously reported (Org Lett, 4, 581).[11] Briefly, CuI (19 mg, 0.1 mmol) and freshly ground $K_3PO_4$ (849 mg, 4 mmol) were placed in a sealed tube followed by sequential addition of isopropanol (2 mL), ethylene glycol (0.222 mL, 4.0 mL), phenyl-iodide (0.224 mL, 2.0 mmol) and n-butylamine (0.237 mL, 2.4 mmol). The tube was then sealed and stirring commenced at 80° C. for 18 h. After cooling to room temperature the reaction was diluted with water:ethyl ether (1:1, 10 mL). The aqueous layer was extracted with ether (3×5 mL), washed with brine (15 mL), dried over sodium sulfate and concentrated in vacuo. Purification via flash chromatography afforded the title compound as a yellow oil (235 mg, 79%). $^1$H NMR (400 MHz, CDCl$_3$) δ 7.19 (m, 2H), 6.70 (t, J=7.2 Hz, 1H), 6.61 (d, J=8.4 Hz, 2H), 3.60 (br, 1H), 3.12 (t, J=7.2 Hz, 2H), 1.62 (m, 2H), 1.44 (m, 2H), 0.98 (t, J=7.2 Hz, 3H). Spectra matches that reported in Okano et al., "Synthesis of secondary arylamines through copper-mediated intermolecular aryl amination," *Org Lett* 2003, 5(26):4987-4990.

N-(3-methoxypropyl)aniline (6b) Made following the same procedure for 6a affording a light yellow oil (282 mg, 85%). $^1$H NMR (400 MHz, CDCl$_3$) δ 7.18 (m, 2H), 6.69 (t, J=7.2 Hz, 1H), 6.61 (d, J=8.4 Hz, 2H), 3.92 (br, 1H), 3.52 (t J=6.0 Hz, 2H), 3.60 (s, 3H), 3.23 (t, J=6.8 Hz, 2H), 1.90 (m, 2H). Spectra matches that reported in Guo et al., Efficient Iron-Catalyzed N-Arylation of Aryl Halides with Amines," *Org Lett* 2008, 10(20):4513-4516.

Methyl 4-((3-butyl-3-phenylureido)methyl)benzoate (7a) Methyl 4-(aminomethyl)benzoate hydrochloride (101 mg, 0.5 mmol) was taken up in a biphasic solution of DCM:sat. bicarbonate (1:1, 4 mL) and added triphosgene (49 mg, 0.17 mmol) at 0° C. After 30 min, the aqueous layer was extracted with DCM (3×5 mL), washed with brine (15 mL) and concentrated in vacuo. The crude isocyante was taken up in DCM (2 mL) and added 6a (75 mg, 0.5 mmol) and Et$_3$N (0.209 mL, 1.5 mmol) and resulting solution allowed to stir overnight at room temperature. The reaction was quenched with sat. bicarbonate (5 mL) and extracted with DCM (3×5 mL). The combined organics were washed with brine (15 mL), dried over sodium sulfate, concentrated in vacuo. The crude material was purified via flash chromatography affording the title compound as an off-white waxy solid (93 mg, 55%). $^1$H NMR (400 MHz, CDCl$_3$) δ 7.95 (d, J=8.0 Hz, 2H), 7.42 (t, J=7.6 Hz, 2H), 7.32 (m, 1H), 7.25 (m, 4H), 4.45 (t, J=5.6 Hz, 1H), 4.41 (d, J=6.0 Hz, 2H), 3.89 (s, 3H), 3.70 (t, J=7.6 Hz, 2H), 1.48 (m, 2H), 1.31 (m, 2H), 0.89 (t, 7.2 Hz, 3H). $^{13}$C NMR (100 MHz, CDCl$_3$) δ 166.89, 156.87, 145.14, 141.61, 130.08, 129.78, 128.85, 128.73, 127.81, 126.96, 52.01, 49.21, 44.25, 30.68, 19.92, 13.82. LRMS ESI: [M+H]$^+$=341.1.

Methyl 4-((3-(3-methoxypropyl)-3-phenylureido)methyl)benzoate (7b) Made according to that of 7a except using 6b as the secondary amine affording the title compound as an off-white waxy solid (65 mg, 36%). $^1$H NMR (400 MHz, CDCl$_3$) δ 7.96 (d, J=8.0 Hz, 2H), 7.43 (t, J=7.6 Hz, 2H), 7.33 (m, 1H), 7.27 (m, 4H), 4.69 (br, 1H), 4.42 (6.0 Hz, 2H), 3.90 (s, 3H), 3.80 (t, J=7.2 Hz, 2H), 3.43 (t, J=6.4 Hz, 2H), 3.27 (s, 3H), 1.83 (m, 2H). $^{13}$C NMR (100 MHz, CDCl$_3$) δ 166.88, 156.95, 145.05, 141.63, 130.10, 129.80, 128.90, 127.79, 127.00, 70.23, 58.54, 52.03, 46.86, 44.29, 28.82. LRMS ESI: [M+H]$^+$=357.1.

Methyl 4-((3-ethyl-3-phenylureido)methyl)benzoate (7c) Made according to that of 7a except using commercially available N-ethylaniline as the secondary amine affording the title compound as an off-white waxy solid (197 mg, 63%). $^1$H NMR (400 MHz, CDCl$_3$) δ 7.94 (d, J=8.4 Hz, 2H), 7.24 (t, J=7.6 Hz, 2H), 7.32 (t, J=7.2 Hz, 1H), 7.26 (m, 4H), 4.57 (br, 1H), 4.41 (d, J=5.6 Hz, 1H), 3.88 (s, 3H), 3.76 (dd, J=14, 7.2 Hz, 2H), 1.12 (t, J=7.2 Hz, 3H). $^{13}$C NMR (100 MHz, CDCl$_3$) δ 166.82, 156.64, 145.09, 141.22, 130.03, 129.72, 128.79, 127.82, 126.92, 51.95, 44.17, 44.09, 13.82. LRMS ESI: [M+H]$^+$=313.1.

4-((3-butyl-3-phenylureido)methyl)-N-hydroxybenzamide (8a) Made according to General Procedure C and purified by Method 2 affording the title compound as an off-white solid (74 mg, 80%). $^1$H NMR (400 MHz, DMSO-$d_6$) δ 11.13 (br, 1H), 8.72 (br, 1H), 7.66 (d, J=8.0 Hz, 2H), 7.43 (t, J=7.6 Hz, 2H), 7.27 (m, 5H), 6.23 (t, J=5.6 Hz, 1H), 4.20 (d, J=5.6 Hz, 2H), 3.57 (t, J=6.8 Hz, 2H), 1.35 (m, 2H), 1.23 (m, 2H), 0.82 (t, J=6.8 Hz, 3H). $^{13}$C NMR (100 MHz, DMSO-$d_6$) δ 164.17, 156.48, 144.50, 142.12, 130.129.55, 128.22, 126.67, 126.61, 48.44, 43.38, 30.21, 19.35, 13.72. HRMS ESI: calc. for $C_{19}H_{23}N_3O_3$ [M+H]$^+$ m/z=342.1812. found 342.1825.

N-hydroxy-4-((3-(3-methoxypropyl)-3-phenylureido) methyl)benzamide (8b) Made according to General Procedure C and purified by Method 2 affording an off-white solid (59 mg, 91%). $^1$H NMR (400 MHz, DMSO-$d_6$) δ 11.14 (br, 1H), 7.66 (d, J=8.0 Hz, 2H), 7.43 (t, J=7.6 Hz, 2H), 7.27 (m, 5H), 6.27 (t, J=6.0 Hz, 1H), 4.21 (d, J=5.8 Hz, 2H), 3.62 (t, J=7.2 Hz, 2H), 3.28 (t, J=6.4 Hz, 2H), 3.14 (s, 3H), 1.63 (m, 2H). $^{13}$C NMR (100 MHz, DMSO-$d_6$) δ 164.13, 156.51, 144.44, 142.19, 130.89, 129.57, 128.18, 126.70, 126.64, 69.49, 57.80, 46.35, 43.39, 28.32. HRMS ESI: calc. for $C_{19}H_{23}N_3O_4$ [M+H]$^+$ m/z=358.1761. found 358.1749.

4-((3-ethyl-3-phenylureido)methyl)-N-hydroxybenzamide (8c) Made according to General Procedure C and purified by Method 2 affording an off-white solid (91 mg, 96%). $^1$H NMR (400 MHz, DMSO-$d_6$) δ 11.13 (br, 1H), 7.67 (d, J=8.0 Hz, 2H), 7.43 (t, J=7.6 Hz, 2H), 7.26 (m, 5H), 6.30 (t, J=6.0 Hz, 1H), 4.21 (d, J=5.6 Hz, 2H), 3.61 (dd, J=14, 7.2 Hz, 2H), 0.99 (t, J=7.2 Hz, 3H). $^{13}$C NMR (100 MHz, DMSO-$d_6$) δ 164.21, 156.34, 144.54, 142.00, 130.92, 129.57, 128.32, 126.75, 126.67, 43.70, 43.39, 13.76. HRMS ESI: calc. for $C_{17}H_{19}N_3O_3$ [M+H]$^+$ m/z=314.1499. found 314.1489.

4-((1-butyl-3-(1H-indazol-6-yl)ureido)methyl)-N-hydroxybenzamide (JB7-19) was synthesized according to Scheme 4.

Scheme 4

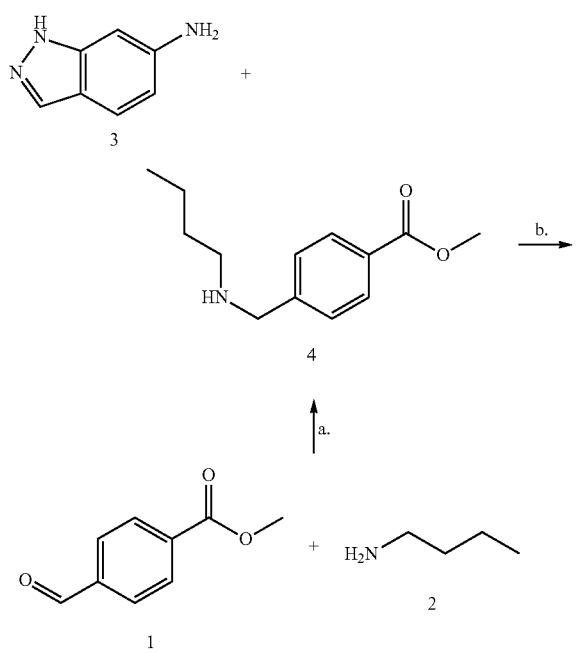

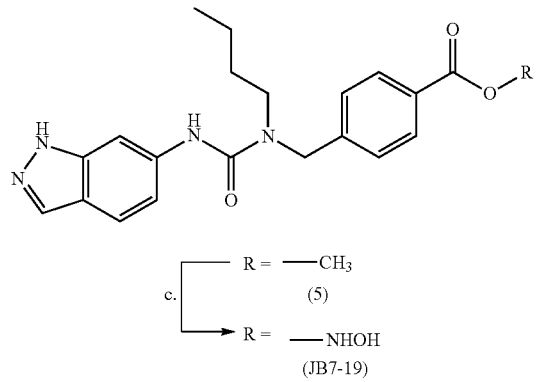

Reagents and Conditions: a.) NaBH$_3$CN, MeOH; b.) i. 3, PhOCOCl, DIEA, THF; ii. 4, K$_2$CO$_3$, DMF; c.) aq. NH$_2$OH, NaOH, THF:MeOH (1:1).

To make compounds 4-((1-butyl-3-(pyrimidin-2-yl) ureido)methyl)-N-hydroxybenzamide (JB6-22) and 4-((1-butyl-3-(dimethylamino)ureido)methyl)-N-hydroxybenzamide (JB7-20), substitute compound 3 in Scheme 4 with pyrimidin-2-amine and dimethylaminoaniline, respectively.

HDAC Inhibition Assays

HDAC inhibition assays were performed by Reaction Biology Corp. (Malvern, Pa.) using isolated human, recombinant full-length HDAC1 and -6 from a baculovirus expression system in Sf9 cells. An acetylated fluorogenic peptide, RHKK$_{Ac}$, derived from residues 379-382 of p53 was used as substrate. The reaction buffer was made up of 50 mM Tris-HCl pH 8.0, 127 mM NaCl, 2.7 mM KCl, 1 mM MgCl$_2$, 1 mg/mL BSA, and a final concentration of 1% DMSO. Compounds were delivered in DMSO and delivered to enzyme mixture with preincubation of 5-10 min followed by substrate addition and incubation for 2 h at 30° C. Trichostatin A and developer were added to quench the reaction and generate fluorescence, respectively. Dose-response curves were generated starting at 30 μM compound with three-fold serial dilutions to generate a 10-dose plot. IC$_{50}$ values were then generated from the resulting plots, and the values expressed are the average of duplicate trials±standard deviation.

Compound 1 was identified to possess submicromolar HDAC inhibitory activity; however, it was not selective against representative members of the Zn$^{2+}$-dependant Classes 1 and 2 (HDAC1 and HDAC6, respectively). It was discovered that activity and selectivity could be improved for HDAC6 by accessing a unique cavity on the surface of HDAC6. This was accomplished substitutions on the urea nitrogens. There is a shorter substrate channel on HDAC6 relative to HDAC1 and this feature represented an excellent strategy to impart critical isoform selectivity (Butler et al., *J Am Chem Soc* 2010, 132(31):10842-10846; Kalin et al., *J Med Chem* 2012, 55(2):639-651). By incorporating substitutions on the urea motif, the additional branched molecular surface could form valuable contacts with the subtle differences at the HDAC6 surface while the benzyl linker would give a shorter linker that would favor away from HDAC1 inhibition. A summary of the HDAC1 and HDAC6 inhibitory data obtained is presented in Table 1A.

TABLE 1A

| | HDAC inhibition screen of substituted urea compounds[a] | | | |
|---|---|---|---|---|
| Compound | Structure | HDAC1 IC$_{50}$ (nM) | HDAC6 IC$_{50}$ (nM) | Fold Selective (HDAC1/ HDAC6) |
| 1 | | 265 ± 59 | 139 ± 27 | 2 |
| 5a | | 2550 ± 540 | 458 ± 64 | 6 |
| 5b | | 1910 ± 570 | 2.38 ± 0.38 | 803 |
| 5c | | 8950 ± 770 | 468 ± 130 | 19 |
| 5d | | 1690 ± 120 | 5.80 ± 0.50 | 292 |

TABLE 1A-continued

HDAC inhibition screen of substituted urea compounds[a]

| Compound | Structure | HDAC1 IC$_{50}$ (nM) | HDAC6 IC$_{50}$ (nM) | Fold Selective (HDAC1/HDAC6) |
|---|---|---|---|---|
| 5e | 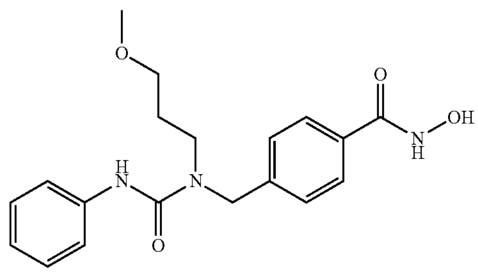 [SMILES: COCCCN(Cc1ccc(C(=O)NO)cc1)C(=O)Nc1ccccc1] | 5180 ± 130 | 11.7 ± 1.7 | 443 |
| 5f | 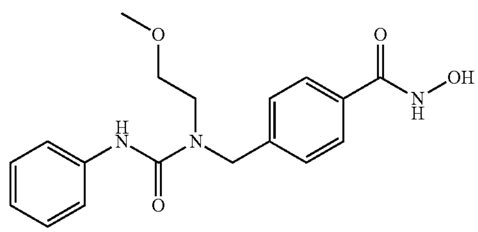 | 2250 ± 420 | 9.26 ± 0.66 | 243 |
| 5g | 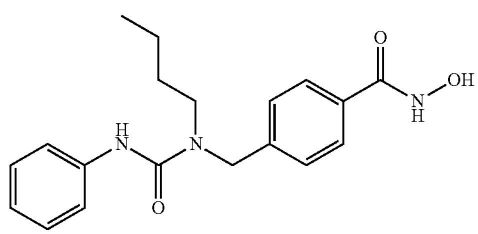 [SMILES: CCCCN(Cc1ccc(C(=O)NO)cc1)C(=O)Nc1ccccc1] | 3020 ± 740 | 5.02 ± 0.060 | 600 |
| 5h | 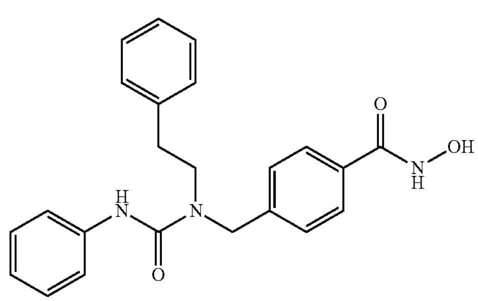 [SMILES: O=C(NO)c1ccc(CN(CCc2ccccc2)C(=O)Nc2ccccc2)cc1] | 3120 ± 640 | 14.0 ± 0.75 | 222 |
| 8a | 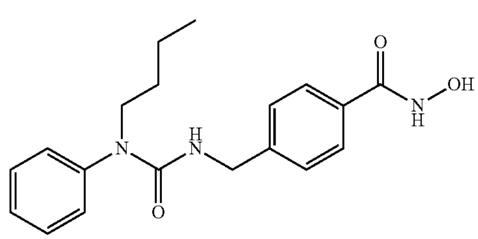 [SMILES: CCCCN(C(=O)NCc1ccc(C(=O)NO)cc1)c1ccccc1] | 8120 ± 600 | 25.2 ± 2.5 | 322 |

TABLE 1A-continued

HDAC inhibition screen of substituted urea compounds[a]

| Compound | Structure | HDAC1 IC$_{50}$ (nM) | HDAC6 IC$_{50}$ (nM) | Fold Selective (HDAC1/HDAC6) |
|---|---|---|---|---|
| 8b | 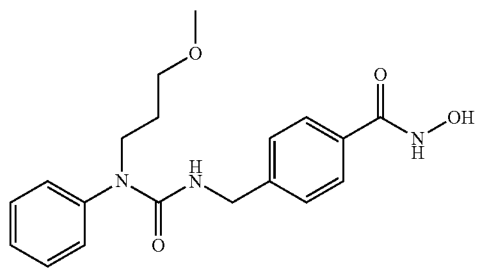 [SMILES: COCCCN(C(=O)NCc1ccc(C(=O)NO)cc1)c1ccccc1] | 1360 ± 450 | 60.3 ± 15.8 | 226 |
| 8c | 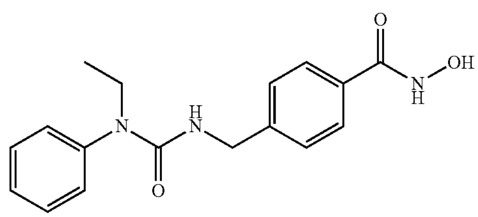 [SMILES: CCN(C(=O)NCc1ccc(C(=O)NO)cc1)c1ccccc1] | 1360 ± 650 | 41.1 ± 0.40 | 330 |
| 9a | 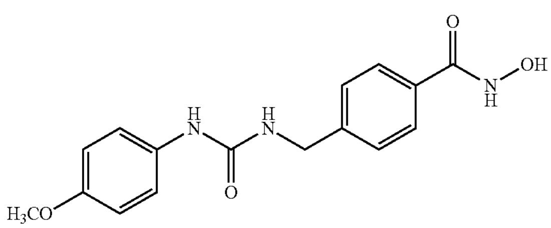 [SMILES: COc1ccc(NC(=O)NCc2ccc(C(=O)NO)cc2)cc1] | 1060 | 8.3 | 128 |
| 9b | 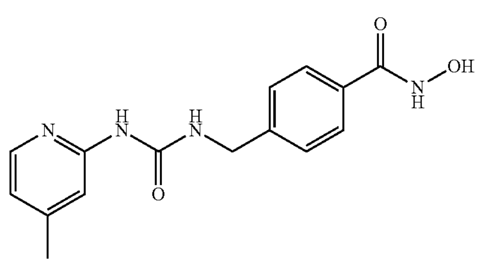 [SMILES: Cc1ccnc(NC(=O)NCc2ccc(C(=O)NO)cc2)c1] | 579 | 2.2 | 263 |
| 9c | 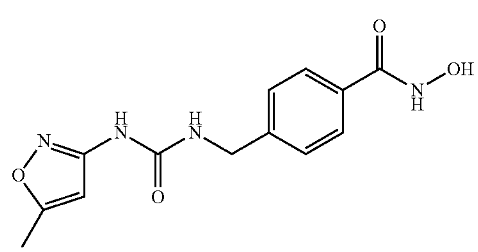 [SMILES: Cc1cc(NC(=O)NCc2ccc(C(=O)NO)cc2)no1] | 1000 | 6.9 | 145 |
| Tubastatin A[b] | 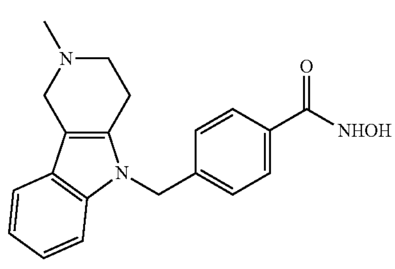 | 16400 ± 260 | 15.0 ± 0.01 | 1903 |

TABLE 1A-continued

HDAC inhibition screen of substituted urea compounds[a]

| Compound | Structure | HDAC1 IC$_{50}$ (nM) | HDAC6 IC$_{50}$ (nM) | Fold Selective (HDAC1/HDAC6) |
|---|---|---|---|---|
| TSA[b,c] | 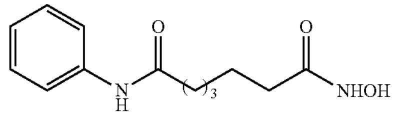 | 5 ± 1.0 | 1.2 ± 0.30 | 4 |
| MGCD0103 | 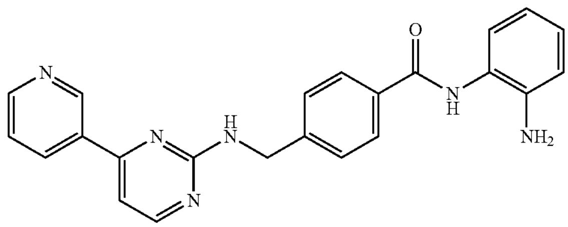 [SMILES: Nc1ccccc1NC(=O)c1ccc(CNc2nccc(-c3cccnc3)n2)cc1] | 102 ± 38 | >10,000[d] | — |

[a]IC$_{50}$ displayed are the mean of two experiments ± standard deviation obtained from curve fitting of 10-point enzyme assay starting from 30 μM analog with 3-fold serial dilution. Values are extracted from fitting dose-response curves to the data points,
[b]Butler et al., *J Am Chem Soc* 2010, 132(31):10842-10846;
[c]Trichostatin A;
[d]Fournel et al., "MGCD0103, a novel isotype-selective histone deacetylase inhibitor, has broad spectrum antitumor activity in vitro and in vivo," *Mol Cancer Ther* 2008, 7(4):759-768.

Data for additional compounds are shown in Table 1B.

TABLE 1B

HDAC inhibition screen of substituted urea compounds

| Compound | Structure | IC50 (μM) HDAC1 | HDAC6 | Selectivity (HDAC1/-6) | LogBBB | CLogP |
|---|---|---|---|---|---|---|
| JB6-22 | | 2.74 | 0.00976 | 281 | −0.997 | 1.06 |
| JB7-19 | | 0.721 | 0.00254 | 284 | −0.755 | 2.38 |
| JB7-20 | | 0.604 | 0.00612 | 99 | −0.572 | 2.37 |

The analogs based on 1 maintained the same 2-methoxyphenyl cap group but contained varied substitutions on the proximal linking nitrogen of the urea (5a-d). Introducing the branching element at this position had a dramatic impact on decreasing activity at HDAC1. Interestingly, inhibition at HDAC6 was found to be dependent upon the nature of this substitution. The dimethylamino substitution as in 5a, and the 3-indoyl substitution as in 5c, both proved detrimental to HDAC6 inhibition as they were over three times less potent compared to compound 1. They did however, maintain low micromolar inhibitory activity at HDAC1; but the activity against HDAC6 was only in the submicromolar range. As the tertiary amine in 5a would be protonated at physiological pH, it is possible that a positive charge is unfavorable for proper target binding. Likewise, the larger indole group of 5c may simply present too much steric bulk to be properly accommodated by the active site. However, the 3-hydroxypropyl derivative, 5b, and the 4-hydroxyphenylethyl derivative, 5d, resulted in a significant increase in the inhibition of HDAC6. These substitutions had only a marginal effect on HDAC1 activity. It is possible the hydroxyl groups of 5b and 5d are able to serve as H-bond acceptors or donors and possess favorable interactions with key amino acid residues on the HDAC6 surface, thus improving binding affinity.

The first series of compounds based on 1 maintained the 2-methoxy group in the aryl urea cap. The oxidative potential of phenols presents a substantial hurdle for in vivo efficacy thus the structure activity relationship (SAR) investigation was furthered by synthesizing a series with a phenyl cap using the same chemistry. To demonstrate the influence of an H-bond acceptor the free hydroxyl moeity was masked. Capping the free hydroxyl with a methyl group resulted in 5e, and was also found to be a low nanomolar inhibitor with >400 fold selectivity for HDAC6. Shortening to an ethylene bridge in 5f did not significantly dissuade HDAC6 inhibition, but did slightly increase activity against HDAC1 ultimately lowering the selectivity for HDAC6. The general trend established was that an H-bond donor and large aromatic groups deterred activity, whereas smaller groups with H-bond acceptors were favored for selective HDAC6 activity. Interestingly, the n-butyl 5g and phenethyl 5h were proficient HDAC6i in the low nanomolar range with 5g possessing excellent selectivity over HDAC1 (600 fold). These data refute the notion that a specific H-bond interaction is required for activity.

Shifting the branching element to the distal urea nitrogen resulted in analogs 8a-c. The most potent of this series, 8a, possessed the same n-butyl substitution as 5e. While 8a is a nanomolar HDAC6I, it is five-times less potent and more importantly, is less selective than the proximally substituted homolog 5e. The methoxy variant 8b suffered a dramatic decrease in potency towards HDAC6. Whereas the alkyl to heteroalkyl switch on the proximal nitrogen resulted in equipotent inhibition on the distal nitrogen, this modification was detrimental to furthering potent HDAC6I development. Decreasing the length of the alkyl branch in 8c also resulted in decreased HDAC6 inhibition. These data point to specific requirements for inhibitors decorated with a cap groups comprising of an acyclic urea and that potent and selective inhibition comes most from urea substitutions on the proximal nitrogen to generate a branched cap group.

Evaluating the disclosed compounds against other HDACi's developed by others reveals 5g, termed "Nexturastat A," is in fact a potent and selective HDAC6i. Comparing for example, 5g to Tubastatin A, another HDAC6i (Butler et al., *J Am Chem Soc* 2010, 132(31):10842-10846), reveals that the inhibition of HDAC6 has been improved while maintaining excellent selectivity relative to HDAC1. 5g also demonstrates comparable HDAC6 potency to Trichostatin A (TSA) (see Table 1). Additionally, the amino-benzamide ZBG has been incorporated into the HDACi's, and its introduction reduces Class 2 inhibition resulting in Class 1 selectivity; this is typified by MGCD0103, an HDACI that possesses antiproliferative activity and that has recently entered clinical trials (Zhou et al., "Discovery of N-(2-aminophenyl)4-4-pyridin-3-ylpyrimidin-2-ylamino)methyl benzamide (MGCD0103), an orally active histone deacetylase inhibitor," *J Med Chem* 2008, 51(14):4072-4075). Compared to MGCD0103, 5g leads to a 30-fold reduction in activity at HDAC1.

Similar experiments were done with compounds 10a, 10b, and 11a, which are cyclic ureas of Formula I-C(Table 2).

TABLE 2

HDAC screen of cyclic urea compounds

| Compound | HDAC1 IC$_{50}$ (nM) | HDAC6 IC$_{50}$ (nM) | Fold Selective (HDAC1/ HDAC6) |
|---|---|---|---|
| 10a | 28600 | 74.2 | 386 |
| 10b | 11800 | 22.2 | 531 |
| 11a | 7560 | 25.6 | 295 |

Since the HDAC isoforms are highly homologous obtaining selectivity is critical for avoiding off-target effects and is paramount for the development of the disclosed HDAC6i's. It is well known that Class 1 inhibition is responsible for the cytotoxicity associated with pan-selective HDACi; thus, 5g was screened against all 11 isoforms (Table 3). In the similar Class 1 and Class 4 isoforms, 5g displayed low micromolar activity compared to the low nanomolar activity of HDAC6. Moreover, 5g demonstrated high levels of selective inhibition against members of the related Class 2 HDAC isforms reaching >1000-fold selective in some cases. These data establish 5g, and similar analogs, to be potent and isoform selective HDAC6i's.

TABLE 3

Inhibitory profile of 5 g against HDAC1-11[a]

| Isoform | IC$_{50}$ (μM) | Fold selective for HDAC6 |
|---|---|---|
| HDAC1 | 3.02 ± 1.04 | 600 |
| HDAC2 | 6.92 ± 0.763 | 1380 |
| HDAC3 | 6.68 ± 1.75 | 1330 |
| HDAC4 | 9.39 ± 0.863 | 1870 |
| HDAC5 | 11.7 ± 0.141 | 2330 |
| HDAC6 | 0.00502 ± 0.00060 | — |
| HDAC6 | 4.46 ± 0.665 | 888 |
| HDAC8 | 0.954 ± 0.0799 | 190 |
| HDAC9 | 6.72 ± 1.15 | 1340 |
| HDAC10 | 7.57 ± 0.481 | 1510 |
| HDAC11 | 5.14 ± 0.686 | 1020 |

[a]IC$_{50}$ displayed are the mean of two experiments ± standard deviation obtained from curve fitting of 10-point enzyme assay starting from 30 μM analog with 3-fold serial dilution. Values are extracted from fitting dose-response curves to the data points.

Tubulin and Histone Acetylation Western Blot Assay

The ability of 5g to induce hyperacetylation of α-tubulin, a hallmark of HDAC6 inhibition, without elevating levels of acetylated histones was evaluated. B16 melanoma cells were plated at $10^5$ cells/well in 12 well plates and allowed to adhere overnight. A 50 mM stock of compound was then added by serial dilutions in complete medium to the indicated concentrations. Cells were incubated for 24 h under humidified conditions (37° C., 5% $CO_2$). Wells were then washed with cold PBS, and cells were lysed in a buffer containing 10 mM Tris-HCl pH 8.0, 10% SDS, 4 mM urea, 100 mM DTT, and 1× protease inhibitor (Roche). Cells were lysed for 30 min on ice and then sonicated for 8 min (8 cycles of 30 s on/30 s rest). Cells were then boiled for 10 min with 6× gel loading buffer and resolved on 4-15% gradient gels and subsequently transferred onto nitrocellulose membranes. Membranes were blocked with 5% milk in PBS-T and detection of specific antigens using antibodies against acetyl-H3 and H3 (Cell Signaling), and acetyl-α-tubulin and α-tubulin (Sigma). Bands were detected by scanning blots with LI-COR Odyssey imaging system using both 700 and 800 channels.

HDAC6 contains two catalytic domains. Its C-terminus domain is the functional domain for both synthetic and physiological substrates, whereas the N-terminal domain is devoid of enzymatic activity (Zou et al., "Characterization of the two catalytic domains in histone deacetylase 6," *Biochem Biophys Res Commun* 2006, 341(1):45-50). Low nanomolar treatment of 5g on B16 murine melanoma cells led to a dose-dependant increase of acetyl α-tubulin levels without a concamanent elevation of histone H3 acetylation (FIG. 39) indicating binding to the second, enzymatically-active catalytic domain. Not until concentrations of 1 and 10 μM were used was an observable increase in histone H3 acetylation found. This was expected as the biochemical $IC_{50}$ of 5g against the Class 1 HDACs, those responsible for histone acetylation, is in the micromolar range. There is a clear preference for activity of 5g in a cellular environment that corresponds to selective HDAC6 inhibition.

B16 Melanoma Cell Growth Inhibition Assay

Compounds were evaluated in an MTS assay to determine the ability of selective HDAC6i to exert an antiproliferative effect on B16 murine melanoma cells. B16 murine melanoma cells were plated at $5\times10^3$/well in 96 well flat bottom plates. The following day, media was changed to that containing various concentrations of HDACi or matched DMSO vehicle concentrations diluted in complete medium done in triplicate. Cells were incubated for 48 hours at 37° C. and 5% $CO_2$. Density of viable, metabolically active cells was quantified using a standard MTS assay (CellTiter 96™ $AQ_{ueous}$ One, Promega, Madison, Wis.) as per manufacturer's instructions. Briefly, 20 μL of reagent were added per well and incubated at 37° C. for 3 hours. Absorbances at 490 nM were measured spectrophotometrically with background subtraction at 690 nM. All values were then normalized and expressed as a percentage of medium control (100%).

Treatment with the compounds for 48 h resulted in dose-dependent growth inhibition of the oncogenic melanoma cells summarized in Table 4. The general trend for inhibiting cell growth correlates with potency for HDAC6. However, the potent and selective 5b, performed very poorly in the cellular assay possibly due to it being highly polar and lacking efficient cell permeability. Comparing the most active compounds 5d and 5f-h in this whole-cells assay reveals that the most selective HDAC6i's have the greatest efficacy in inhibiting cell growth. It should also be noted that they also have higher c Log P values, possibly contributing to improved cell permeability. As the c Log P is adjusted to more optimal levels, as exemplified for 5g (c Log P=2.20), cellular efficacy is restored, demonstrating that a proper balance of physiochemical parameters must be maintained.

TABLE 4

Antiproliferative activity against B16 murine melanoma cells

| Compound | $GI_{50}$ (μM) |
| --- | --- |
| 5a | 75.3 ± 1.23 |
| 5b | >100 |
| 5c | 30.4 ± 1.32 |
| 5d | 18.4 ± 1.23 |
| 5e | 22.2 ± 1.41 |
| 5f | 19.1 ± 1.19 |
| 5g | 14.3 ± 1.15 |
| 5h | 15.4 ± 1.20 |
| 8a | 65.8 ± 1.19 |
| 8b | >100 |
| 8c | >100 |
| Tubastatin | 40.5 ± 1.21 |
| LBH589 | 0.150 |

Figure 39:
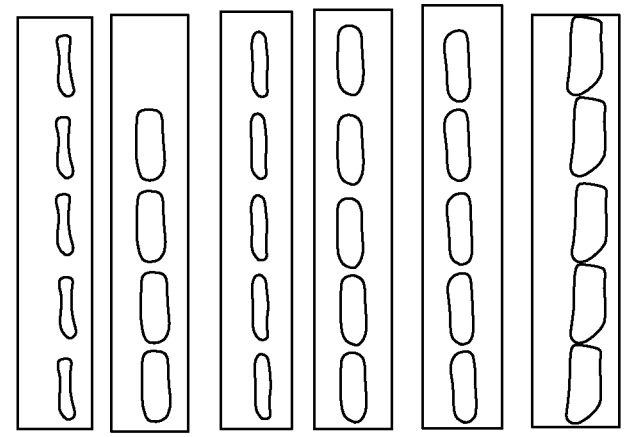
FIG. 39 is a Western blot showcasing substrate specificity of JB6-22, JB7-19, and JB6-20.
Figure 40:
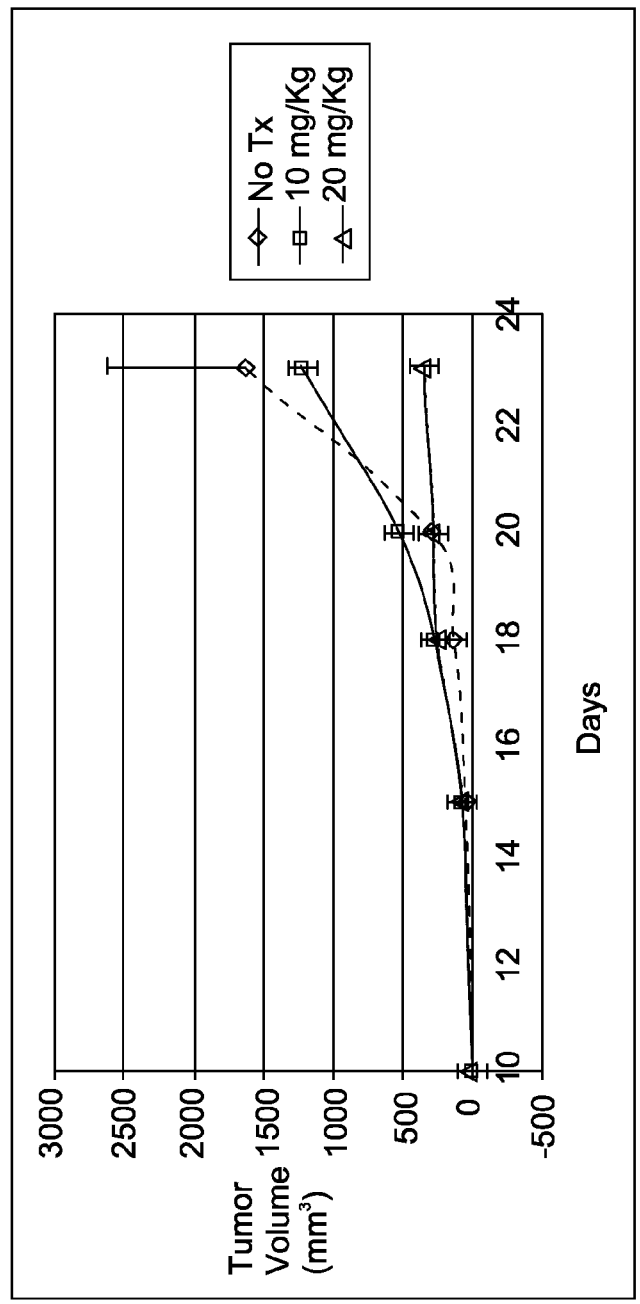
FIG. 40 is a graph showing the activity of various doses of JB7-19.

Compared to the pan-selective HDACi LBH589, 5g is approximately 100-fold less potent in inducing murine B16 melanoma cell death. This decreased efficacy is unlikely due to poor cell permeability, for as shown above, the treatment of B16 cells with nanomolar doses of 5g results in increased acetyl-tubulin levels (FIG. 39). Additionally, both compounds possess similar c Log P values (2.64 vs 2.20 for LBH589 and 5g, respectively). Rather, the effects of non-selective HDAC inhibition with LBH589 treatment are likely contributing to its increased potency, and in particular, its Class 1 activity. It is also of interest to note that 5g has increased potency against the B16 cell line in comparison to Tubastatin A (Table 4). While a definitive explanation for this difference in cellular activity is lacking, it is possible that this is due to the improved HDAC6 activity of 5g. While HDAC6-selective inhibitors have not played a role in cancer therapy to date, the data indicate that they have utility in this area. This work thus constitutes the first report of HDAC6 selective inhibitors that possess antiproliferative effects against melanoma cells.

Pharmacologic Disruption of HDAC6 in Melanoma Causes G1 Arrest and Inhibits Cell Proliferation Cell proliferation was evaluated using various pan- and isotype selective HDACi in a broad panel of human melanoma cell lines. Briefly, cells were plated at $10\times10^3$/well in a 96 well flat bottom plate. The following day, media was changed to that containing different concentrations of HDACi or matched DMSO vehicle concentrations diluted in complete medium done in triplicate, all with a final concentration of less than 0.1% DMSO. Cells were incubated for 24 hours at 37° C. and 5% CO2. Density of viable, metabolically active cells was quantified using a standard MTS assay purchased from Promega (Fitchburg, Wis. USA) as per manufacturer's instructions. All values were then normalized and expressed as a percentage of medium control growth.

LBH589 and TSA are pan-HDACi, MGCD0103 targets Class I (HDACs 1, 2, 3, and 8) and IV (HDAC11), while Tubastatin A and Nexturastat A are HDAC6 selective inhibitors. All HDACi tested were able to inhibit proliferation in both NRAS and BRAF mutant human melanoma cell lines tested, albeit with differing potencies (FIG. 41A-41E). LBH589 was the most potent, with an $IC_{50}$ range from 10-50 nM. TSA significantly inhibited cell lines in the low 100 nM range, while the remaining compounds tested, MGCD010, Tubastatin A, and Nexturastat A, were effective in the low micromolar range. Of note, no overt toxicity against normal melanocytic cell lines was observed; however, limited conclusions can be drawn regarding effects on proliferation given the low proliferative index of these cells. Nonetheless, pharmacologic inhibition of HDAC6 recapitulated the anti-proliferative effects of pan-HDACi.

Figure 41:
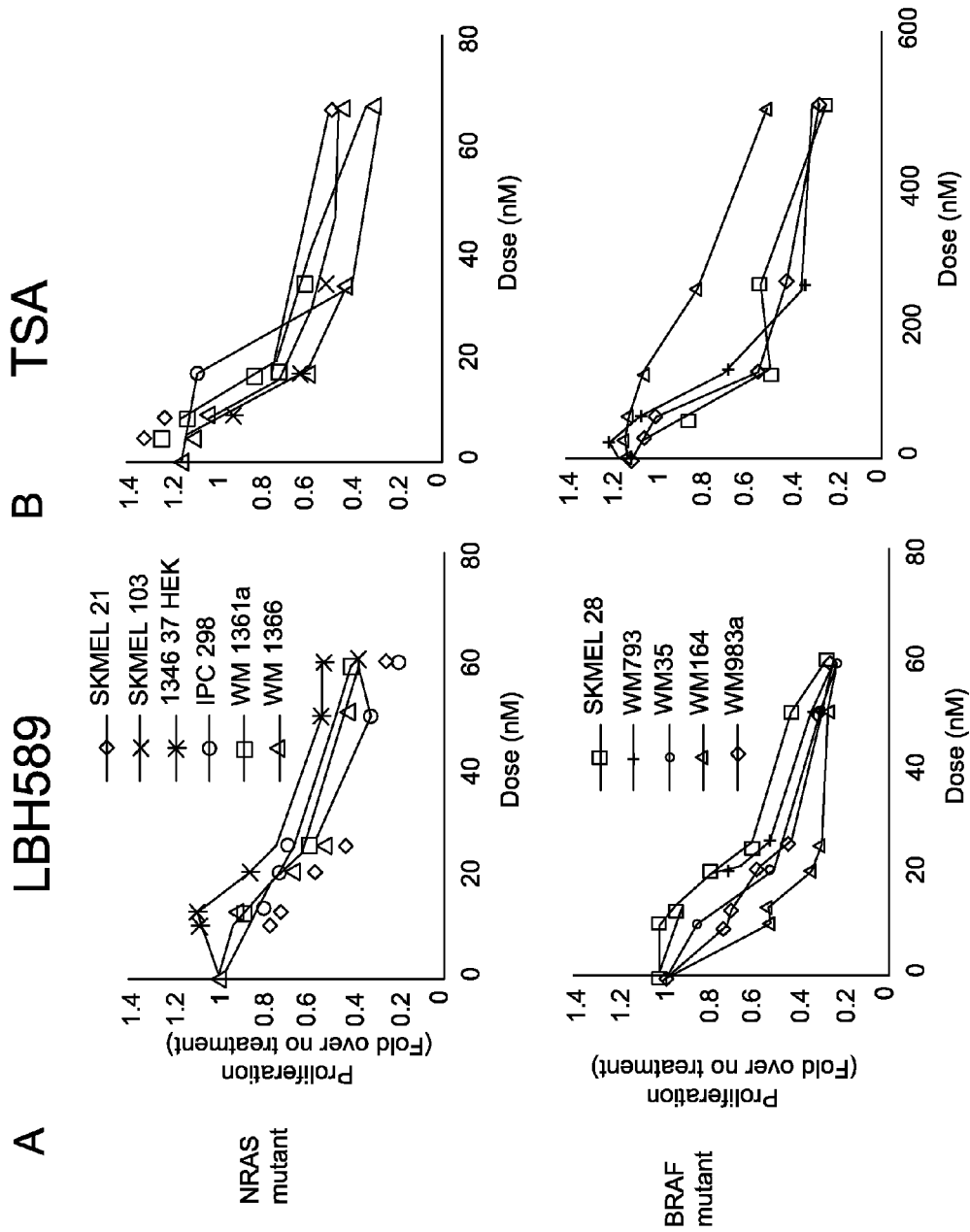
FIG. 41 shows NRAS and BRAF mutant melanoma cells were incubated with (A)LBH589, (B)TSA, (C)MGCD0103, (D)Tubastatin A and (E) Nexturastat A at different concentrations for 24 hrs. Error bars represent standard deviation from triplicates. This figure is representative of three independent experiments. (F,G,H) Cell cycle analysis of melanoma WM164, WM983A and WM793 human melanoma cell lines stained with propidium iodide. Data is representative of three experiments with similar results. (I,J,K) Two BRAF-mutated melanoma cell lines WM164 and WM983A were treated with LBH, TSA, MGCD0103 and 2 specific HDAC6 inhibitors TubastatinA and NexturastatA, at two different concentrations to determined the specificity, then were immunoblotted using specific antibodies for tubulin, acetyl-tubulin and acetyl-histone3.
Figure 41:
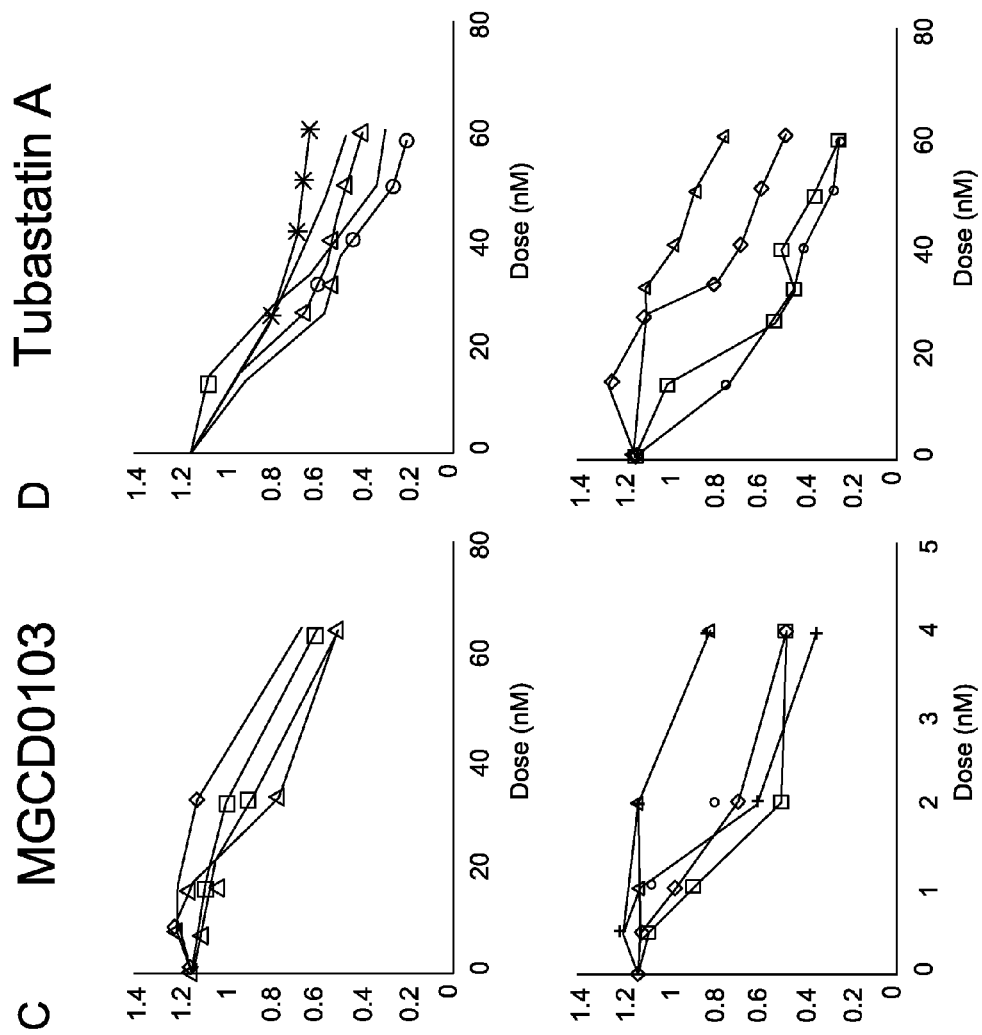
Figure 41:
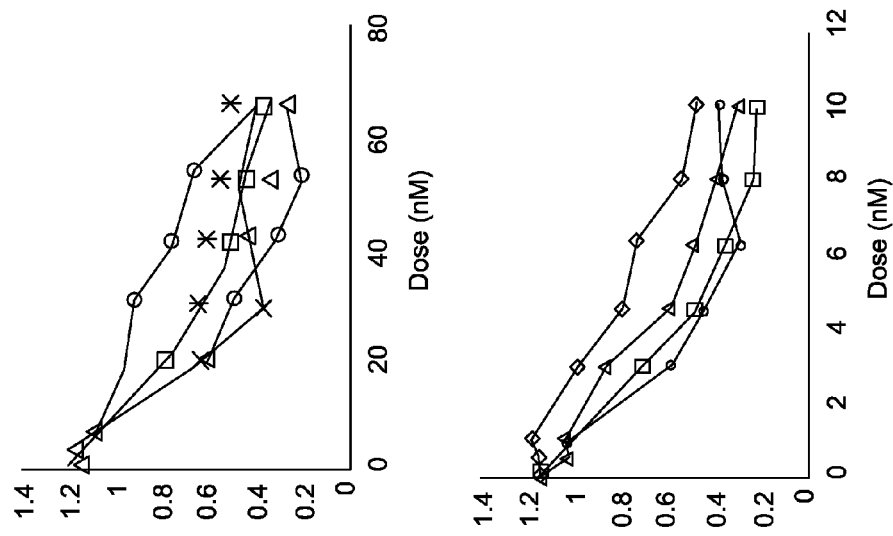
Figure 41:
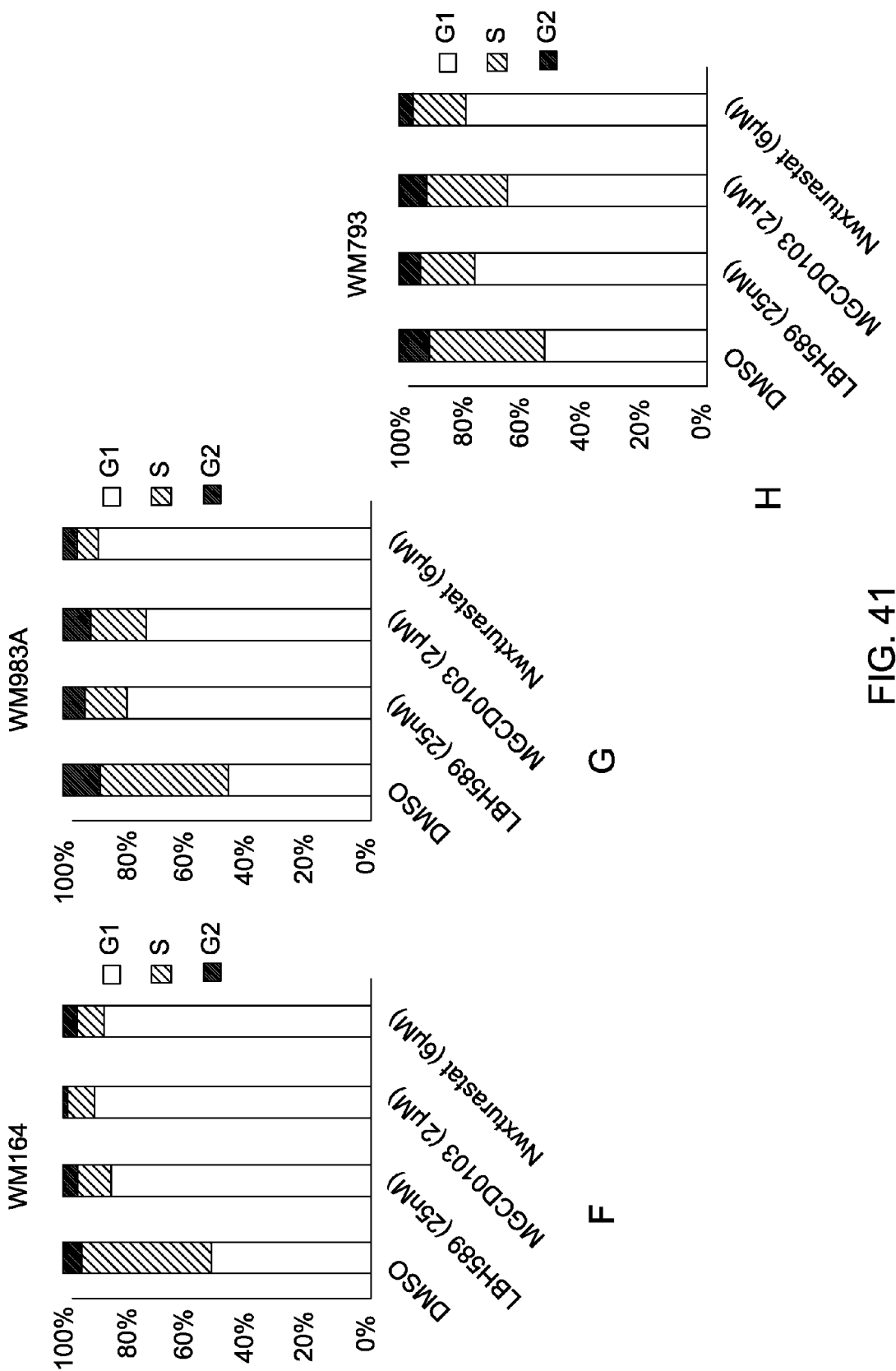
Figure 41:
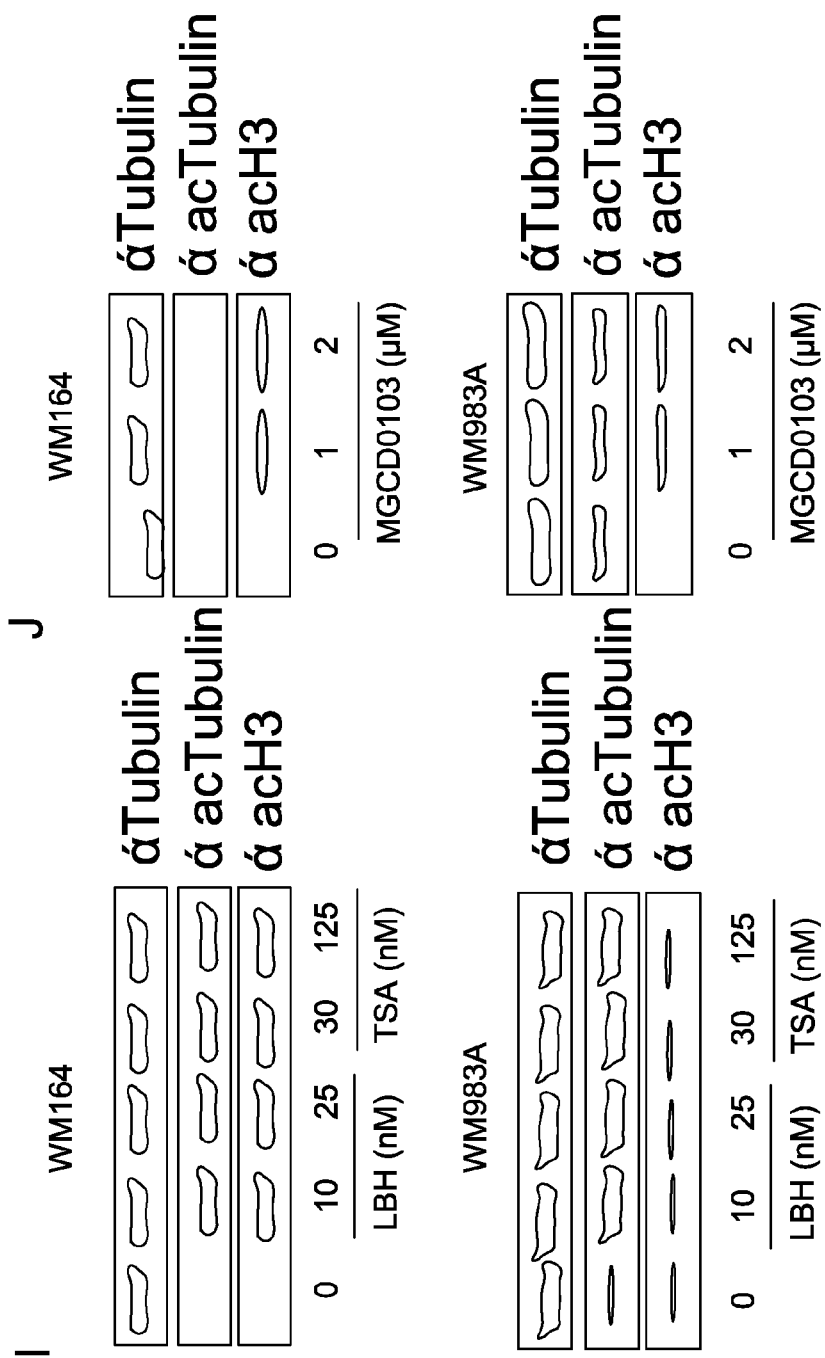
Figure 41:
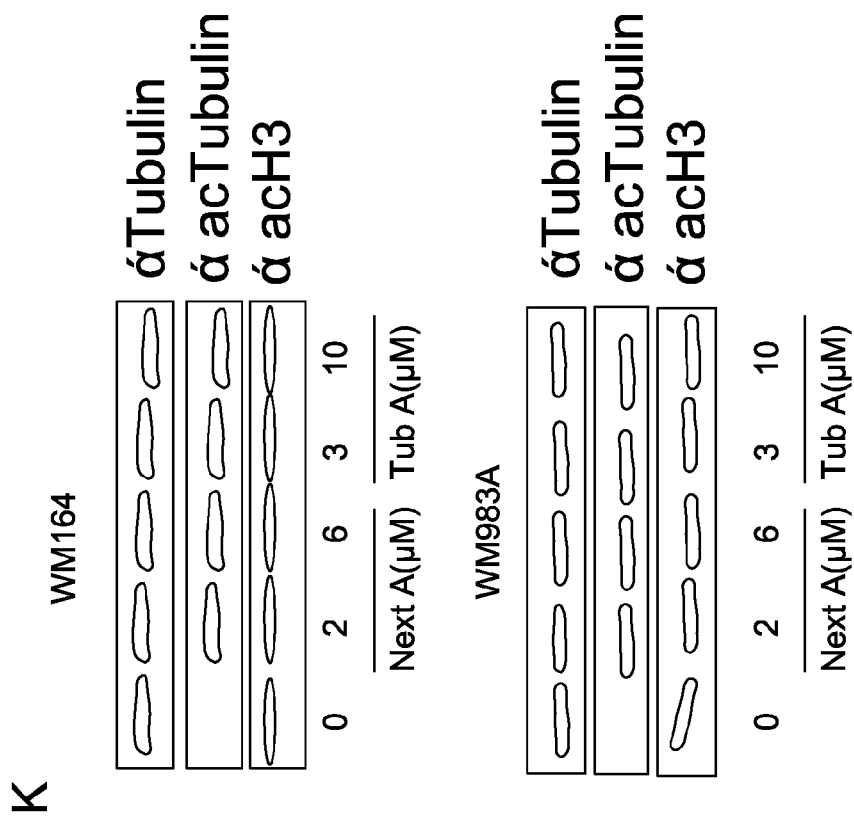
Figure 42:
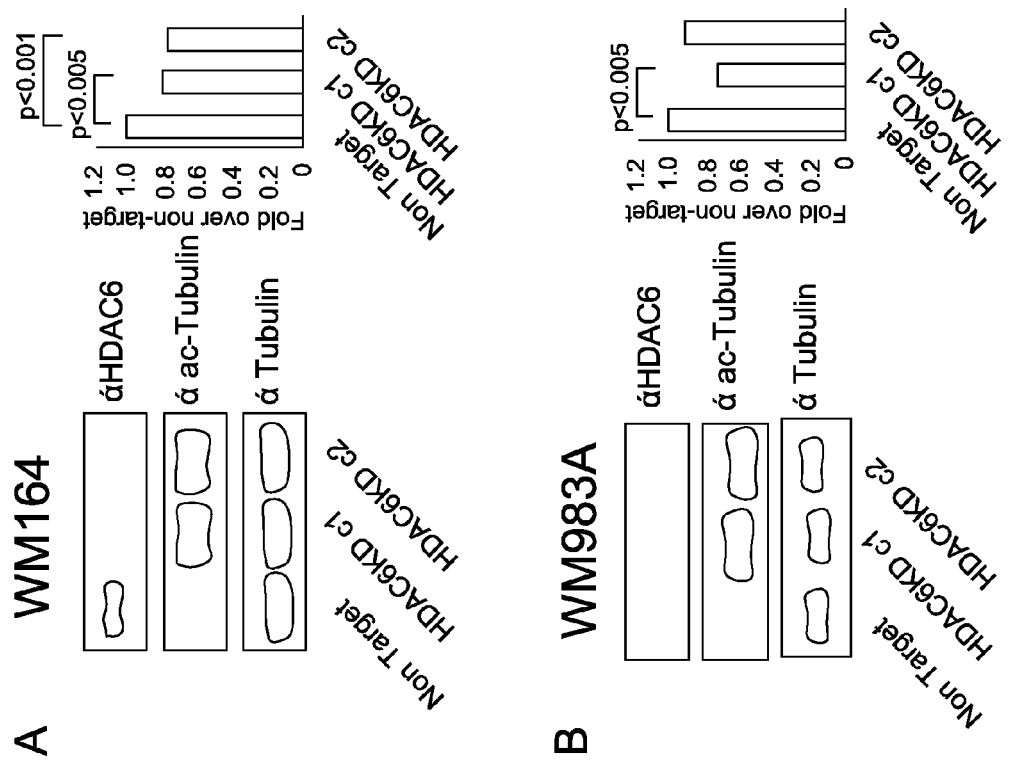
FIG. 42 shows characterization of HDAC6KD melanoma cell lines: (A, B, C, D, E, F), human melanoma cell lines, (G) B16 murine melanoma cell line. Cell lines were transduced with shRNA either coding for HDAC6 or a non-target sequence. Cells were immunoblotted using specific antibodies against HDAC6, tubulin and acetylated tubulin. In the right side two HDAC6KD clones and NT controls were analyzed and then subjected to MTS assay (Promega). Data is representative of three experiments with similar results. (I) Cell cycle analysis of NT and HDAC6KD human melanoma cell lines WM164 and WM983A and 1 murine melanoma cell line B16 were stained with propidium iodide. Data is representative of three experiments with similar results. (H) Full length and cleaved protein fragments of PARP, BAX, cleaved caspase 8 and cleaved caspase 3 were detected by immunoblot in HDAC6KD and NT melanoma cells.
Figure 42:
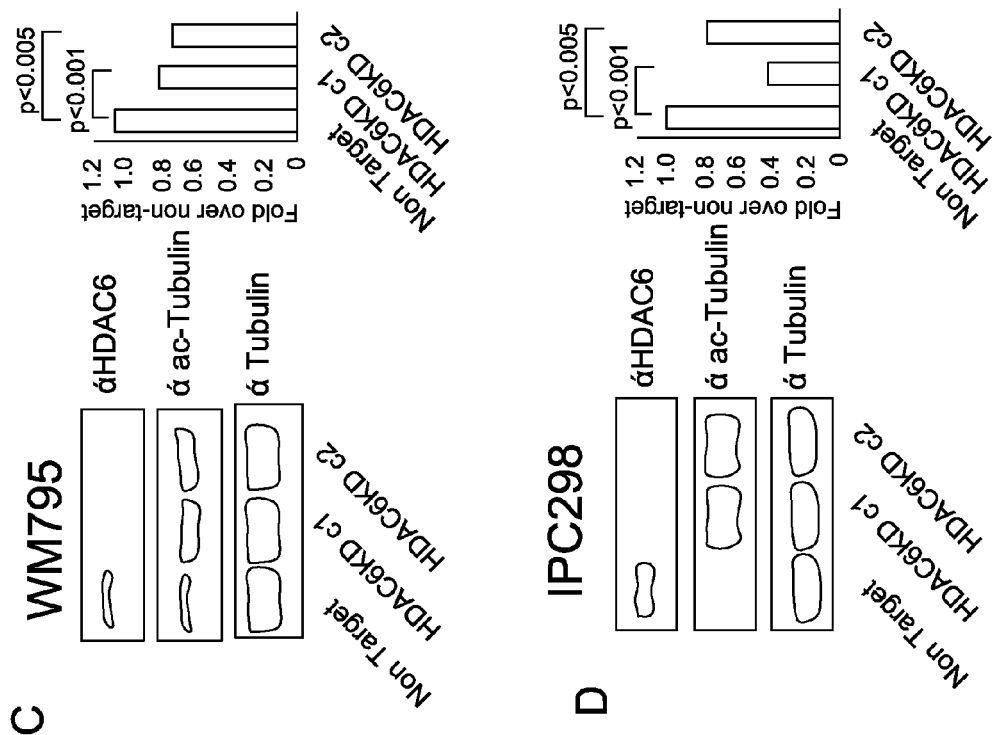
Figure 42:
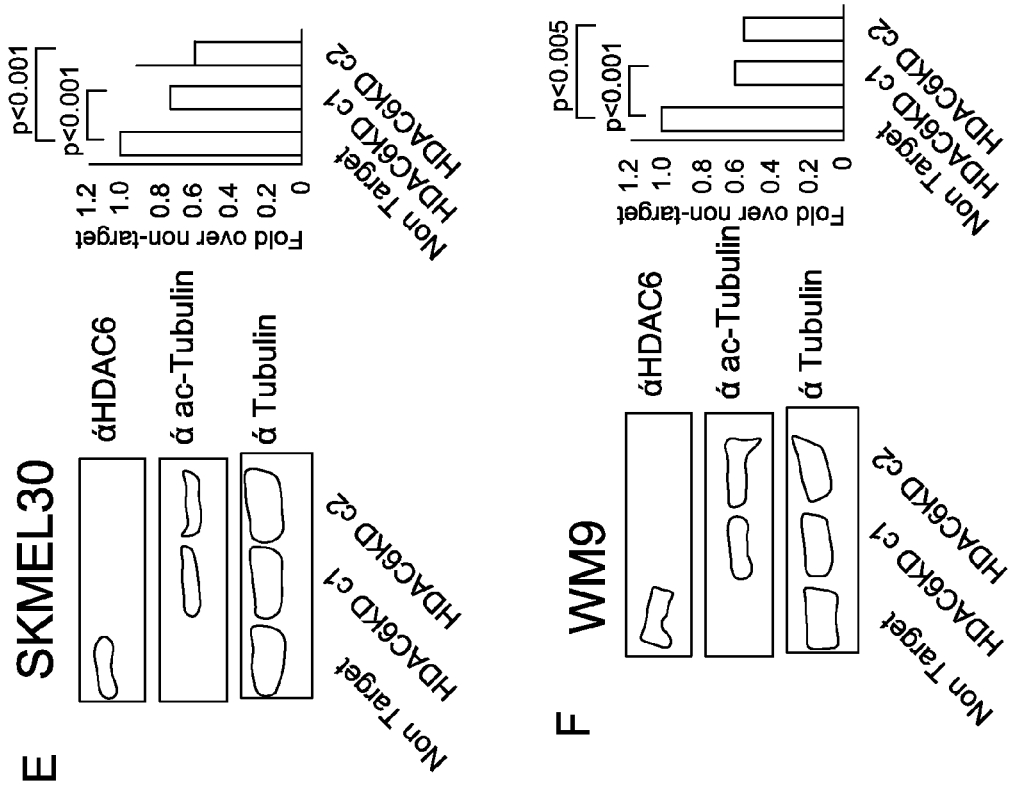
Figure 42:
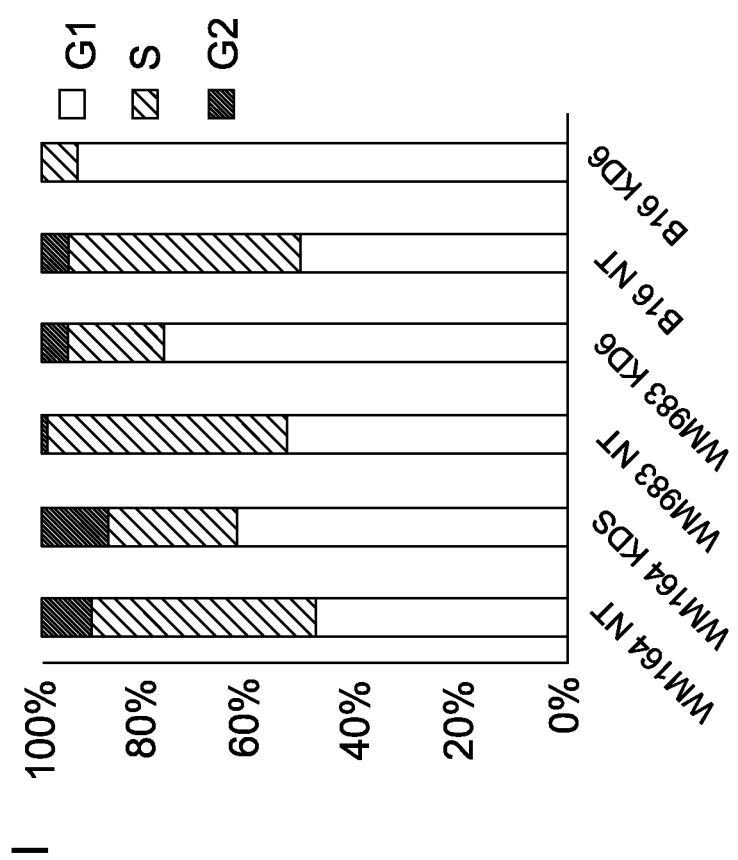

To confirm the selectivity of isotype specific HDACi, Western blot analysis was performed on the acetylation status of known HDAC substrates including histone H3 and H4, which are known Class I HDAC targets, and α-tubulin, a target for HDAC6. The doses required to impart the anti-proliferative effect coincided with that needed to increase acetylation of the respective HDAC substrates (FIG. 41F-41H). Furthermore, the acetylation of α-tubulin is unchanged by MGCD0103 confirming its selectivity in sparing HDAC6 (FIG. 41H). Conversely, HDAC6 selective inhibitors (HDAC6i) increase α-tubulin acetylation but not histone acetylation (FIG. 41F).

Cells were treated with indicated doses of HDAC inhibitors or DMSO control and then trypsinized, washed, and rendered into a single cell suspension in 1 mL of DPBS. 4 mL ice cold 200 proof ethyl alcohol was added dropwise while vortexing to fix cells. Samples were washed and resuspended in 75% ethanol solution overnight. Then, cells were washed in PBS+0.1% Triton X-100 and counted. Equal numbers of cells were then stained in a solution containing 10 µg/mL RNAseA+1 µg/mL propidium iodide for 2 hours at room temperature. Data was then acquired using a FACSCaliber with at least 10,000 events collected. Cell cycle analysis was completed using ModFit LT (Verity Software House, Topsham, Me.).

Treatment with pan-HDACi led to an arrest in G1. HDAC6 inhibition also led to a similar profile. In contrast, MGCD0103, which spares HDAC6, resulted in variable cell cycle effects including changes in the G2 cell fraction in addition to a G1 arrest, which was less potent in 2 out of 3 cell lines depicted.

Figure 46:
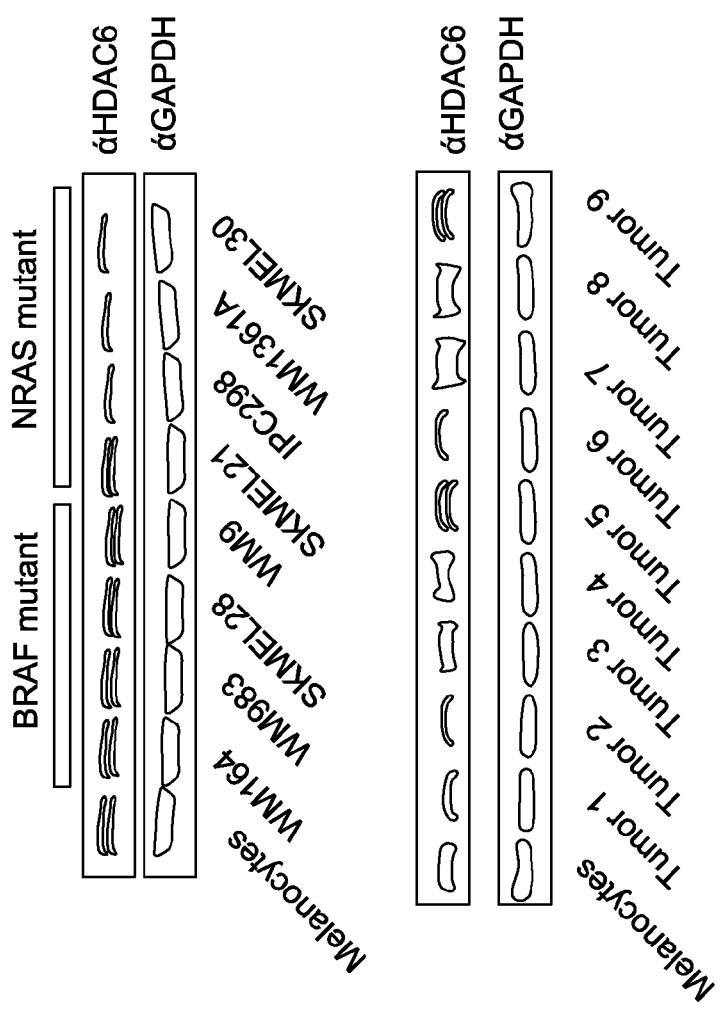
FIG. 46 shows HDAC6 profile of melanoma cell lines: Top: Human melanocytes, BRAF mutant and NRAS mutant melanoma cell lines were immunoblotted using specific antibodies for HDAC6 and GAPDH. Bottom: HDAC6 expression from 9 primary human tumor melanomas compared with normal human melanocytes.
Figure 47:
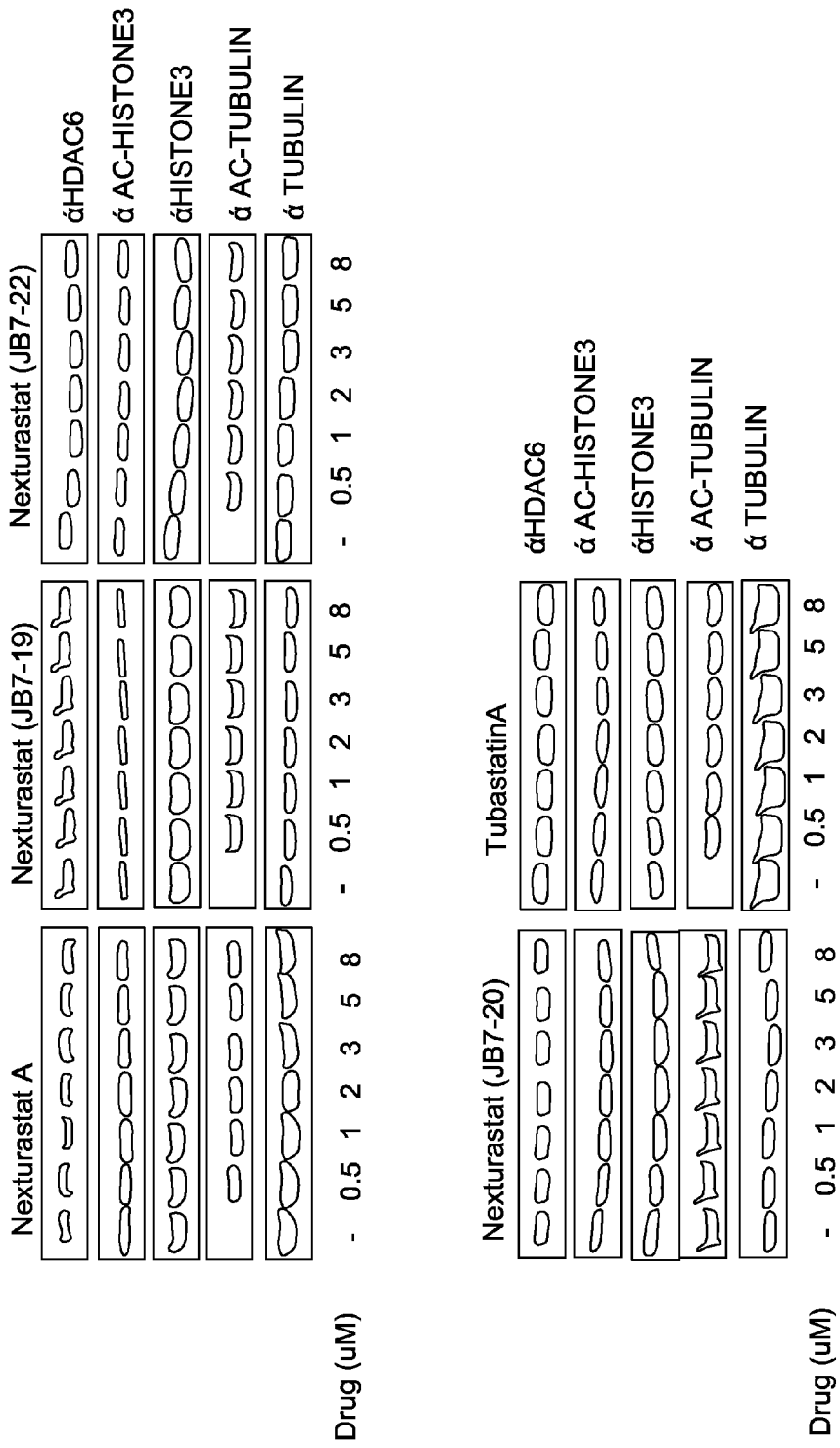
FIG. 47 shows HDAC6 inhibitors increase acetyl-tubulin without modifying the acetylation status of Histone 3. WM795 Human Melanoma cell line was incubated with Nexturastat A, JB7-19, JB7-22, JB720 and Tubastatin A at different concentrations for 24 hrs and then immunoblotted using specific antibodies for HDAC6, acetyl-histone3, histone 3, acetyl-tubulin and tubulin.
Figure 48:
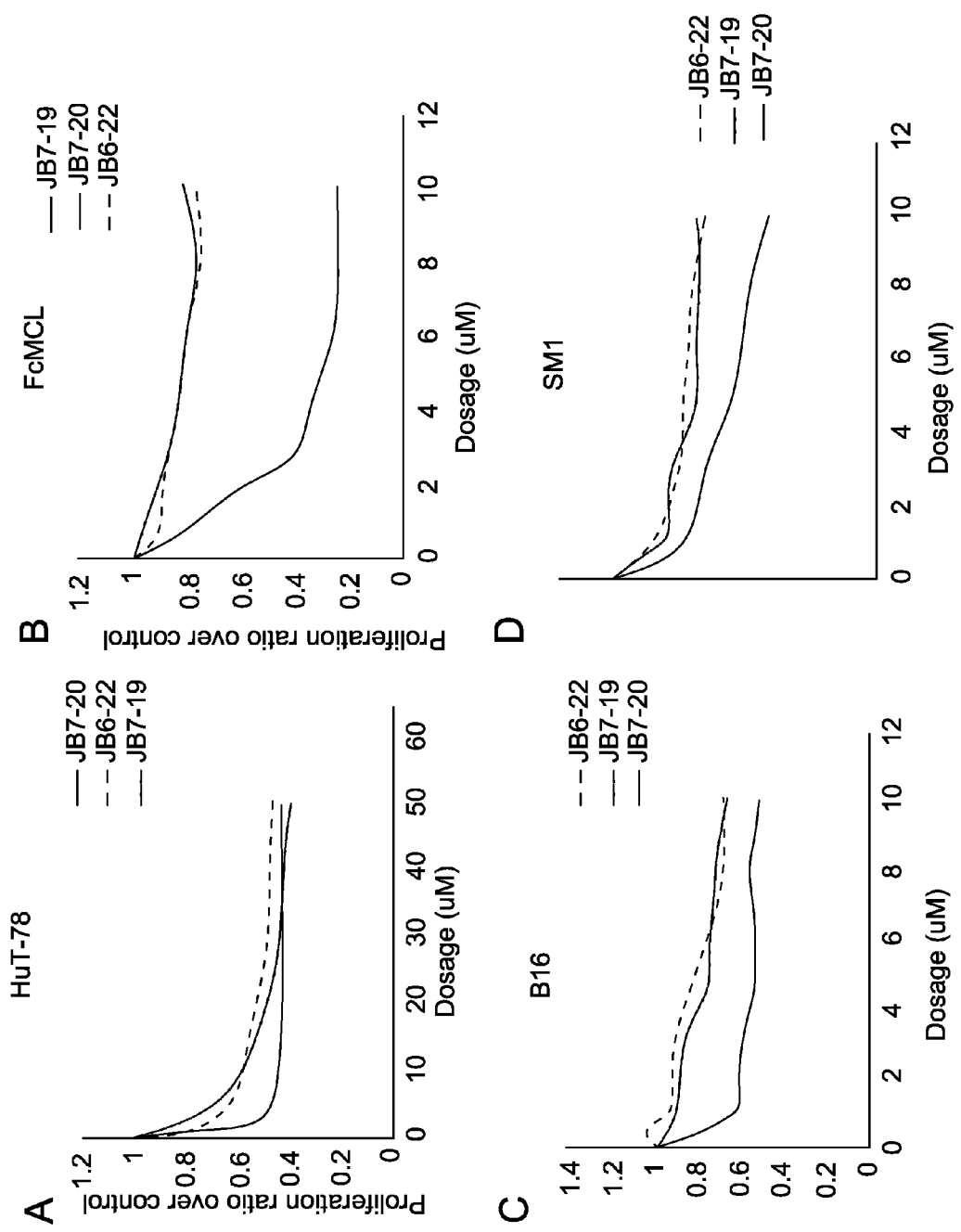
FIG. 48 shows HDAC6 inhibitors decrease cell proliferation of cancer cells. Human cutaneous T-cell lymphoma (CTCL) HuT-78 (A), murine mantle cell lymphoma (MCL) (B), and murine melanoma B16 (C) and SM1 (D) cells were incubated with JB7-19, JB7-22, JB720 at different concentrations for 24 hrs. Cell viability was measured using Cell-Titer 96 Aqueous ONE solution (Promega, Madison, Wis.) and compared to DMSO treated control samples. Error bars represent standard deviation from triplicates.
Figure 49:
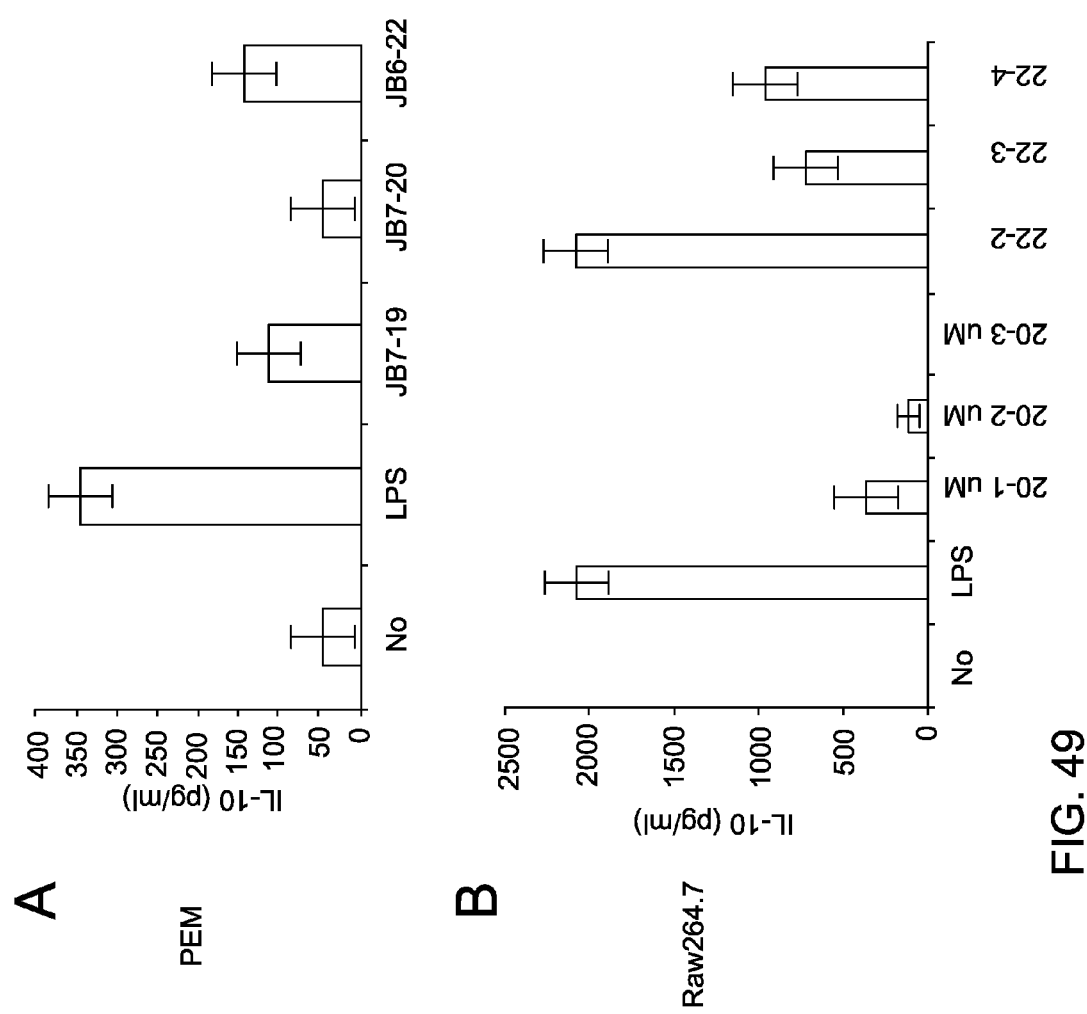
FIG. 49 shows HDAC6 inhibitors inhibit IL-10 production in antigen presenting cells. Murine peritoneal elicited primary macrophages (PEM)(A) and murine RAW264.7 (B) cells were incubated with JB7-19, JB7-22, JB720 at the concentration indicated on each chart. After 24 hrs, the production of IL-10 was measured by ELISA.

In order to determine if the effect of HDAC6 inhibition correlated with the expression levels of HDAC6, its expression in melanoma cells lines, as well as a group of metastatic melanoma samples obtained from de-identified patients, was evaluated (FIG. 46). The expression of HDAC6 was variable among BRAF mutant and NRAS mutant cell lines when compared to normal melanocytes. Likewise, its expression was also variable in primary patient samples.

Genetic Abrogation of HDAC6 Results in Decreased Proliferation and G1 Arrest shRNA lentiviral transduction particles for murine HDAC6 (NM010413, TRCN0000008415), for human HDAC6 (NM00604, TRC0000004839) and non-target shRNA (SHC002V) were obtained from Sigma Aldrich. Transductions were performed according to manufacturer's instructions. Melanoma cells were grown in antibiotic-free medium and individual wells transduced with one of the shRNA particles in 4 µg/mL hexadimethrine bromide. After 72 hours, medium was changed and cells permitted to proliferate. After an additional 24 hours, medium was replenished with that containing puromycin (the amount of the puromyucin is depending of the cell line). Upon reaching confluency, cells were passaged. Excess cells were lysed and immunoblotted with anti-HDAC6. To generate monoclonal populations, serial dilutions of the polyclonal population with the most significant knock down was then plated in a 96 well flat bottom tissue culture dish to obtain wells containing single, or very few cells. Wells were inspected daily for appearance of isolated colonies. When there are appreciable cells, wells were trypsinized and single colonies carefully aspirated and transferred to new plates to expand. Multiple colonies were selected and tested to ensure the reproducibility of effects from knocking down HDAC6 and not an effect of individual clones.

The lentiviral particles encoding specific shRNA against HDAC6 were used to generate at least two different stable HDAC6 knock down (HDAC6KD) monoclonal populations in a panel of human melanoma cell lines, including both NRAS and BRAF mutant cell lines (FIG. 42A-42F). In parallel, and using the same experimental approach, HDAC6 was knocked-down in the murine melanoma cell line B16 (FIG. 24G). As a control for each of these monoclonal cell lines, lentiviral particles containing a non-targeting shRNA was used, which does not target any mRNA sequence in both human and mouse. Confirming functional knockdown of HDAC6, western blot analysis demonstrated increased acetylation of α-tubulin (FIG. 42A-42G, second lane of each panel). Upon targeted knock down of HDAC6, a decrease in proliferation was observed and was confirmed by MTS assay (FIG. 42A-42G, right side of each panel). Furthermore, HDAC6KD cells displayed an arrest in G1 by FACS (FIG. 42I). Consistent with HDAC6i treatment, HDAC6KD did not seem to impact apoptotic pathways with minimal changes in PARP or caspase cleavage (FIG. 42H).

Inhibitions of HDAC6 Augments Expression of Immunologically Relevant Molecules

For surface marker analysis melanoma cells were treated with TubastatinA or DMSO for 48 hrs, and/or using Non target and HDAC6KD cell lines, Cells were singly stained with phycoerythryn (PE) conjugated antibodies against MHC I, MHC II, CD40, CD80, CD86. Conjugated antibodies were purchases from eBioscience (San Diego, Calif., USA). After staining for 30 minutes at 4° C., cells were washed three times and then resuspended in buffer containing DAPI (50 ng/mL) for viability. At least 10,000 events were collected using an LSR II (BD) and subsequently analyzed using FlowJo software.2.2.7.

Figure 43:
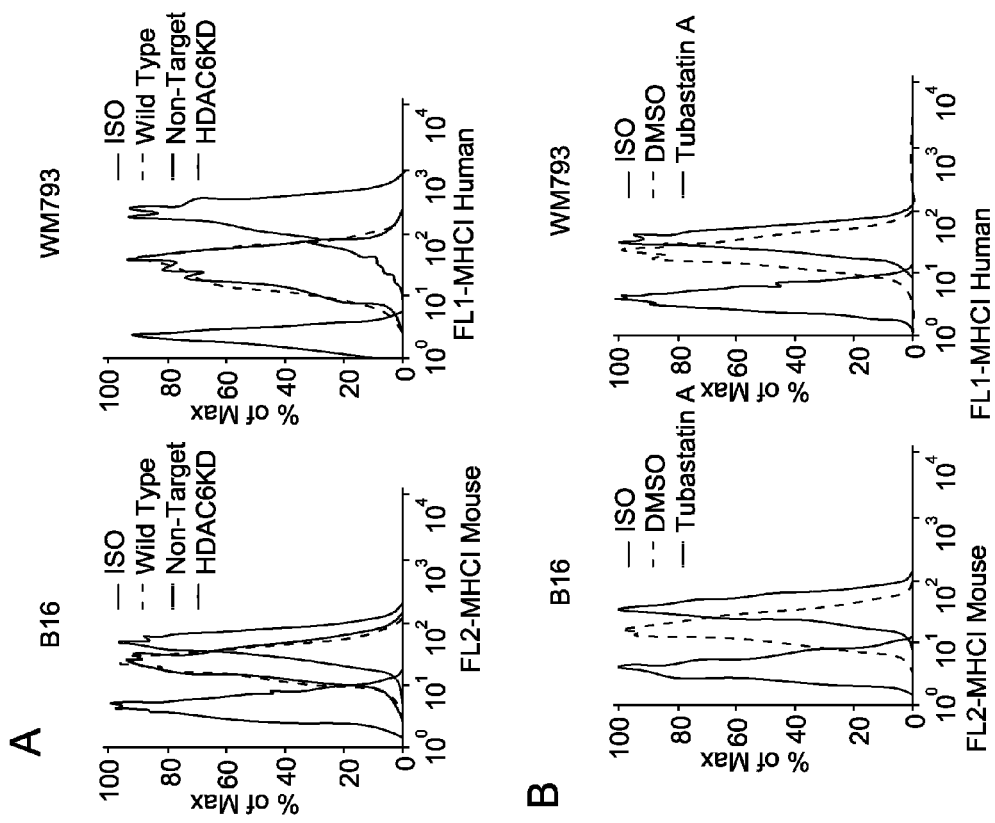
FIG. 43 shows increase of MHC1 and increase expression of tumor antigens in HDAC6 inhibition in melanoma cell lines: (A) NT and HDAC6KD human and murine melanoma cell lines were analyzed for the expression of MHC I. (B) Wild type murine (B16) and human (WM793) melanoma cell lines were treated in vitro with TubastatinA (3 µM) for 48 hours and then were analyzed for the expression of MHC I. (C) Different human melanoma cells were incubated with NexturastatA and TubastinA for 48 hours and the expression of tumor antigens was measured by qRT-PCR. (D) Expression of tumor antigens was measured in human WM164 non-target and HDAC6KD cells. (E) Expression of tumor antigens mart-1 and gp-100 was measured by western blot.
Figure 43:
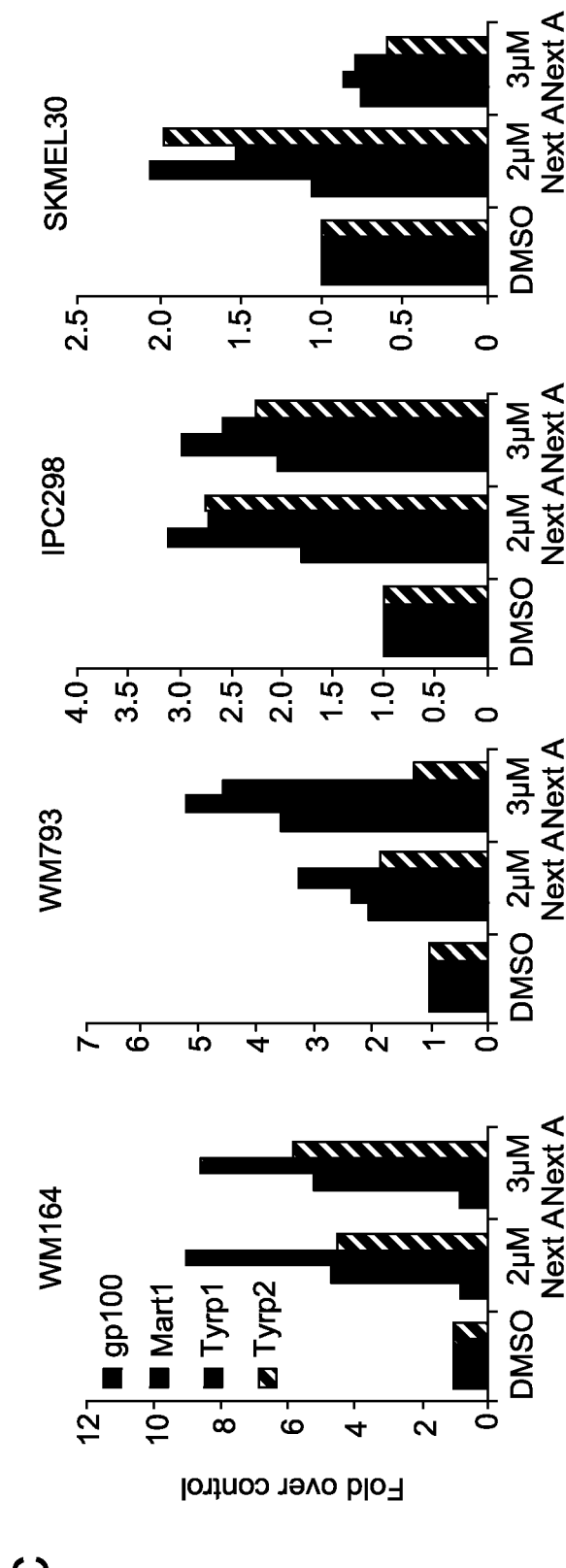
Figure 43:
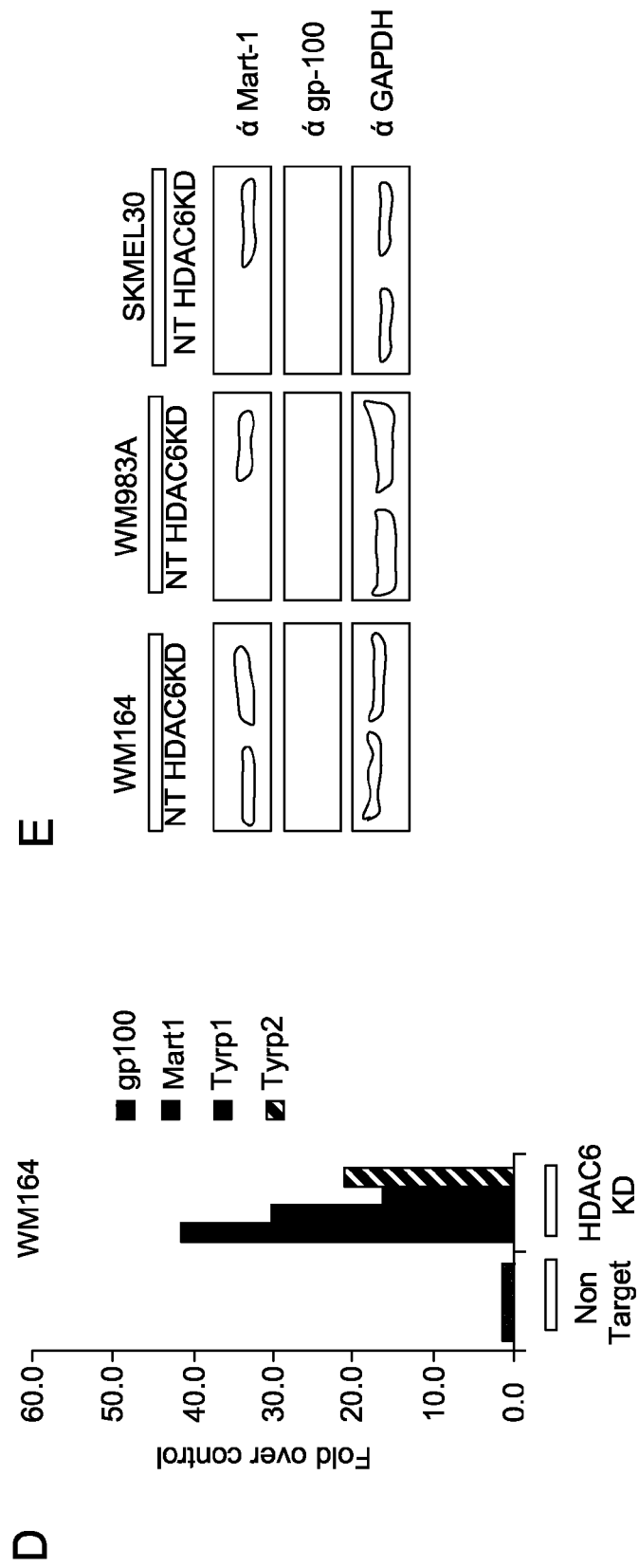

In addition to direct cytotoxicity, pan-HDACi have immunologic effects on melanoma including modulation of MHC, co-stimulatory molecules, and cytokine production. In both human and murine melanoma cell lines, genetic (FIG. 43A) and pharmacologic (FIG. 43B) disruption of HDAC6 led to increased surface expression of MHC I by flow cytometry. Additionally, an upregulation of melanoma antigens gp100, MART1, TYRP1 and TYRP2 at the mRNA level in human melanoma cell lines following treatment with Nexturastat A or Tubastatin A (FIG. 43C) as well as targeted knockdown (FIG. 43D). As confirmation, protein expression of gp100 and MART1 were also increased following genetic disruption of HDAC6 (FIG. 43E).

The expression of other immune receptors including MHCII, CD80, CD86 and CD40, were also measure but no change in their expression was observed following either pharmacologic or genetic disruption of HDAC6.

Figure 44:
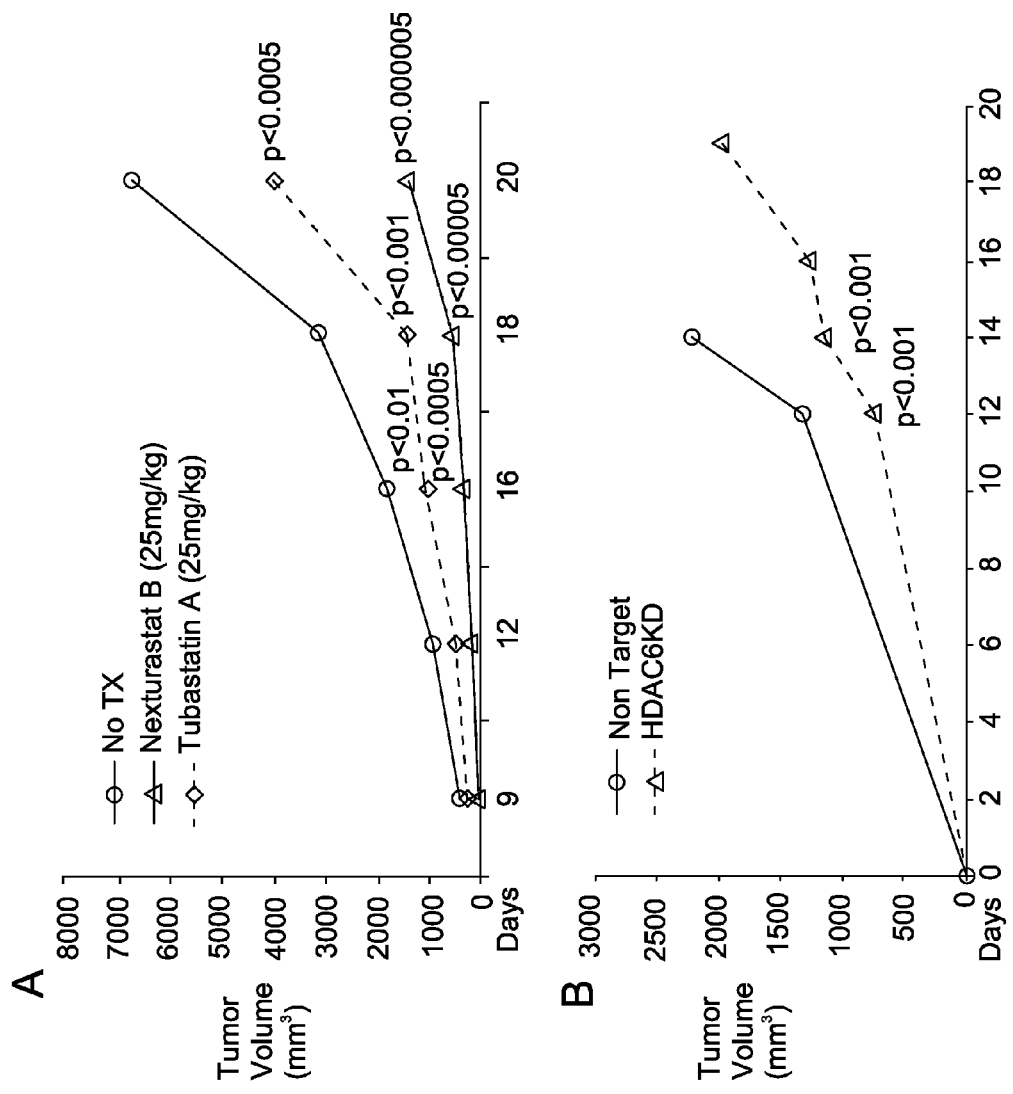
FIG. 44 show HDAC6 modulates tumor growth in vivo. (A) In vivo tumor growth of C57BL/6 mice injected subcutaneously with B16-F10-luc WT cells. Mice were either untreated or treated with the HDAC6 inhibitor Nexturastat B or Tubastatin A via daily intraperitoneal injection. (B) In vivo growth of C57BL6/mice injected with B16 HDAC6KD or NT melanoma cells.
Figure 45:
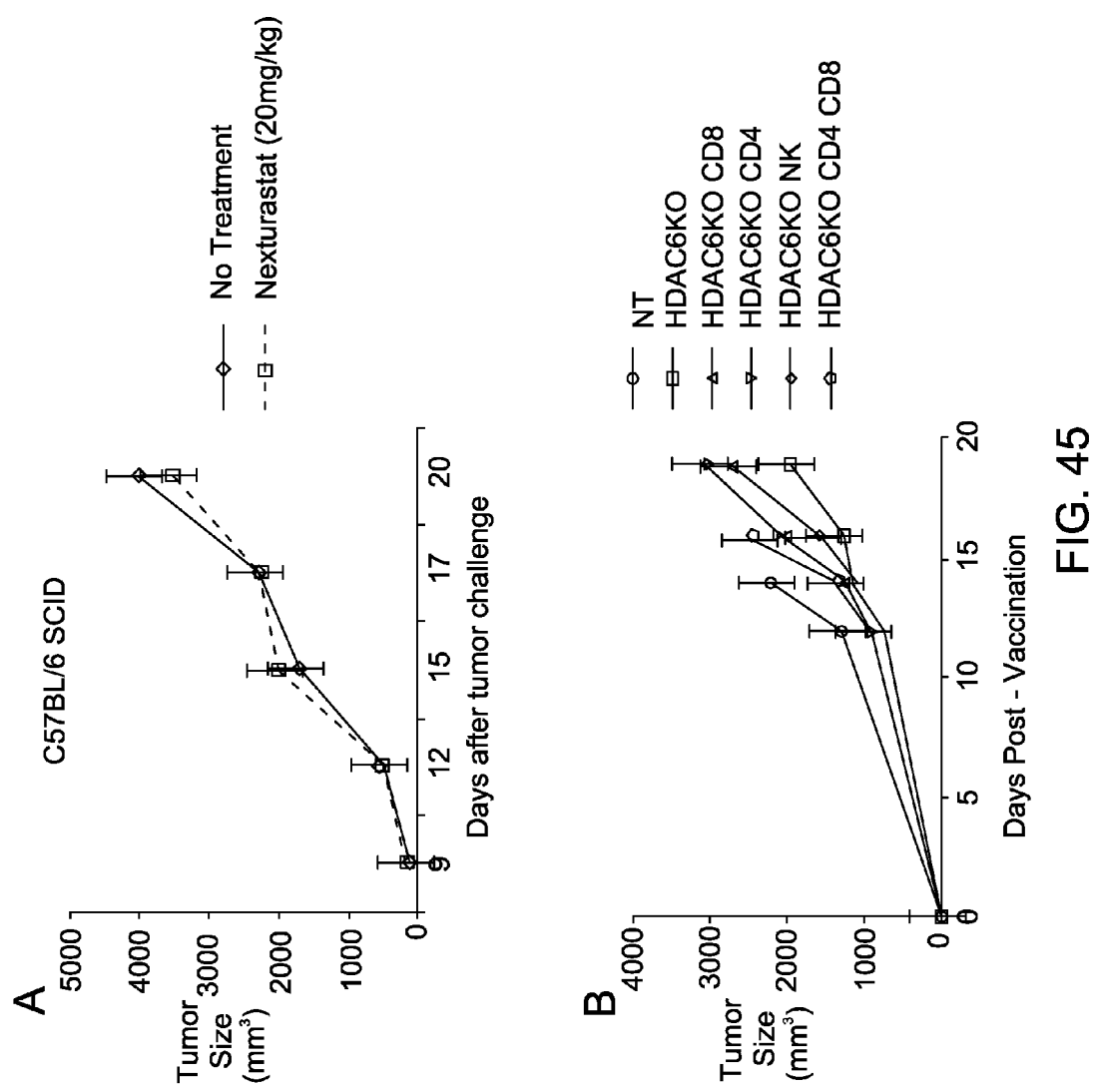
FIG. 45. Differences in growth of melanoma cells after HDAC6 inhibition in altered immune systems: (A) In vivo growth of B16 WT melanoma injected into SCID mice was not significantly different despite treatment with HDAC6 inhibitor Nexturastat B compared with control treatment. (B) In vivo growth of B16 HDAC6KD melanoma cells and control non-target cells in C57BL/6 mice. Mice were treated with antibodies to deplete CD4, CD8, and NK cells. These findings suggest that changes in tumor growth after HDAC6 inhibition are in part, due to the immune recognition of the tumor.

Inhibition of HDAC6 Delays Tumor Progression In Vivo and is Dependent on Intact Immunity Mice were inoculated with B16 melanoma subcutaneously and the tumors were permitted to develop. When palpable, treatment with drug or vehicle control was administered three times weekly by intraperitoneal injections. A dose of 25 mg/kg Tubastatin A or Nexturastat A resulted in delayed tumor growth (FIG. 44A), with Nexturastat exhibiting a more pronounced effect. Similar results were observed when inoculating HDAC6KD cells, with a significant delay in tumor growth as compared with non-target control cells (FIG. 44B).

To assess the relative contribution of immunologic effects which were observed in vitro, the in vivo experiments were repeated in SCID mice. No change in the growth of HDAC6KD versus NT melanoma in SCID mice was observed, suggesting that a functional immune system is relevant in the decreased growth of HDAC6KD melanoma. To further characterize the relative contribution of anti-tumor immunity, specific subsets of cells were depleted via antibody depletion, which was confirmed by staining leukocytes from spleen. Depletion of NK, CD4, CD8, and combinations of these cells resulted in some decreased tumor growth, but not to the magnitude that was observed in mice with wild-type immune systems. Taken together, these observations support the anti-melanoma activity of a functional immune system after HDAC6 inhibition.

Discussion

It is disclosed herein that the inhibition of HDAC6 recapitulates many of the anti-tumor effects seen with pan-HDACi, namely, cell proliferation and immunomodulatory effects. This finding contrasts other reports demonstrating a cytotoxic effect of pan-HDACi on tumor viability due to the induction of apoptosis. No significant changes in cell viability by both PI FACS analysis or by PARP/caspase cleavage were observed. However, this would seem to be consistent with the increased specificity of targeting HDAC6 in these examples, as other HDACs have been more strongly implicated in inducing apoptosis. Rather, HDAC6 inhibition has been found to disrupt aggresome formation as well as signals that control cell cycle such as cyclin D, which provides a mechanistic rationale for these findings.

HDAC6 inhibition also caused immunomodulatory effects on melanoma cells including upregulation of MHC I and increased expression of known melanoma tumor antigens. The coordination of these phenomena is critical in augmenting the visibility of tumor cells to immune recognition and clearance. In contrast to prior reports demonstrating pan-HDACi-induced upregulation of CD86, the expression of this molecule at baseline or following HDACi treatment was not detected. Thus, this change likely occurs due to alternative HDACs, and not HDAC6.

In vitro observations of decreased cell proliferation and increased immunogenic signals was were confirmed in animal experiments. Specifically, delayed tumor growth was observed using both HDAC6i and HDAC6KD cells. By manipulating T lymphocyte subpopulations in the examples experiments, tumor growth rate was partially restored. This was most significant in experiments using SCID mice in which tumor growth was not decreased despite administering HDAC6i, while depletion of CD4, CD8, and NK cells resulted in partial slowing of tumor growth. This suggests an immunodominant affect for HDAC6 inhibition in the context of anti-tumor immunity. Although the primary effect we observed in vitro was through modulation of MHCI and tumor antigen exposure, this alone may not fully account for the in vivo observations. Indeed, results indicate a role for NK cells and both CD4+ and CD8+ T lymphocytes in the antitumor effects in the context of HDAC6 disruption.

The present disclosure demonstrates that the inhibition of HDAC6 results in both reduced proliferation and improved immune recognition, which are characteristic highly desired in anti-cancer therapies. Additionally, HDAC6i was able to inhibit the proliferation of a panel of human melanoma cell lines including both mutant and wild type NRAS/BRAF. The paucity of and resistance to treatments of BRAF wild-type melanoma underscores the significance of this finding. Thus, selective HDAC6 inhibitors could be considered as part of a potential treatment modality for the treatment of melanoma, particularly in combination with cytotoxic chemotherapy or as an additional immunotherapeutic agent that would compliment the mechanisms of current therapies. The materials and methods of the appended claims are not limited in scope by the specific materials and methods described herein, which are intended as illustrations of a few aspects of the claims and any materials and methods that are functionally equivalent are within the scope of this disclosure. Various modifications of the materials and methods in addition to those shown and described herein are intended to fall within the scope of the appended claims. Further, while only certain representative materials, methods, and aspects of these materials and methods are specifically described, other materials and methods and combinations of various features of the materials and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A compound having Formula I:

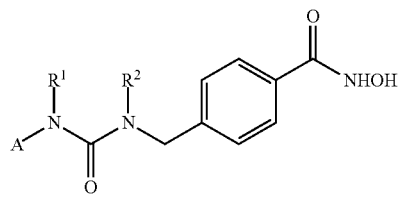

wherein
A is aryl, heteroaryl, or $C_1$-$C_8$ alkyl, any of which is optionally substituted with one or more groups chosen from acetyl, $C_1$-$C_5$ alkyl, amino, —$NR^6R^7$, —C(O)$NR^6R^7$, $C_1$-$C_4$ alkoxy, $C_1$-$C_4$ alkylhydroxy, $C_5$-$C_6$ cycloalkyl, $C_5$-$C_6$ heterocycloalkyl, aryl, heteroaryl, halo, hydroxy, thiol, cyano, or nitro; and $R^1$ is hydrogen and $R^2$ is $C_1$-$C_8$ alkyl, $C_1$-$C_8$ alkenyl, $C_1$-$C_8$ alkynyl, $C_1$-$C_8$ haloalkyl, $C_5$-$C_6$ cycloalkyl, $C_5$-$C_6$ heterocycloalkyl, $C_1$-$C_3$ alkylaryl, aryl, $C_1$-$C_3$ alkylheteroaryl, or heteroaryl, any of which is optionally substituted with acetyl, $C_1$-$C_5$ alkyl, amino, —$NR^6R^7$, —C(O)$NR^6R^7$, $C_1$-$C_4$ alkoxy, $C_1$-$C_4$ alkylhydroxy, $C_5$-$C_6$ cycloalkyl, $C_5$-$C_6$ heterocycloalkyl, aryl, heteroaryl, carbonyl, halo, hydroxy, thiol, cyano, or nitro; and $R^6$ and $R^7$ are independently H, $C_1$-$C_4$ alkyl, or are joined such that together they form an alkylene bridge comprising 4 or 5 atoms so that a 5 or 6-membered ring is formed with the nitrogen;

or a pharmaceutically acceptable salt or hydrate thereof.

2. The compound of claim 1, wherein A is phenyl, pyridyl, oxazolidyl, pyrimidyl, pyrimidinyl, or 1H-indazolyl, optionally substituted with $C_1$-$C_5$ alkyl, amino, alkoxy, alkylhydroxy, halo, hydroxy, or thiol.

3. The compound of claim 1, wherein A is pyrimidinyl or 1H-indazolyl substituted with $C_1$-$C_5$ alkyl, $C_1$-$C_4$ alkoxyl, or halo.

4. The compound of claim 1, wherein $R^2$ is $C_1$-$C_8$ alkyl, $C_5$-$C_6$ cycloalkyl, $C_5$-$C_6$ heterocycloalkyl, aryl, or heteroaryl, any of which is optionally substituted with $C_1$-$C_5$ alkyl, amino, —$NR^6R^7$, $C_1$-$C_4$ alkoxy, $C_1$-$C_4$ alkylhydroxy, carbonyl, hydroxy, thiol, or cyano.

5. The compound of claim 1, wherein $R^2$ is $C_1$-$C_5$ alkyl, or $C_1$-$C_5$ alkyl substituted with a methoxy, amino, —$NR^6R^7$, alkylhydroxy, carbonyl, hydroxy, cyano.
6. The compound of claim 1, wherein $R^2$ is $C_1$-$C_4$ alkyl.
7. The compound of claim 1, wherein the compound is chosen from:
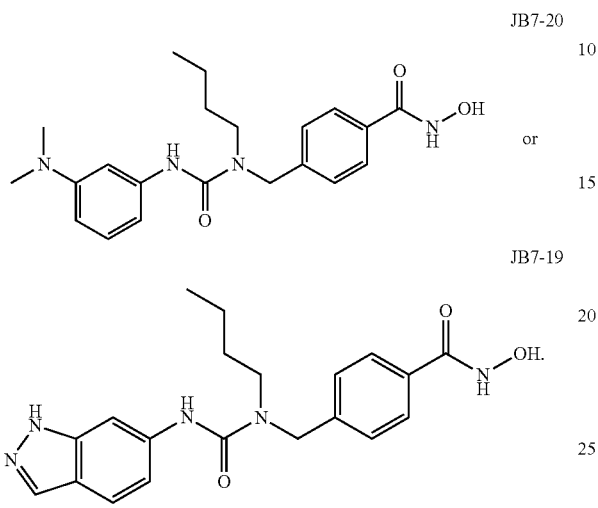
JB7-20
or
JB7-19
* * * * *